United States Patent
Mikkelsen et al.

(10) Patent No.: US 11,767,534 B2
(45) Date of Patent: Sep. 26, 2023

(54) MULTIPLEXED GENETIC REPORTER ASSAYS AND COMPOSITIONS

(75) Inventors: Tarjei Mikkelsen, Cambridge, MA (US); Andreas Gnirke, Wellesley, MA (US); Alexandre Melnikov, Bellingham, MA (US); Eric S. Lander, Cambridge, MA (US); Li Wang, Allston, MA (US); Xiaolan Zhang, Boston, MA (US)

(73) Assignee: THE BROAD INSTITUTE, INC., Cambridge, MA (US)

( * ) Notice: Subject to any disclaimer, the term of this patent is extended or adjusted under 35 U.S.C. 154(b) by 0 days.

(21) Appl. No.: 14/115,608

(22) PCT Filed: May 4, 2012

(86) PCT No.: PCT/US2012/036558
§ 371 (c)(1),
(2), (4) Date: Mar. 12, 2014

(87) PCT Pub. No.: WO2012/151503
PCT Pub. Date: Nov. 8, 2012

(65) Prior Publication Data
US 2014/0200163 A1 Jul. 17, 2014

Related U.S. Application Data

(60) Provisional application No. 61/482,419, filed on May 4, 2011.

(51) Int. Cl.
*C12N 15/63* (2006.01)
*C12N 15/10* (2006.01)

(52) U.S. Cl.
CPC ......... *C12N 15/63* (2013.01); *C12N 15/1086* (2013.01)

(58) Field of Classification Search
CPC .............. C12Q 1/6897; C12N 15/1086; C12N 15/1065; C12N 15/1058; C12N 15/63; C40B 40/06
See application file for complete search history.

(56) References Cited

U.S. PATENT DOCUMENTS

| | | | |
|---|---|---|---|
| 6,306,600 B1 * | 10/2001 | Kain | C07K 14/43595 435/320.1 |
| 6,368,825 B1 * | 4/2002 | Chao | C12N 15/86 435/235.1 |
| 2003/0224404 A1 * | 12/2003 | Vega | C12N 15/1058 506/1 |
| 2005/0053971 A1 * | 3/2005 | Chenchik | C12Q 1/6897 435/6.11 |
| 2005/0106559 A1 | 5/2005 | Radcliffe et al. | |
| 2005/0221491 A1 | 10/2005 | Mitrophanous et al. | |
| 2007/0161031 A1 * | 7/2007 | Trinklein | C12Q 1/6897 435/6.11 |
| 2009/0111099 A1 | 4/2009 | Ma et al. | |
| 2009/0263873 A1 * | 10/2009 | Godiska | C12N 9/90 435/91.41 |
| 2011/0027282 A1 | 2/2011 | Kotenko et al. | |
| 2011/0033920 A1 * | 2/2011 | Hartley | C12N 15/10 435/320.1 |

FOREIGN PATENT DOCUMENTS

| | | | | |
|---|---|---|---|---|
| WO | WO-94/25609 A1 | 11/1994 | | |
| WO | WO-9855657 A1 * | 12/1998 | ......... | C12N 15/1051 |
| WO | WO-9955886 A1 * | 11/1999 | ......... | C12N 15/1034 |
| WO | WO 0155371 A1 * | 8/2001 | ......... | C12N 15/1048 |
| WO | WO-0214553 A2 * | 2/2002 | ............. | C12N 15/10 |
| WO | WO-2009/124012 A1 | 10/2009 | | |

OTHER PUBLICATIONS

Kumaki et al. Analysis and synthesis of high-amplitude Cis-elements in the mammalian circadian clock. Proceedings of the National Academy of Sciences, USA, vol. 105, No. 39, pp. 14946-14951, Sep. 2008, including pp. 1/33-33/33 of SI Appendix.*
Desai et al. Engineering transcription factors with novel DNA-binding specificity using comparative genomics. Nucleic Acids Research, vol. 37, No. 8, pp. 2493-2503, 2009.*
Patwardhan et al. Nature Biotechnology, vol. 27, No. 12, pp. 1173-1175, 2009, including pp. 19-19/19 of Supplementary Information. (Year: 2009).*
Alam and Cook. "Reporter genes for monitoring gene expression in mammalian cells." Gene Transfer and Expression in Mammalian Cells. Ed. S.C. Makrides. Elsevier Science B.V., 2003. 291-308. (Year: 2003).*
McNabb et al. Dual Luciferase Assay System for Rapid Assessment of Gene Expression in *Saccharomyces cerevisiae*. Eukaryotic Cell, vol. 4, No. 9, pp. 1539-1549, 2005. (Year: 2005).*
Sherf, B. A., S. L. Navarro, R.R. Hannah, and K. V. Wood. 1996. Dual-luciferase reporter assay: an advanced co-reporter technology integrating firefly and Renilla luciferase assays. Promega Notes 57:2-8. [Online.] http://www.promega.com/pnotes/57/5573a/5573a.html. (Year: 1996).*
Alcaraz-Pérez et al. Application of the dual-luciferase reporter assay to the analysis of promoter activity in Zebrafish embryos. BMC Biotechnology, vol. 8, 81, Oct. 2008, printed as pp. 1/8-8/8. (Year: 2008).*

(Continued)

*Primary Examiner* — Jennifer Dunston
(74) *Attorney, Agent, or Firm* — F. Brent Nix, Esq.; Johnson, Marcou, Isaacs & Nix, LLC

(57) ABSTRACT

The invention provides methods for determining the activity of a plurality of nucleic acid regulatory elements. These methods may facilitate, e.g., the systematic reverse engineering, and optimization of mammalian cis-regulatory elements at high resolution and at a large scale. The method may include integration of multiplexed DNA synthesis and sequencing technologies to generate and quantify the transcriptional regulatory activity of e.g., thousands of arbitrary DNA sequences in parallel in cell-based as says (e.g., mammalian cell based assays).

20 Claims, 24 Drawing Sheets
Specification includes a Sequence Listing.

(56) References Cited

OTHER PUBLICATIONS

Chujo et al. Promoter Analysis of the Elicitor-Induced WRKY Gene OsWRKY53, Which Is Involved in Defense Responses in Rice, Bioscience, Biotechnology, and Biochemistry, 73:8, 1901-1904, 2009. (Year: 2009).*
He et al. Identification of Androgen-Responsive Element (ARE) and Sp1 element in the Maspin Promoter. Chinese Journal of Physiology, vol. 48, No. 3, pp. 160-166, 2005. (Year: 2005).*
Kumar et al. Systematic characterisation of the rat and human CYP24A1 promoter. Molecular and Cellular Endocrinology, vol. 325, pp. 46-53, 2010. (Year: 2010).*
Li et al. Cloning and Functional Characterization of the 5'-regulatory Region of the Human CD86 Gene. Human Immunology, vol. 61, pp. 486-498, May 2000. (Year: 2000).*
Chen et al. Cloning and characterization of the human CD200 promoter region. Molecular Immunology, vol. 43, pp. 579-587, 2006. (Year: 2006).*
Nevoigt et al. Engineering Promoter Regulation. Biotechnology and Bioengineering, vol. 96, No. 3, pp. 550-558, 2007, including pp. 1/2 of Supplementary Information. (Year: 2007).*
Entry for "throughout" from Webster's New World College Dictionary, Fifth Edition Copyright © 2014 by Houghton Mifflin Harcourt Publishing Company, printed as p. 1/1 from yourdictionary.com (Year: 2014).*
Nam et al. Functional cis-regulatory genomics for systems biology. Proceedings of the National Academy of Sciences, USA, vol. 107, No. 8, pp. 3930-3935, Feb. 23, 2010, including pp. 1/406-406/406 of supporting information. (Year: 2010).*
Greene, JM. "Unit 8.4 Linker-Scanning Mutagenesis of DNA" in Current Protocols in Molecular Biology (1988), pp. 8.4.1-8.4.7, Copyright © by John Wiley & Sons, Inc. (Year: 1988).*
Roberts, RJ. Restriction enzymes and their isoschizomers. Nucleic Acids Research, vol. 15, Supplement, pp. r189-r217, Jan. 1, 1987. (Year: 1987).*
Xu et al. Design of 240,000 orthogonal 25mer DNA barcode probes. Proceedings of the National Academy of Sciences, USA, vol. 106, No. 7, pp. 2289-2294, Feb. 17, 2009. (Year: 2009).*
Frank, DN. BARCRAWL and BARTAB: software tools for the design and implementation of barcoded primers for highly multiplexed DNA sequencing. BMC Bioinformatics, vol. 10, 362, Oct. 29, 2009, printed as pp. 1/13-13/13. (Year: 2009).*
Parameswaran et al. A pyrosequencing-tailored nucleotide barcode design unveils opportunities for large-scale sample multiplexing. Nucleic Acids Research, vol. 35, No. 19, e130, pp. 1/9-9/9, pp. 1/18-18/18 of Supplementary Tables, and pp. 1/4-4/4 of Supplementary Information, Oct. 11, 2007. (Year: 2007).*
Kinney et al., "Using deep sequencing to characterize the biophysical mechanism of a transcriptional regulatory sequence," Proc Natl Acad Sci U S A. 107(20):9158-63 (2010).
Melnikov et al., "Systematic dissection and optimization of inducible enhancers in human cells using a massively parallel reporter assay," Nat Biotechnol. 30(3):271-7 (2012).
Patwardhan et al., "High-resolution analysis of DNA regulatory elements by synthetic saturation mutagenesis," Nat Biotechnol. 27(12):1173-5 (2009).
Supplementary European Search Report for European Patent Application No. EP 12779510.2, dated Oct. 15, 2014 (8 pages).
International Preliminary Report on Patentability for International Patent Application No. PCT/US2012/036558, dated Nov. 14, 2013 (7 pages).
Chung et al., "A versatile vector system for multiple gene expression in plants," Trends Plant Sci. 10(8):357-61 (2005).
International Search Report and Written Opinion for International Patent Application PCT/US2012/036558, dated Dec. 14, 2012 (9 pages).

* cited by examiner

CR  GCACCAGACAGTGACGTCAGCTGCCAGATCCCATGGCCGTCATACTGTGACGTCTTTCAGACACCCCATTGACGTCAATGGGAGAAC

SEQUENCE LISTING

```
<160> NUMBER OF SEQ ID NOS: 56

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 1
ttagcctgca                                                          10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctgcattagc                                                          10

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
attgacgtca at                                                       12

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
agtgacgtca gc                                                       12

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
actggccgct tcactg                                                   16

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggtacctcta ga                                                       12

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agatcggaag agcgtcg                                                17

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgacgctctt ccgatct                                                17

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gctaagggcc taactggccg cttcactg                                    28

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtttaaggcc tccgaggccg acgctcttc                                   29

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctggcctaac tggccgcttc actg                                        24

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ggtacctgag ctcgc                                                  15

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctggcctaac tggcc                                                  15

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcgagctcag gtacc                                                  15

<210> SEQ ID NO 15
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aatgatacgg cgaccaccga gatctacact ctttccctac acgacgctct tccgatct   58

<210> SEQ ID NO 16
<211> LENGTH: 81
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(32)
<223> OTHER INFORMATION: a, c, t, g, unknown or other

<400> SEQUENCE: 16
caagcagaag acggcatacg agatnnnnnn nngtgactgg agttcagacg tgtgctcttc   60
cgatctcgag gtgcctaaag g                                            81

<210> SEQ ID NO 17
<211> LENGTH: 185
<212> TYPE: DNA
<213> ORGANISM: Mus sp.

<400> SEQUENCE: 17
cggattcttg gcaagccatg cgacaaaggc agaaatgcac atttcaccca gagagaaggg   60
attgtagtca gcaggaagtc accacccaga gagcaaatgg agttcccaga tgcctgacat  120
ttgccttctt actggatcag agttcactag tggaagtgtc acagcccaaa cactccccca  180
aaggc                                                             185

<210> SEQ ID NO 18
<211> LENGTH: 185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gaaatgtgca tttctgcctt tgtcgcatgg cttgccaaga atccgaccca gagagaaggg   60
attgtagtca gcaggaagtc accacccaga gagcaaatgg agttcccaga tgcctgacat  120
ttgccttctt actggatcag agttcactag tggaagtgtc acagcccaaa cactccccca    180
aaggc    185

<210> SEQ ID NO 19
<211> LENGTH: 185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
ctctgggtgg tgacttcctg ctgactacaa tcccttctct ctgggtgaaa tgtgcatttc    60
tgcctttgtc gcatggcttg ccaagaatcc gagcaaatgg agttcccaga tgcctgacat    120
ttgccttctt actggatcag agttcactag tggaagtgtc acagcccaaa cactccccca    180
aaggc    185

<210> SEQ ID NO 20
<211> LENGTH: 87
<212> TYPE: DNA
<213> ORGANISM: Unknown
<220> FEATURE:
<223> OTHER INFORMATION: Description of Unknown: CRE
      oligonucleotide

<400> SEQUENCE: 20
gcaccagaca gtgacgtcag ctgccagatc ccatggccgt catactgtga cgtctttcag    60 acacccatt gacgtcaatg ggagaac    87

<210> SEQ ID NO 21
<211> LENGTH: 152
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (17)..(113)
<223> OTHER INFORMATION: a, c, t, g, unknown or other
<220> FEATURE:
<221> NAME/KEY: modified_base
<222> LOCATION: (126)..(135)
<223> OTHER INFORMATION: a, c, t, g, unknown or other

<400> SEQUENCE: 21
actggccgct tcactgnnnn nnnnnnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnggtacct    120
ctagannnnn nnnnnagatc ggaagagcgt cg    152

<210> SEQ ID NO 22
<211> LENGTH: 182
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (29)..(125)
<223> OTHER INFORMATION: a, c, t, g, unknown or other
<220> FEATURE:
<221> NAME/KEY: modified_base
<222> LOCATION: (138)..(147)

<223> OTHER INFORMATION: a, c, t, g, unknown or other

<400> SEQUENCE: 22

```
gctaagggcc taactggccg cttcactgnn nnnnnnnnnn nnnnnnnnnn nnnnnnnnnn        60
nnnnnnnnnn nnnnnnnnnn nnnnnnnnnn nnnnnnnnnn nnnnnnnnnn nnnnnnnnnn       120
nnnnnggtac tctagannnn nnnnnnnaga tcggaagagc gtcggcctcg gaggccttaa       180
ac                                                                     182
```

<210> SEQ ID NO 23
<211> LENGTH: 182
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (36)..(45)
<223> OTHER INFORMATION: a, c, t, g, unknown or other
<220> FEATURE:
<221> NAME/KEY: modified_base
<222> LOCATION: (58)..(154)
<223> OTHER INFORMATION: a, c, t, g, unknown or other

<400> SEQUENCE: 23

```
gtttaaggcc tccgaggccg acgctcttcc gatctnnnnn nnnnntctag aggtaccnnn        60
nnnnnnnnnn nnnnnnnnnn nnnnnnnnnn nnnnnnnnnn nnnnnnnnnn nnnnnnnnnn       120
nnnnnnnnnn nnnnnnnnnn nnnnnnnnnn nnnncagtga agcggccagt taggcccttta      180 gc                                                                     182
```

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24

```
tttctctggc ctaac                                                        15
```

<210> SEQ ID NO 25
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25

```
aggccagaga aa                                                           12
```

<210> SEQ ID NO 26
<211> LENGTH: 157
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (15)..(111)
<223> OTHER INFORMATION: a, c, t, g, unknown or other
<220> FEATURE:
<221> NAME/KEY: modified_base
<222> LOCATION: (124)..(133)
<223> OTHER INFORMATION: a, c, t, g, unknown or other

<400> SEQUENCE: 26
tggccgcttc actgnnnnnn nnnnnnnnnn nnnnnnnnnn nnnnnnnnnn        60
nnnnnnnnnn nnnnnnnnnn nnnnnnnnnn nnnnnnnnnn nnnnnnnnnn nggtacctct   120
agannnnnnn nnnagatcgg aagagcgtcg gcctcgg      157

<210> SEQ ID NO 27
<211> LENGTH: 157
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (22)..(31)
<223> OTHER INFORMATION: a, c, t, g, unknown or other
<220> FEATURE:
<221> NAME/KEY: modified_base
<222> LOCATION: (44)..(140)
<223> OTHER INFORMATION: a, c, t, g, unknown or other

<400> SEQUENCE: 27
aggccgacgc tcttccgatc tnnnnnnnnn ntctagaggt accnnnnnnn nnnnnnnnnn   60
nnnnnnnnnn nnnnnnnnnn nnnnnnnnnn nnnnnnnnnn nnnnnnnnnn nnnnnnnnnn  120
nnnnnnnnnn nnnnnnnnnn cagtgaagcg gccagtt      157

<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gatcgaaccg gc           12

<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gccgccggtt cgatc         15

<210> SEQ ID NO 30
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(97)
<223> OTHER INFORMATION: a, c, t, g, unknown or other

<400> SEQUENCE: 30
nnnnnnnnnn nnnnnnnnnn nnnnnnnnnn nnnnnnnnnn nnnnnnnnnn nnnnnnnnnn   60
nnnnnnnnnn nnnnnnnnnn nnnnnnnnnn nnnnnnnggt ac                    102

<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(15)
<223> OTHER INFORMATION: a, c, t, g, unknown or other

<400> SEQUENCE: 31
ctagannnnn nnnnnagatc ggaagagcgt cggc                              34

<210> SEQ ID NO 32
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(98)
<223> OTHER INFORMATION: a, c, t, g, unknown or other

<400> SEQUENCE: 32
cnnnnnnnnn nnnnnnnnnn nnnnnnnnnn nnnnnnnnnn nnnnnnnnnn nnnnnnnnnn    60
nnnnnnnnnn nnnnnnnnnn nnnnnnnnnn nnnnnnnn                           98

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(29)
<223> OTHER INFORMATION: a, c, t, g, unknown or other

<400> SEQUENCE: 33
gccgacgctc ttccgatctn nnnnnnnnnt                                   30

<210> SEQ ID NO 34
<211> LENGTH: 1782
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(1781)
<223> OTHER INFORMATION: a, c, t, g, unknown or other

<400> SEQUENCE: 34
cnnnnnnnnn nnnnnnnnnn nnnnnnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn   120
nnnnnnnnnn nnnnnnnnnn nnnnnnnnnn nnnnnnnnnn nnnnnnnnnn nnnnnnnnnn   180
nnnnnnnnnn nnnnnnnnnn nnnnnnnnnn nnnnnnnnnn nnnnnnnnnn nnnnnnnnnn   240
nnnnnnnnnn nnnnnnnnnn nnnnnnnnnn nnnnnnnnnn nnnnnnnnnn nnnnnnnnnn   300

```
nnnnnnnnnn nnnnnnnnnn nnnnnnnnnn nnnnnnnnnn nnnnnnnnnn nnnnnnnnnn       360
nnnnnnnnnn nnnnnnnnnn nnnnnnnnnn nnnnnnnnnn nnnnnnnnnn nnnnnnnnnn       420
nnnnnnnnnn nnnnnnnnnn nnnnnnnnnn nnnnnnnnnn nnnnnnnnnn nnnnnnnnnn       480
nnnnnnnnnn nnnnnnnnnn nnnnnnnnnn nnnnnnnnnn nnnnnnnnnn nnnnnnnnnn       540
nnnnnnnnnn nnnnnnnnnn nnnnnnnnnn nnnnnnnnnn nnnnnnnnnn nnnnnnnnnn       600
nnnnnnnnnn nnnnnnnnnn nnnnnnnnnn nnnnnnnnnn nnnnnnnnnn nnnnnnnnnn       660
nnnnnnnnnn nnnnnnnnnn nnnnnnnnnn nnnnnnnnnn nnnnnnnnnn nnnnnnnnnn       720
nnnnnnnnnn nnnnnnnnnn nnnnnnnnnn nnnnnnnnnn nnnnnnnnnn nnnnnnnnnn       780
nnnnnnnnnn nnnnnnnnnn nnnnnnnnnn nnnnnnnnnn nnnnnnnnnn nnnnnnnnnn       840
nnnnnnnnnn nnnnnnnnnn nnnnnnnnnn nnnnnnnnnn nnnnnnnnnn nnnnnnnnnn       900
nnnnnnnnnn nnnnnnnnnn nnnnnnnnnn nnnnnnnnnn nnnnnnnnnn nnnnnnnnnn       960
nnnnnnnnnn nnnnnnnnnn nnnnnnnnnn nnnnnnnnnn nnnnnnnnnn nnnnnnnnnn      1020
nnnnnnnnnn nnnnnnnnnn nnnnnnnnnn nnnnnnnnnn nnnnnnnnnn nnnnnnnnnn      1080
nnnnnnnnnn nnnnnnnnnn nnnnnnnnnn nnnnnnnnnn nnnnnnnnnn nnnnnnnnnn      1140
nnnnnnnnnn nnnnnnnnnn nnnnnnnnnn nnnnnnnnnn nnnnnnnnnn nnnnnnnnnn      1200
nnnnnnnnnn nnnnnnnnnn nnnnnnnnnn nnnnnnnnnn nnnnnnnnnn nnnnnnnnnn      1260
nnnnnnnnnn nnnnnnnnnn nnnnnnnnnn nnnnnnnnnn nnnnnnnnnn nnnnnnnnnn      1320
nnnnnnnnnn nnnnnnnnnn nnnnnnnnnn nnnnnnnnnn nnnnnnnnnn nnnnnnnnnn      1380
nnnnnnnnnn nnnnnnnnnn nnnnnnnnnn nnnnnnnnnn nnnnnnnnnn nnnnnnnnnn      1440
nnnnnnnnnn nnnnnnnnnn nnnnnnnnnn nnnnnnnnnn nnnnnnnnnn nnnnnnnnnn      1500
nnnnnnnnnn nnnnnnnnnn nnnnnnnnnn nnnnnnnnnn nnnnnnnnnn nnnnnnnnnn      1560
nnnnnnnnnn nnnnnnnnnn nnnnnnnnnn nnnnnnnnnn nnnnnnnnnn nnnnnnnnnn      1620
nnnnnnnnnn nnnnnnnnnn nnnnnnnnnn nnnnnnnnnn nnnnnnnnnn nnnnnnnnnn      1680
nnnnnnnnnn nnnnnnnnnn nnnnnnnnnn nnnnnnnnnn nnnnnnnnnn nnnnnnnnnn      1740
nnnnnnnnnn nnnnnnnnnn nnnnnnnnnn nnnnnnnnnn nt                         1782

<210> SEQ ID NO 35
<211> LENGTH: 1789
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (6)..(1785)
<223> OTHER INFORMATION: a, c, t, g, unknown or other

<400> SEQUENCE: 35
ctagannnnn nnnnnnnnnn nnnnnnnnnn nnnnnnnnnn nnnnnnnnnn nnnnnnnnnn        60
nnnnnnnnnn nnnnnnnnnn nnnnnnnnnn nnnnnnnnnn nnnnnnnnnn nnnnnnnnnn       120
nnnnnnnnnn nnnnnnnnnn nnnnnnnnnn nnnnnnnnnn nnnnnnnnnn nnnnnnnnnn       180
nnnnnnnnnn nnnnnnnnnn nnnnnnnnnn nnnnnnnnnn nnnnnnnnnn nnnnnnnnnn       240
nnnnnnnnnn nnnnnnnnnn nnnnnnnnnn nnnnnnnnnn nnnnnnnnnn nnnnnnnnnn       300
nnnnnnnnnn nnnnnnnnnn nnnnnnnnnn nnnnnnnnnn nnnnnnnnnn nnnnnnnnnn       360
nnnnnnnnnn nnnnnnnnnn nnnnnnnnnn nnnnnnnnnn nnnnnnnnnn nnnnnnnnnn       420
```

```
nnnnnnnnnn nnnnnnnnnn nnnnnnnnnn nnnnnnnnnn nnnnnnnnnn nnnnnnnnnn      480
nnnnnnnnnn nnnnnnnnnn nnnnnnnnnn nnnnnnnnnn nnnnnnnnnn nnnnnnnnnn      540
nnnnnnnnnn nnnnnnnnnn nnnnnnnnnn nnnnnnnnnn nnnnnnnnnn nnnnnnnnnn      600
nnnnnnnnnn nnnnnnnnnn nnnnnnnnnn nnnnnnnnnn nnnnnnnnnn nnnnnnnnnn      660
nnnnnnnnnn nnnnnnnnnn nnnnnnnnnn nnnnnnnnnn nnnnnnnnnn nnnnnnnnnn      720
nnnnnnnnnn nnnnnnnnnn nnnnnnnnnn nnnnnnnnnn nnnnnnnnnn nnnnnnnnnn      780
nnnnnnnnnn nnnnnnnnnn nnnnnnnnnn nnnnnnnnnn nnnnnnnnnn nnnnnnnnnn      840
nnnnnnnnnn nnnnnnnnnn nnnnnnnnnn nnnnnnnnnn nnnnnnnnnn nnnnnnnnnn      900
nnnnnnnnnn nnnnnnnnnn nnnnnnnnnn nnnnnnnnnn nnnnnnnnnn nnnnnnnnnn      960
nnnnnnnnnn nnnnnnnnnn nnnnnnnnnn nnnnnnnnnn nnnnnnnnnn nnnnnnnnnn     1020
nnnnnnnnnn nnnnnnnnnn nnnnnnnnnn nnnnnnnnnn nnnnnnnnnn nnnnnnnnnn     1080
nnnnnnnnnn nnnnnnnnnn nnnnnnnnnn nnnnnnnnnn nnnnnnnnnn nnnnnnnnnn     1140
nnnnnnnnnn nnnnnnnnnn nnnnnnnnnn nnnnnnnnnn nnnnnnnnnn nnnnnnnnnn     1200
nnnnnnnnnn nnnnnnnnnn nnnnnnnnnn nnnnnnnnnn nnnnnnnnnn nnnnnnnnnn     1260
nnnnnnnnnn nnnnnnnnnn nnnnnnnnnn nnnnnnnnnn nnnnnnnnnn nnnnnnnnnn     1320
nnnnnnnnnn nnnnnnnnnn nnnnnnnnnn nnnnnnnnnn nnnnnnnnnn nnnnnnnnnn     1380
nnnnnnnnnn nnnnnnnnnn nnnnnnnnnn nnnnnnnnnn nnnnnnnnnn nnnnnnnnnn     1440
nnnnnnnnnn nnnnnnnnnn nnnnnnnnnn nnnnnnnnnn nnnnnnnnnn nnnnnnnnnn     1500
nnnnnnnnnn nnnnnnnnnn nnnnnnnnnn nnnnnnnnnn nnnnnnnnnn nnnnnnnnnn     1560
nnnnnnnnnn nnnnnnnnnn nnnnnnnnnn nnnnnnnnnn nnnnnnnnnn nnnnnnnnnn     1620
nnnnnnnnnn nnnnnnnnnn nnnnnnnnnn nnnnnnnnnn nnnnnnnnnn nnnnnnnnnn     1680
nnnnnnnnnn nnnnnnnnnn nnnnnnnnnn nnnnnnnnnn nnnnnnnnnn nnnnnnnnnn     1740
nnnnnnnnnn nnnnnnnnnn nnnnnnnnnn nnnnnnnnnn nnnnngtac                 1789

<210> SEQ ID NO 36
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (47)..(56)
<223> OTHER INFORMATION: a, c, u, g, unknown or other

<400> SEQUENCE: 36
auuaaggcca agaagggcgg caagaucgcc guguaauaau ucuagannnn nnnnnnagau      60
cggaagagcg ucggc                                                      75

<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
aaaaaaaaaa aaaaaaaaa aaaaaaaaa                                        29
```

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tttttttttt tttttttttt tttt                                                24

<210> SEQ ID NO 39
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(29)
<223> OTHER INFORMATION: a, c, t, g, unknown or other

<400> SEQUENCE: 39
gccgacgctc ttccgatctn nnnnnnnnnt ctagaattat tacacggcga tcttgccgcc         60
cttcttggcc ttaat                                                          75

<210> SEQ ID NO 40
<211> LENGTH: 188
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (34)..(43)
<223> OTHER INFORMATION: a, c, t, g, unknown or other
<220> FEATURE:
<221> NAME/KEY: modified_base
<222> LOCATION: (50)..(139)
<223> OTHER INFORMATION: a, c, t, g, unknown or other

<400> SEQUENCE: 40
acactctttc cctacacgac gctcttccga tctnnnnnnn nnntctagan nnnnnnnnn          60 nnnnnnnnnn nnnnnnnnnn nnnnnnnnnn nnnnnnnnnn nnnnnnnnnn nnnnnnnnnn        120
nnnnnnnnnn nnnnnnnnnc ctttaggcac ctcgagatcg gaagagcaca cgtctgaact        180
ccagtcac                                                                 188

<210> SEQ ID NO 41
<211> LENGTH: 188
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (50)..(139)
<223> OTHER INFORMATION: a, c, t, g, unknown or other
<220> FEATURE:
<221> NAME/KEY: modified_base
<222> LOCATION: (146)..(155)
<223> OTHER INFORMATION: a, c, t, g, unknown or other

<400> SEQUENCE: 41
gtgactggag ttcagacgag agctcttccg atctcgaggt gcctaaaggn nnnnnnnnn          60

```
nnnnnnnnnn nnnnnnnnnn nnnnnnnnnn nnnnnnnnnn nnnnnnnnnn nnnnnnnnnn    120
nnnnnnnnnn nnnnnnnnna gatctnnnnn nnnnnagatc ggaagagcgt cgtgtaggga    180
aagagtgt                                                              188

<210> SEQ ID NO 42
<211> LENGTH: 87
<212> TYPE: DNA
<213> ORGANISM: Unknown
<220> FEATURE:
<223> OTHER INFORMATION: Description of Unknown: CRE
      oligonucleotide

<400> SEQUENCE: 42
gttctcccat tgacgtcaat ggggtgtctg aaagacgtca cagtatgacg gccatgggat    60
ctggcagctg acgtcactgt ctggtgc                                        87

<210> SEQ ID NO 43
<211> LENGTH: 87
<212> TYPE: DNA
<213> ORGANISM: Unknown
<220> FEATURE:
<223> OTHER INFORMATION: Description of Unknown: IFNB
      oligonucleotide

<400> SEQUENCE: 43
tagaaactac taaatgtaa atgacatagg aaaactgaaa gggagaagtg aaagtgggaa     60
attcctctga atagagagag gaccatc                                        87

<210> SEQ ID NO 44
<211> LENGTH: 87
<212> TYPE: DNA
<213> ORGANISM: Unknown
<220> FEATURE:
<223> OTHER INFORMATION: Description of Unknown: IFNB
      oligonucleotide

<400> SEQUENCE: 44
gatggtcctc tctctattca gaggaatttc ccactttcac ttctcccttt cagttttcct    60
atgtcattta cattttagta gtttcta                                        87

<210> SEQ ID NO 45
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tcgcgagaca ttgacgtcag ccgactctgt acgctaacgt catccactga cgtctgtctc    60
ccgggggatt gacgtcaatg cgctgga                                        87

<210> SEQ ID NO 46
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tccagcgcat tgacgtcaat cccccgggag acagacgtca gtggatgacg ttagcgtaca    60
```
gagtcggctg acgtcaatgt ctcgcga                                        87

<210> SEQ ID NO 47
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
acaccagaca ttgacgtcag cagccagatc gcattcccgt cattctctga cgtctatcag    60
acaccccatt gacgtcaatg ggagaaa                                        87

<210> SEQ ID NO 48
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tttctcccat tgacgtcaat ggggtgtctg atagacgtca gagaatgacg ggaatgcgat    60
ctggctgctg acgtcaatgt ctggtgt                                        87

<210> SEQ ID NO 49
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
acaccagaca ttgacgtaag ctgactaatc ccattcccgt catactctga cgtcttttag    60
acatcccatt gacgtcaatg ggaaaac                                        87

<210> SEQ ID NO 50
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gttttcccat tgacgtcaat gggatgtcta aaagacgtca gagtatgacg ggaatgggat    60
tagtcagctt acgtcaatgt ctggtgt                                        87

<210> SEQ ID NO 51
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
acaccagaca ttgacgtaag ctgccagatc ccattcccgt catactctga cgtctttcag    60
acaccccatt gacgtcaatg ggagaac                                        87

```
<210> SEQ ID NO 52
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gttctcccat tgacgtcaat ggggtgtctg aaagacgtca gagtatgacg ggaatgggat      60
ctggcagctt acgtcaatgt ctggtgt                                          87

<210> SEQ ID NO 53
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tagaaactac taaaatgtaa atgaggaaag gaaacggaaa ctggaaacgg aaactgggga      60
attccactga atagagagag gaccatc                                          87

<210> SEQ ID NO 54
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gatggtcctc tctctattca gtggaattcc ccagtttccg tttccagttt ccgtttcctt      60
tcctcattta cattttagta gtttcta                                          87

<210> SEQ ID NO 55
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
tagaaactac taaaatgtaa atgacatagg aaaactgaaa ctgagaacgg aaactgggaa      60
attcccctga atagagagag gaccatc                                          87

<210> SEQ ID NO 56
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gatggtcctc tctctattca ggggaatttc ccagtttccg ttctcagttt cagttttcct      60
atgtcattta cattttagta gtttcta                                          87
```

MULTIPLEXED GENETIC REPORTER ASSAYS AND COMPOSITIONS

CROSS REFERENCE TO RELATED APPLICATION

This application is the U.S. national stage filing under 35 U.S.C. § 371 of International Application PCT/US2012/036558, filed May 4, 2012, which claims benefit of U.S. Provisional Application No. 61/482,419, filed May 4, 2011.

REFERENCE TO SEQUENCE LISTING

The instant application contains a Sequence Listing which has been submitted electronically in ASCII format and is hereby incorporated by reference in its entirety. Said ASCII copy, created Mar. 12, 2014, is named 50790-002002_SL.txt and is 23,533 bytes in size.

BACKGROUND OF THE INVENTION

This invention relates to compositions and methods for assaying the biological activities of large numbers of nucleic acid regulatory elements.

Gene expression programs that drive development, differentiation, and many physiological processes are in large part encoded by DNA and RNA sequence elements that recruit regulatory proteins and their co-factors to specific genomic loci or genes under specific conditions. Despite significant research efforts, the relationship between the nucleic acid sequence and the function of these regulatory elements, such as cis-regulatory elements, remains poorly understood. While the discovery of the genetic code has allowed interpretation of protein-coding sequences with relative ease, no analogous regulatory code has been described. This limited understanding of cis-regulatory elements is an impediment to a variety of fields, including synthetic biology, medical genetics, and evolutionary biology.

Many applications of synthetic biology, including construction of (i) reporter systems for use in high-throughput drug screening, (ii) cell type-specific vectors for use in gene therapy, and (iii) metabolic pathways for bioproduction, require establishing tight control over the expression of one or more genes within a complex biological system. Our ability to engineer genetic regulatory systems that can provide such control is predicated on improving our understanding of the cis-regulatory code and on development of efficient methods for testing prototype regulatory elements.

Recent advances in genotyping and DNA sequencing technologies have led to a revolution in research on genetic factors that influence health and disease. Over the past few years, the number of published, reproducible associations between genetic variants that segregate in the human population and disease-relevant traits has increased from a handful to over one thousand. Due to linkage disequilibrium and other confounding factors, the genetic variants that actually cause the traits are not necessarily those identified by the association studies. A strikingly common observation, however, is that many of the yet-to-be-found causal variants are thought to be located in cis-regulatory elements. Translating the results of genome-wide association and re-sequencing studies into biomedical insights will therefore require improved methods for recognizing genetic variants that can influence the function of cis-regulatory elements.

Comparative studies of animal genomes, both between closely related species, such as humans and great apes, and distantly related species such as placental mammals and birds, have consistently found that functional non-coding sequences evolve and turn over at significantly faster rates than protein-coding sequences. Much of the evolution of diversity in the animal kingdom, particularly morphological diversity, is therefore thought to have been driven by changes in gene regulation. Understanding the genetic basis of this evolution and tracing the evolutionary history of our own species is therefore predicated on understanding how mutations in cis-regulatory elements translate into changes in developmental gene expression patterns.

Clearly, new approaches to elucidate the relationship between DNA sequences and the function of cis-regulatory elements are needed. The present application provides such approaches.

SUMMARY OF THE INVENTION

In one aspect, the invention features a plurality of expression vectors where each of the expression vectors includes: a nucleic acid regulatory element, an open reading frame, and an identifying nucleic acid tag; the open reading frame (e.g., an open reading frame encoding a fluorescent protein or a luciferase) of each of the plurality of expression vectors is identical; the plurality of expression vectors include a plurality of distinct nucleic acid regulatory elements; and each of the identifying tags is paired with a corresponding nucleic acid regulatory element. The nucleic acid regulatory element is, for example, located upstream, downstream, or within the open reading frame.

In another aspect, the invention features a population of cells including expression vectors which include: a nucleic acid regulatory element, an open reading frame, and an identifying nucleic acid tag; where the open reading frame (e.g., an open reading frame encoding a fluorescent protein or a luciferase) of each of the plurality of expression vectors is identical; the plurality of expression vectors include a plurality of distinct nucleic acid regulatory elements; and each of the identifying nucleic acid tags is paired with a corresponding nucleic acid regulatory element. The nucleic acid regulatory element is, for example, located upstream of the open reading frame.

In any of the foregoing aspects, each identifying tag may include a sequence that is unique over a stretch of at least ten nucleotides as compared to the remaining nucleic acid tags and/or be at least ten nucleotides in length. Furthermore, each distinct nucleic acid regulatory element may correspond to one, two, or more nucleic acid tags.

In any of the foregoing aspects, the expression vector may also include an identical stretch of nucleotides (e.g., a transcriptional terminator or poly-adenylation signal, which may include the DNA sequences AATAAA or ATTAAA) located 3' to the identifying nucleic acid tag.

In any of the foregoing aspects, each distinct regulatory element may be a variant of a single regulatory element and/or each distinct regulatory element may differ from the remaining distinct regulatory elements by a single nucleotide substitution, deletion, or insertion. For example, among the distinct regulatory elements may be regulatory elements including at least one nucleotide substitutions of every nucleotide of the single regulatory element. Alternatively (or additionally), each distinct regulatory element may differ from the remaining distinct regulatory elements by two or more single nucleotide substitutions, deletions, insertions, or combinations thereof.

In another aspect, the invention features a method of determining individual activities of a plurality of nucleic acid regulatory elements by introducing any of the foregoing plurality of expression vectors into cells. This method, in general, includes expression of the open reading frames and the tags and the determination of this expression (e.g., by quantitatively sequencing the nucleic acid molecules resulting from the cDNA synthesis or determining the quantity of mRNA hybridized to nucleic acid molecules complementary to the tags). Here, the amount of each tag detected is an indication of the activity of a corresponding nucleic acid regulatory element. This method may also include isolating mRNA (e.g., by poly-A isolation) from the cells prior to the determining the amount of the tags expressed in the cells. Furthermore, this method may also include first strand cDNA synthesis using the isolated mRNA as a template. Additionally, this method may include determining the amount of each tag in the plurality of expression vectors by quantitatively sequencing the plurality of expression vectors and, e.g., by normalizing the amount of the tags expressed in the cells against the amount of each of the tags in the plurality of expression vectors.

Each of the foregoing methods may further include determining individual activities of a plurality of nucleic acid regulatory elements, wherein the plurality of nucleic acid regulatory elements includes regulatory elements that differ from the single regulatory element by one or more transversions or transpositions of stretches of nucleic acid sequences of greater than four nucleotides.

In another aspect, the invention features a method of determining individual activities of a plurality of nucleic acid regulatory elements. This method, in general, includes providing any of the foregoing populations of cells and determining the amount of the tags expressed in the cells; where the amount of each tag detected is an indication of the activity of a corresponding nucleic acid regulatory element.

In another aspect, the invention features a method of determining the relative differences of the individual activities of a plurality of nucleic acid regulatory elements between at least two populations of cells. These populations of cells can optionally be derived from two or more different donors or cell lines, be derived from the same population of cells at multiple time points, or be subjected to at least two experimental perturbations. This method, in general, includes providing any of the foregoing populations of cells and determining the amount of the tags expressed in the cells; where the relative differences in the amounts of each tag detected in two or more cell populations is an indication of the relative activity of a corresponding nucleic acid regulatory element in said populations.

In another aspect, the invention features a plurality of nucleic acid constructs including a plurality of distinct nucleic acid regulatory elements; where each of the constructs includes an identifying nucleic acid tag, an optional restriction enzyme site, and a corresponding nucleic acid regulatory element; and wherein the restriction enzyme site is located between the nucleic acid regulatory element and the tag. In these constructs, the tag can be optionally included upstream of the nucleic acid regulatory element. These constructs may also include an identical stretch of nucleotides located 3' to the identifying nucleic acid tag.

In another aspect, the invention features a method of determining individual activities of a plurality of nucleic acid regulatory elements. Here the method, in general, includes providing any of the foregoing plurality of nucleic acid constructs; inserting the nucleic acid constructs into expression vectors, where the resulting expression vectors each include at least one of the nucleic acid regulatory elements, at least one open reading frame, and at least one of the tags; introducing the resulting expression vectors into cells in which the open reading frames and the tags are expressed; and determining the amount of the tags expressed in the cells; wherein the amount of each tag detected is an indication of the activity of a corresponding nucleic acid regulatory element.

In another aspect, the invention features a method of identifying variants of a nucleic acid regulatory element that have higher individual activities than said regulatory element in one or more cell populations, or optionally higher relative differences in individual activities between two or more cell populations. Here the method, in general, includes providing any of the foregoing plurality of nucleic acid constructs, optionally including one or more copies of said regulatory element; inserting the nucleic acid constructs into expression vectors, where the resulting expression vectors each include at least one of the nucleic acid regulatory elements, at least one open reading frame, and at least one of the tags; introducing the resulting expression vectors into cells in which the open reading frames and the tags are expressed; determining the amount of the tags expressed in the cells; wherein the amount of each tag detected is an indication of the activity of a corresponding nucleic acid regulatory element, and optionally the relative differences in the amounts of each tag detected in two or more cell populations is an indication of the relative activity of a corresponding nucleic acid regulatory element in said populations; and identifying variants that have higher individual activities than said regulatory element in one or more cell populations, or optionally higher relative differences in individual activities between two or more cell populations, using, e.g., a statistical algorithm.

In yet another aspect, the invention features a kit for determining the individual activities of a plurality of nucleic acid regulatory elements; the kit including an expression vector, a restriction enzyme, a nucleic acid construct encoding an open reading frame, reaction buffers, and a set of instructions. Such instructions describe providing any of the foregoing plurality of nucleic acid constructs, inserting the nucleic acid constructs into the expression vector, where the resulting expression vectors each include at least one of the regulatory elements and at least one of the tags, and inserting the open reading frame into the expression vector. These kits may also include instructions for introducing the resulting expression vectors into cells in which the open reading frames and the tags are expressed; and determining the amount of the tags expressed in the cells; where the amount of each tag detected is an indication of the activity of a corresponding nucleic acid regulatory element. The foregoing kits may also include the cells into which the expression vectors are introduced.

In another aspect, the invention features a kit for determining the individual activities of a plurality of nucleic acid regulatory elements. The kit can include any of the plurality of expression vectors described herein, reaction buffers, and instructions for introducing the plurality of expression vectors into a population of cells and determining expression of the tags expressed in the cells, such that the amount of each tag detected is an indication of the activity of a corresponding nucleic acid regulatory element.

In another aspect, the invention features a kit for identifying variants of a nucleic acid regulatory element that have higher individual activities than said regulatory element in one or more cell populations, or optionally higher relative differences in individual activities between two or more cell populations. The kit can include any of the plurality of expression vectors described herein, reaction buffers, and instructions for introducing the plurality of expression vectors into one or more population of cells, determining expression of the tags expressed in the cells, such that the amount of each tag detected is an indication of the activity of a corresponding nucleic acid regulatory element, and optionally the relative differences in the amounts of each tag detected in two or more cell populations is an indication of the relative activity of a corresponding nucleic acid regulatory element in said populations; and identifying variants that have higher individual activities than said regulatory element in one or more cell populations, or optionally higher relative differences in individual activities between two or more cell populations, using, e.g., a statistical algorithm.

In another aspect, the invention features a system for determining individual activities of a plurality of nucleic acid regulatory elements. Such a system includes any of the foregoing populations of cells; reagents for isolating mRNA generated in the cells; reagents for performing first strand cDNA synthesis using the isolated mRNA as a template; and a sequencing apparatus, where a mixture of tagged transcripts may be analyzed in the same experiment by identifying populations of transcripts according to their tags.

In yet another aspect, the invention features a system for identifying variants of a nucleic acid regulatory element that have higher individual activities than said regulatory element in one or more cell populations, or optionally higher relative differences in individual activities between two or more cell populations. Such a system includes any of the foregoing pluralities of nucleic acid regulatory elements or populations of cells; reagents for isolating mRNA generated in the cells; reagents for performing first strand cDNA synthesis using the isolated mRNA as a template; and a sequencing apparatus, where a mixture of tagged transcripts may be analyzed in the same experiment by identifying populations of transcripts according to their tags.

By "plurality of expression vectors" is meant an undivided sample that contains one or more copies of at least two or more (e.g., 100, 500, 1000, 2000, 5000, 10000, or more) distinct expression vectors.

By "nucleic acid regulatory element" is meant a sequence of nucleotides which operates in part, or in whole, to regulate expression of a gene. Exemplary regulatory elements include, without limitation, promoters or cis-regulatory elements such as enhancers, silencers, boundary control elements, insulators, locus control regions, response elements, stabilizing elements, de-stabilizing elements and splicing elements. Such regulatory elements are, in general, but not without exceptions, located 5' to the coding sequence of the gene it controls, in an intron, or 3' to the coding sequence of a gene, either in the untranslated or untranscribed region.

By "activity of a nucleic acid regulatory element" is meant the amount of mRNA expression of an open reading frame resulting from the nucleic acid regulatory element being operatively connected to the open reading frame in the context of an expression vector. By "operatively connected" is meant that the nucleic acid regulatory element is oriented in an expression vector so as to influence the expression of the associated open reading frame.

By "nucleic acid construct" is meant an artificial (i.e., not naturally occurring) continuous sequence of nucleotides.

By "nucleic acid tag" is meant a short sequence of nucleotides (e.g., fewer than 40, 30, 25, 20, 15, 13, 12, 11, 10, 9, 8, 7, 6, 5, 4 or fewer nucleotides) included in an mRNA transcript that is unique to a particular expression vector (exclusive of the region encoding the nucleic acid tag) and/or a short sequence of nucleotides included in a nucleic acid construct that are unique to the nucleic acid construct (exclusive of the region encoding the nucleic acid tag).

By a tag "corresponding" to a particular nucleic acid element is meant that the tag is included on an mRNA sequence (or cDNA derived therefrom) that was generated under the control of the particular nucleic acid regulatory element. Because a tag "corresponds" to a particular nucleic acid regulatory element, it is possible to determine the expression vector (and, therefore, the nucleic acid regulatory element located on the identified expression vector) from which the tagged mRNA (or cDNA derived therefrom) was generated.

By "expression vector" is meant a nucleic acid that includes an open reading frame and, when introduced to a cell, contains all of the nucleic acid components necessary to allow mRNA expression of said open reading frame. "Expression vectors" of the invention also include elements necessary for replication and propagation of the vector in a host cell.

By "open reading frame" is meant a sequence of nucleotides that, when read in a particular frame, do not contain any stop codons over the stretch of the open reading frame.

By "determining the amount" is meant both an absolute quantification of a particular analyte (e.g., an mRNA sequence containing a particular tag) or a determination of the relative abundance of a particular analyte (e.g., an amount as compared to a mRNA sequence including a different tag). The phrase includes both direct or indirect measurements of abundance (e.g., individual mRNA transcripts may be quantified or the amount of amplification of an mRNA sequence under certain conditions for a certain period of time may be used a surrogate for individual transcript quantification) or both.

The invention described herein facilitates systematic screening, reverse engineering, and optimization of cis-regulatory elements at high resolution and scale. The methods integrate multiplexed DNA synthesis and sequencing technologies to generate and quantify the transcriptional regulatory activity of thousands of arbitrary DNA sequences in parallel in cell-based assays. Each assay may, e.g., be prepared and performed in a single tube (or a single experiment) and cell culture dish, making it simpler and more cost-effective than traditional "promoter/enhancer bashing" methods.

Other features and advantages of the invention will be apparent from the following detailed description, the drawings, and the claims.

BRIEF DESCRIPTION OF THE DRAWINGS

FIG. 4 discloses SEQ ID NOS: 17-19 respectively, in order of appearance.

FIG. 7 discloses SEQ ID NOS: 21-41, respectively, in order of appearance.

FIG. 16A discloses SEQ ID NOS: 20 and 42, respectively, in order of appearance.

FIG. 17A discloses SEQ ID NOS: 43-44, respectively, in order of appearance.

FIG. 18A discloses SEQ ID NOS: 20 and 42, respectively, in order of appearance.

FIG. 19A discloses SEQ ID NOS: 43-44, respectively, in order of appearance.

FIG. 20A discloses SEQ ID NOS: 20, 42 and 45-52, respectively, in order of appearance.

FIG. 20D discloses SEQ ID NOS: 43-44 and 53-56, respectively, in order of appearance.

DETAILED DESCRIPTION OF THE INVENTION

In general, the invention provides expression vectors, cells, constructs, kits, systems, and methods for determining qualitative or quantitative activities or both of a plurality of nucleic acid regulatory elements which have been distinctively tagged. Such activity of the tagged regulatory element is assayed at, e.g., the transcriptional level. The methods described herein facilitate, e.g., the systematic reverse engineering or optimization of cis-regulatory elements at high resolution and at a large scale. Exemplary cis-regulatory elements include, without limitation, elements functional in plants, bacteria, animals (e.g., humans), protists, and fungi. The methods further include integration of multiplexed DNA synthesis and sequencing technologies to generate and quantify the transcriptional regulatory activity of such cis-regulatory elements, e.g., thousands of arbitrary DNA sequences in parallel in cell-based assays (e.g., mammalian cell-based assays).

Figure 1A:
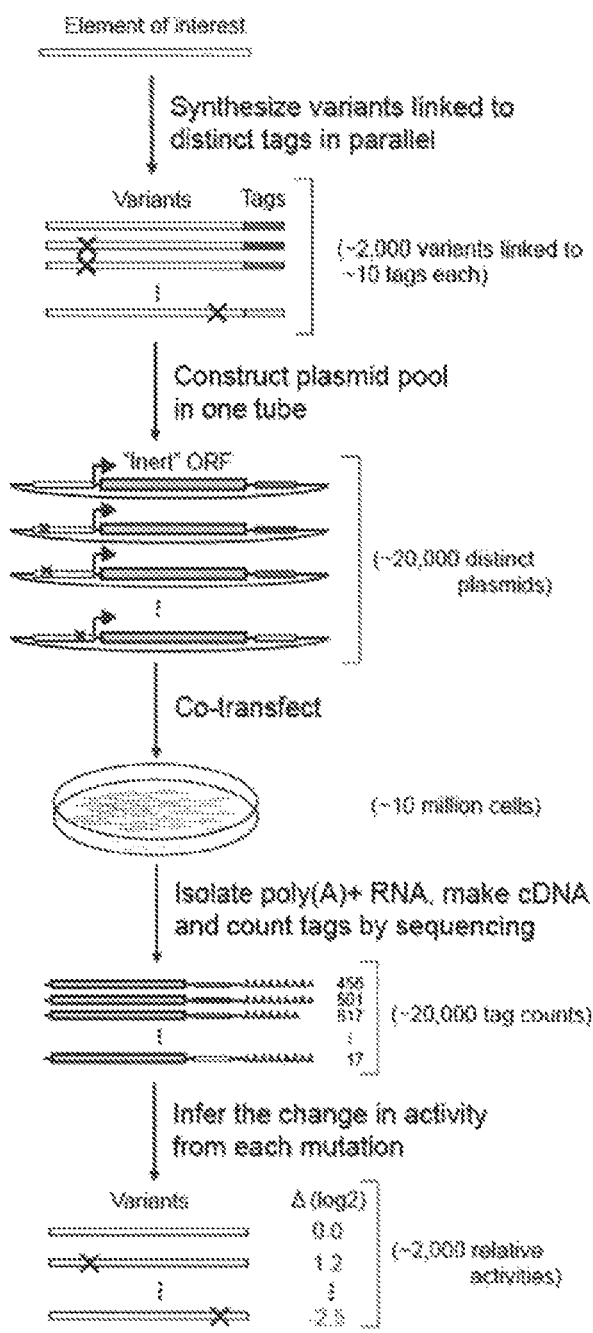
FIG. 1A is a schematic showing a multiplexed reporter assay.

An exemplary method is outlined in FIG. 1A. Briefly, tens of thousands of oligonucleotides encoding the regulatory element of interest, and a set of engineered variants, are obtained (e.g., by parallel synthesis on a microarray). Each variant is linked to one or more distinct tags, as well as several common restriction and/or primer sites that facilitate amplification and cloning. These variants are then PCR amplified and cloned in parallel into an arbitrary expression vector (e.g., a bacterial, yeast, or mammalian expression vector). A constant fragment containing an arbitrary open reading frame (ORF) (e.g., a fluorescent protein such as green fluorescent protein ("GFP") or luciferase) and optionally a promoter is then inserted between the regulatory elements and their associated tags. In some examples, distinct plasmids are maintained as an undivided single high complexity library.

To assay the relative transcriptional activities of the regulatory elements, the plasmids are co-transfected into a population of cultured cells. In some examples, cells containing plasmids, fragments of plasmids, or plasmid-derived viral or transposon vectors that have been stably integrated into the genome are selected based on drug resistance (e.g., puromycin resistance) or fluorescence (e.g., GFP expression). After optional perturbations of the cell population, the cells may be harvested for total RNA and/or poly(A)+ RNA isolation. Optionally, first strand cDNA synthesis may be performed and an cDNA library (e.g., an Illumina® cDNA library) may be generated using fusion PCR or ligation. Optionally, the cDNA synthesis may include addition of one or more distinct nucleic acid tags to all synthesized molecules that may serve to identify the cell population or sample from which the library was generated. The mRNA or cDNA containing individual tags may then be quantified (e.g., by quantitative sequencing, microarray hybridization, or bead hybridization) representing the relative abundances of mRNAs transcribed from each distinct reporter construct in the experiment. To normalize for differences in the relative concentrations of the transfected plasmids, similar tag counts may be generated by sequencing the plasmid pool or the all or part of the genomes of stable transfected cells. Finally, the relative activities of the various regulatory element variants may be inferred from the set of normalized tag counts using a statistical algorithm. For example, the activity of a single regulatory element variant linked to a single tag is first estimated by dividing the sequence count or hybridization signal of the tag in the mRNA or cDNA sample to the corresponding sequence count or hybridization signal of the same tag in the corresponding plasmid pool. If the plasmid pool contains multiple distinct constructs that link the same regulatory element variant to different tags, a more accurate estimate of the activity of the element may optionally be obtained by computing a summary statistic (e.g., the median or mean) of the mRNA or cDNA to plasmid ratios obtained for each individual tag. The relative activities of each distinct regulatory element may then be inferred by comparing these normalized sequence count or hybridization signals.

Figure 1B:
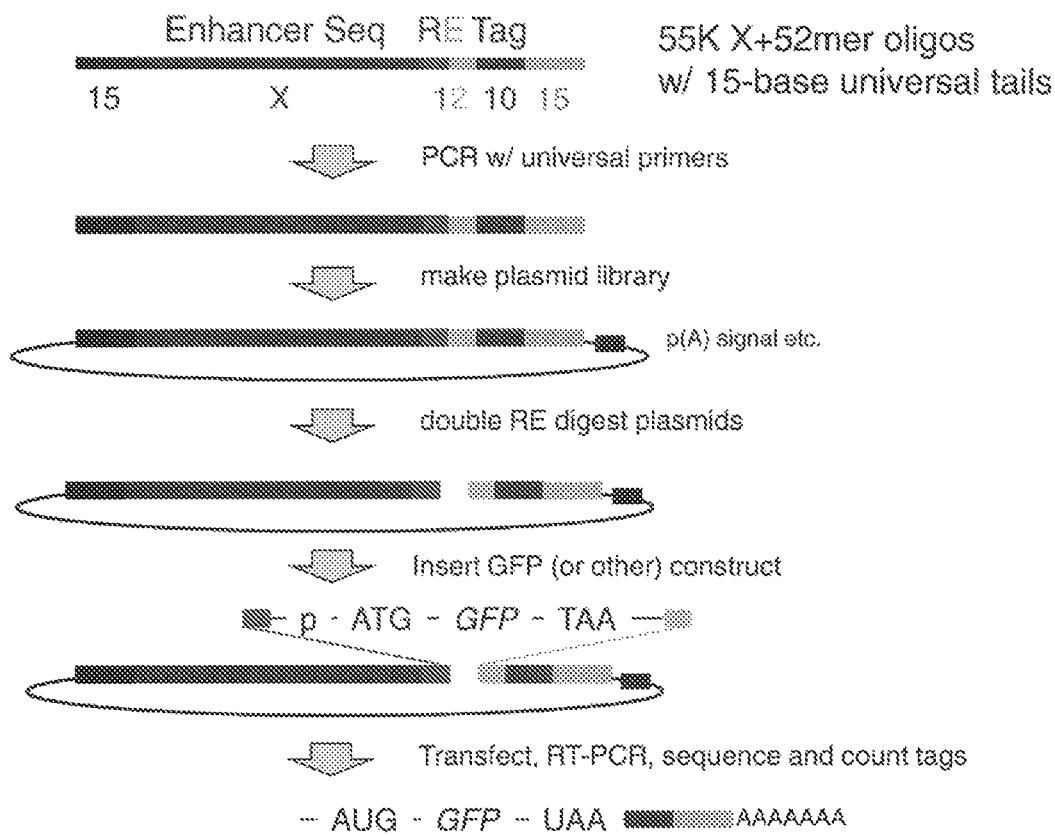
FIG. 1B is a schematic showing a method for constructing a library of nucleic acid constructs containing a plurality of nucleic acid regulatory elements.

Another exemplary method is outlined in FIG. 1B. Briefly, nucleic acid constructs including restriction enzyme sites ("R" and "E"), a tag, and 15 base universal tails are engineered. The construct is amplified using PCR and universal primers. The resultant construct mixture is then inserted into an expression vector generating a plasmid library. The plasmids are digested and an ORF (e.g., a sequence encoding a GFP) is inserted into the expression vector. The plasmids are then transfected into a cell population, first strand cDNA synthesis is then performed, and the tags are quantified according to standard methods, e.g., quantitative sequencing protocols.

Figure 1C:
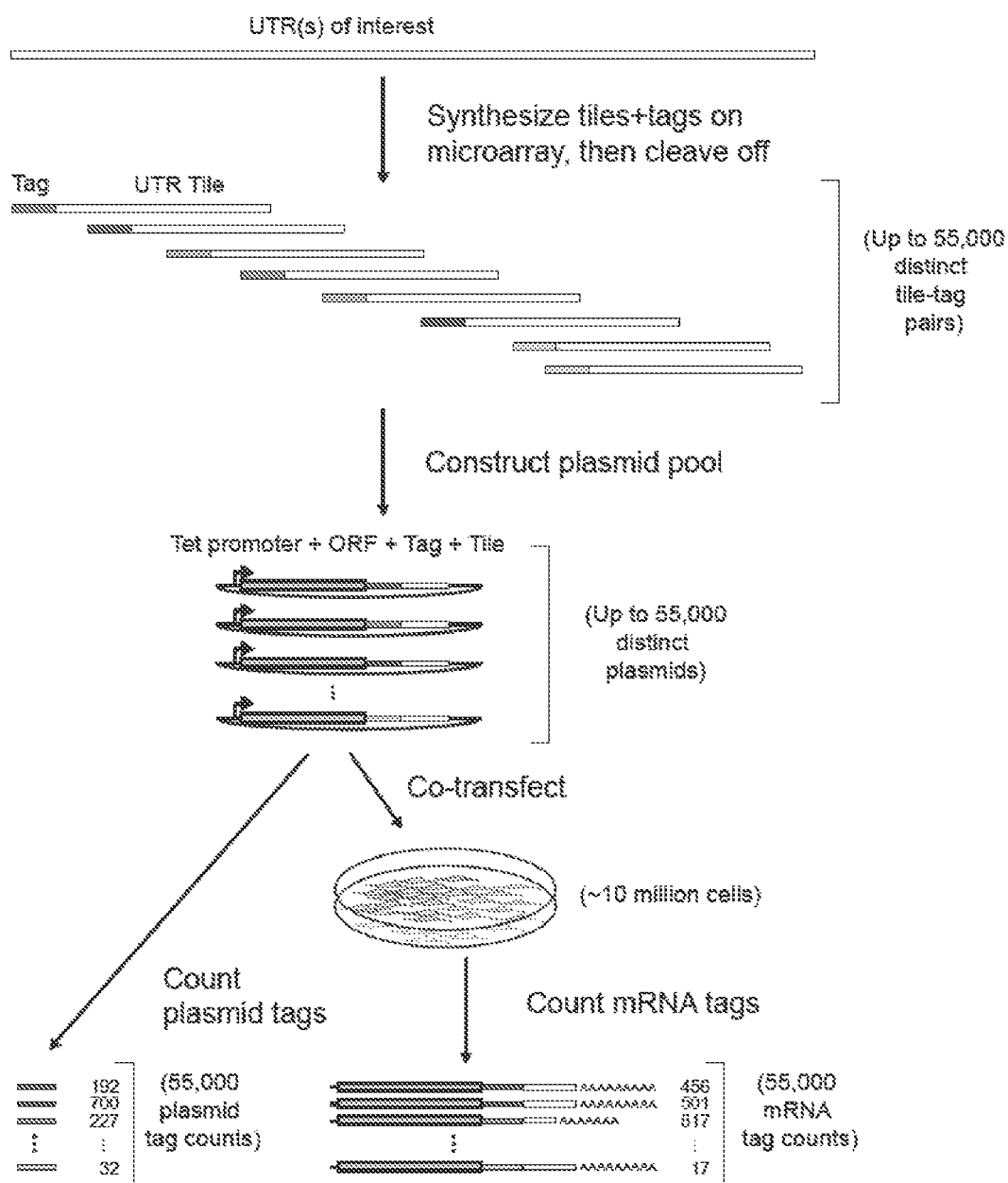
FIG. 1C is a schematic showing a multiplexed reporter assay.

Another exemplary method is illustrated in FIG. 1C. Briefly, tens of thousands of oligonucleotides encoding a tag followed by a regulatory element of interest, and a set of engineered variants, are obtained (e.g., by parallel synthesis on a microarray). Each variant is linked to one or more distinct tags. These variants are then, e.g., PCR amplified and cloned in parallel into an arbitrary expression vector (e.g., a bacterial, yeast, or mammalian expression vector) downstream of an arbitrary ORF (e.g., a fluorescent protein such as GFP or luciferase) (the ORF optionally being downstream of an additional regulatory element). In some examples, distinct plasmids are maintained as an undivided single high complexity library. The relative transcriptional activities of the different expression vectors can be determined, e.g., as described above.

In yet another exemplary method, a short, very high-complexity tag pool (e.g., generated by degenerate column-based oligonucleotide synthesis) is cloned into a reporter background (e.g., an expression vector containing an arbitrary ORF). Various regulatory elements are then cloned into the tagged plasmid pool. The various regulatory elements can be generated, e.g., by multiplexed PCR, error-prone PCR, or shearing/digestion of genomic DNA. Variant-tag links can be established by pair-end sequencing of the resultant pool or by digestion of the plasmid library to remove all or a portion of the nucleotides between the regulatory element and tags, followed by sequencing. The relative transcriptional activities of the different expression vectors can be determined, e.g., as described above.

Nucleic acid constructs are generated by any means known in the art, including through the use of polymerases and solid state nucleic acid synthesis (e.g., on a column, multiwall plate, or microarray). Furthermore, a plurality of nucleic acid constructs may be generated by first generating a parent population of constructs (e.g., as described above)

and then diversifying the parent constructs (e.g., through a process by which parent nucleotides are substituted, inserted, or deleted) resulting in a diverse population of new nucleic acid constructs. The diversification process may take place, e.g., within an isolated population of nucleic acid constructs with the nucleic acid regulatory element and tag in the context of an expression vector, where the expression vector also contains an open reading frame operatively connected to the nucleic acid regulatory element.

The nucleic acid regulatory elements may be naturally-occurring sequences, variants based on the naturally-occurring sequences, or wholly synthetic sequences. The source of the nucleic acid regulatory element is not critical. Variants include those developed by single (or greater) nucleotide scanning mutagenesis (e.g., resulting in a population of nucleic acid regulatory elements containing single mutations at each nucleotide contained in the naturally-occurring regulatory element), transpositions, transversions, insertions, deletions, or any combination thereof. The nucleic acid regulatory elements may include non-functional sequences (e.g., sequences that create space between nucleic acid regulatory subunits but do not themselves contribute any sequence specific effect on the regulatory element's activity). In other embodiments, the regulatory element is entirely arbitrary, and genetic reporter constructs are constructed that link such arbitrary DNA elements to distinguishing tags as described below.

The invention provides for the inclusion of nucleic acid tags to facilitate the determination of the activity of specific nucleic acid regulatory elements. These tags are included in the nucleic acid constructs and expression vectors containing the nucleic acid regulatory elements. Each tag is unique to the corresponding nucleic acid regulatory element (i.e., although a particular nucleic acid regulatory element may have more than one tag (e.g., 2, 3, 4, 5, 10, or more), each tag is indicative of a single nucleic acid regulatory element). These tags are oriented in the expression vector such that they are transcribed in the same mRNA transcript as the associated open reading frame. The tags may be oriented in the mRNA transcript 5' to the open reading frame, 3' to the open reading frame, immediately 5' to the terminal poly-A tail, or somewhere in-between.

The nucleic acid tags may be greater than 4 (e.g., greater than 10) nucleotides in length and/or fewer than 40, 30, 25, 20, 15, 13, 12, 11, 10, 9, 8, 7, 6, 5, or 4 nucleotides in length (e.g., the tags may be 5, 6, 7, 8, 9, 10, 11, 12, 13, 14, or 15 nucleotides in length). The unique portions of the nucleic acid tags may be continuous along the length of the tag sequence or the tag may include stretches of nucleic acid sequence that is not unique to any one tag. In one application, the unique portions of the tags may be separated by a stretch of nucleic acids that is removed by the cellular machinery during transcription into mRNA (e.g., an intron).

The expression vectors include a nucleic acid regulatory element, an open reading frame, and a nucleic acid tag. These elements may be arranged in a variety of configurations. For example, the nucleic acid regulatory element may be 5', 3', or within the open reading frame. The nucleic acid tag may be located anywhere within the region to be transcribed into mRNA (e.g., upstream of the open reading frame, downstream of the open reading frame, or within the open reading frame). Importantly, the tag is located 5' to the transcription termination site. The expression vectors may also include additional elements (e.g., invariant promoter elements (e.g., a minimal mammalian TATA box promoter or a synthetic inducible promoter), invariant or low complexity regions suitable for priming first strand cDNA synthesis (e.g., located 3' of the nucleic acid tag), elements to aid in isolation of transcribed RNA, elements that increase or decrease mRNA transcription efficiency (e.g., chimeric introns) stability (e.g., stop codons), regions encoding a poly-adenylation signal (or other transcriptional terminator), and regions that facilitate stable integration into the cellular genome (e.g., drug resistance genes or sequences derived from lentivirus or transposons).

The plurality of expression vectors includes an undivided sample containing one or more copies of at least two or more (e.g., 100, 500, 1000, 2000, 5000, 10000, or more) distinct expression vectors. Each distinct expression vector in the plurality of expression vectors differs from the remaining expression vectors by the inclusion of an identifying nucleic acid tag and, optionally, a distinct nucleic acid regulatory element. For example, each expression vector may share any or all of the following: one or more open reading frames, one or more invariant promoter element (e.g., a minimal mammalian TATA box promoter), one or more invariant or low complexity regions suitable for priming first strand cDNA synthesis (e.g., located 5' or 3' of the nucleic acid tag), one or more elements to aid in isolation of transcribed RNA, one or more elements that increase or decrease mRNA transcription efficiency (e.g., chimeric introns) or stability (e.g., stop codons), regions encoding a poly-adenylation signal (or other transcriptional terminator), and regions that facilitate stable integration into the cellular genome (e.g., drug resistance genes or sequences derived from lentivirus or transposons) The regulatory elements and tags of the plurality of expression vectors may differ from each other, e.g., as described herein.

The tags are quantified by methods known in the art, including quantitative sequencing (e.g., using an Illumina® sequencer) or quantitative hybridization techniques (e.g., microarray hybridization technology or using a Luminex® bead system).

The invention provides multiple rounds of reporter assays to be performed where the variant sequences tested in one round are designed based on information gleaned from the previous round. Therefore, the invention also provides a strategy for systematically reverse engineering cis-regulatory elements and for iteratively developing and refining novel synthetic cis-regulatory elements.

Figure 2:
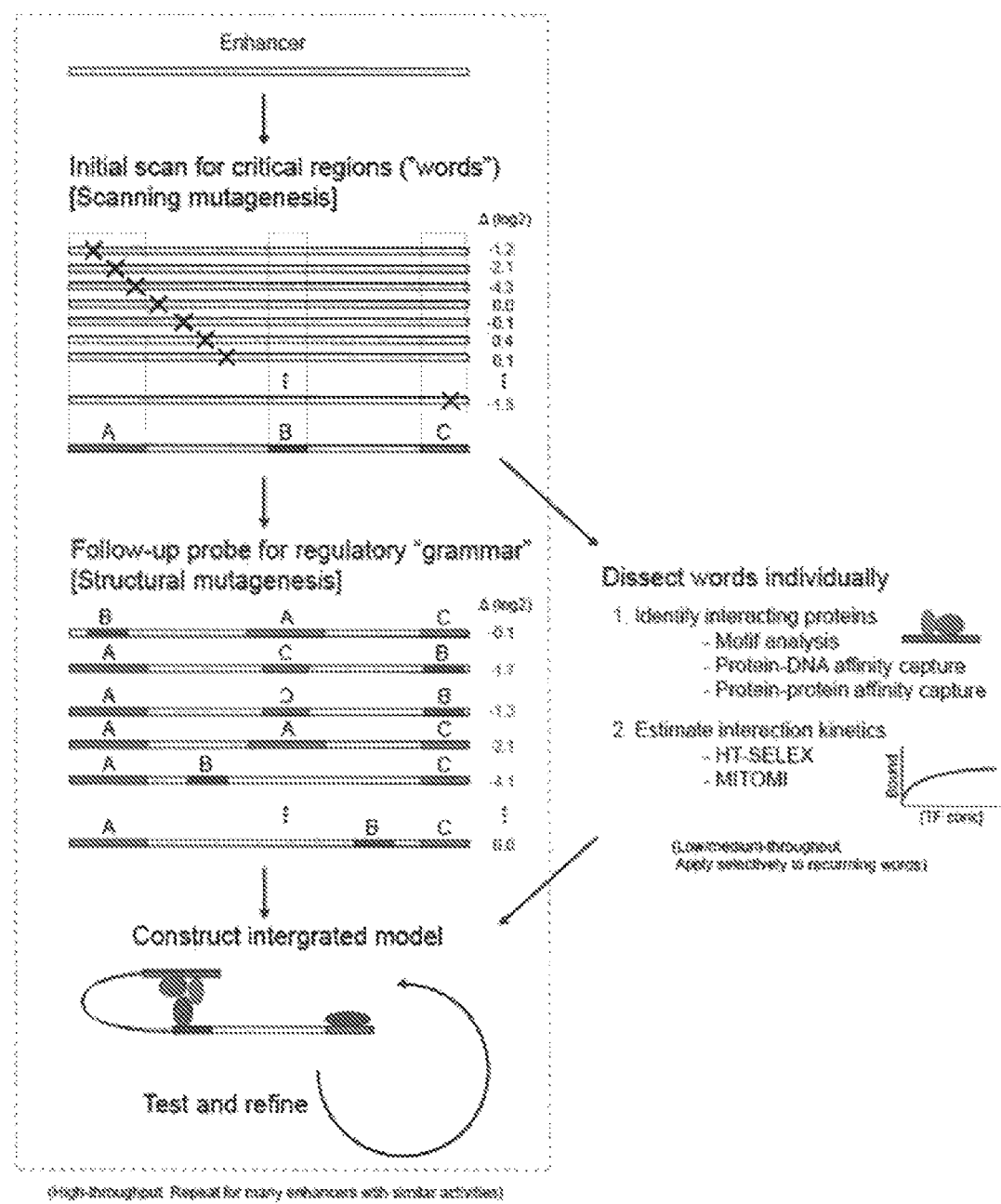
FIG. 2 is a schematic showing a strategy for reverse engineering cis-regulatory elements.

An example of such a method is depicted in FIG. 2. First, a regulatory element of interest is systematically mutated at every position to reveal the location of subsequences that are critical for the activity of the element. The method may also include identifying regulatory subsequences by mutating multiple consecutive nucleotides in each variant, thereby uncovering weak binding sites. Second, a new series of variants may then be synthesized to probe for constraints on the relative spacing, order, and orientation of the identified regulatory subsequences. The data from these two rounds may be used to develop a qualitative model of the regulatory element. Additional rounds of assays may then be performed to iteratively test and refine the model. This method may be applied to study a large number of distinct regulatory elements in parallel. In order to construct physical models of the regulatory element, the biochemical properties and protein-DNA interactions of the critical subsequences identified in this assay may be further studied using standard methods for studying individual protein-DNA interactions, such as high-throughput systematic evolution of ligands by exponential evolution enrichment (HT-SELEX) and mechanically induced trapping of molecular interactions (MITOMI).

The invention also provides kits for performing the methods of the invention. Such kits may include expression vectors, cells, nucleic acid constructs containing open reading frames, restriction enzymes, reaction buffers, and instructions for performing the methods described herein.

The invention also provides systems for performing the methods of the invention. Such systems include combinations of the following: populations of the above-described cells, reagents for isolating mRNA generated from such a population of cells, reagents for performing first strand cDNA synthesis using the isolated mRNA as a template, and a device for quantitatively sequencing the cDNA products.

Experimental Results

To test the multiplexed reporter assay, a classic adipose-specific enhancer located upstream of the murine-Fabp4 gene (also known as aP2) has been studies as follows. A 185 bp fragment from this enhancer has been shown to drive adipocyte-specific expression from heterologous promoters in cultured cells and in vivo. At least five distinct protein binding sites, two of which were found to recruit heterodimeric complexes consisting of PPAR gamma (PPARG) and RXR alpha (RXRA), have been described in this enhancer.

In the following experiments, a set of 1,789 variants of the mFapb4 enhancer were designed that combined aspects of both scanning and structural mutagenesis. The variants included: (i) single nucleotide substitutions at every position into every alternative nucleotide, (ii) complementation, or (iii) reverse complementation of all nucleotides to the right or left of every nucleotide position along the element, (iv) scrambling or (v) permutation of every possible subset of the five known protein binding sites, (vi) sliding each of the binding sites to the right or left of their wild-type position, and several other types of mutations. Each enhancer variant was linked to seven different 10 base-pair tags, as well as to universal primer and restriction sites as described above, resulting in 12,586 distinct 240mer oligonucleotide sequences. These sequences were synthesized, PCR amplified, and cloned into a basic plasmid backbone. The resulting plasmid pool was transfected into adipocytes derived from the murine 3T3-L1 cell line. Tagged mRNAs transcribed from the co-transfected plasmids were isolated and analyzed as described herein.

To evaluate the robustness and reproducibility of the assay, the plasmid construction and transfection were twice performed in independent, back-to-back experiments, and the results of each experiment compared. Sequencing the two plasmid pools (prior to transfection) to a depth of ~25 million reads each detected the presence of the vast majority (90-92%) of the desired constructs at fairly similar relative concentrations (coefficient of variation=0.3-0.4) in both pools. This indicates successful generation of high complexity plasmid pools. Comparison of the normalized mRNA tag counts obtained after transfection and sequencing revealed highly similar transcriptional activity estimates across all 1,789 variants in both replicates ($r^2$=0.89, $p<10^{-100}$). This indicates that the assay is robust and yields reproducible data.

Figure 3:
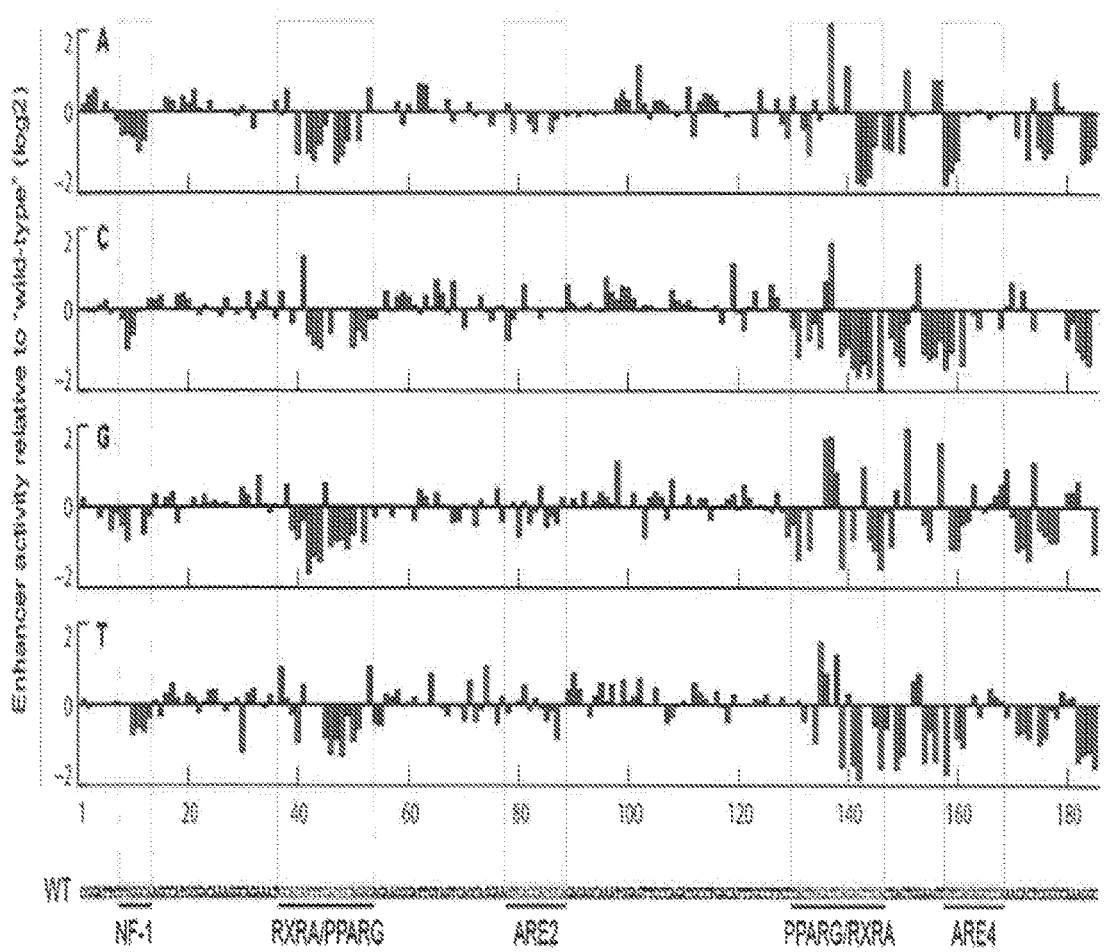
FIG. 3 is a series of graphs showing enhancer activity relative to "wild-type" of mFabp4 enhancers containing point mutations at each position along the 185 bp mFabp4 enhancer sequence (SEQ ID NO: 17) as indicated.

FIG. 3 summarizes data from 555 of the co-transfected variants that together contain every possible single nucleotide substitution. The wild-type Fabp4 enhancer sequence is shown at the bottom with the five known protein binding sites highlighted. PPARG/RXRA heterodimers are recruited to two binding sites in an adipogenesis-dependent manner. Both sites contain imperfect matches to the ~17 bp PPARG/RXRA consensus motif, which contains two direct repeats of the hexamer AGGTCA, separated by one nucleotide. PPARG is known to always bind to the 5' half-site of this repeat, which implies that the two sites in this enhancer are bound in opposite directions. A third binding site recruits nuclear factor I (NF-I). The remaining two sites (ARE2/ARE4) show affinity for an unknown protein complex that are present in both pre-adipocytes and adipocytes. The four bar plots show the change in transcriptional activities caused by substituting in the corresponding nucleotide at each position along the 185 bp sequence. A light gray bar indicates a statistically-significant change (at $p<0.01$).

Strikingly, many substitutions within the known NF-1 and PPARG/RXRA binding sites affect the activity of the enhancer, while most substitutions outside of known binding sites do not. Most functional substitutions lead to a decrease in activity, although substitutions within a small region of the 3' PPARG/RXRA site may increase the activity up to 4-fold over the wild-type. Close inspection revealed that the latter substitutions made the site more similar to the PPRG/RXRA consensus motif, suggesting that the wild-type site was not selected for maximal activity in adipocytes. Substitutions in the 5' half of ARE4 also lead to decreased activity, while substitutions in ARE2 appear to have relatively small effects in this experiment. Substitutions between the 3' PPARG/RXR site and ARE4, and at the extreme 3' end of the enhancer also reduced the enhancer activity. This might reflect the presence of previously unrecognized protein-DNA interactions in this region.

Figure 4:
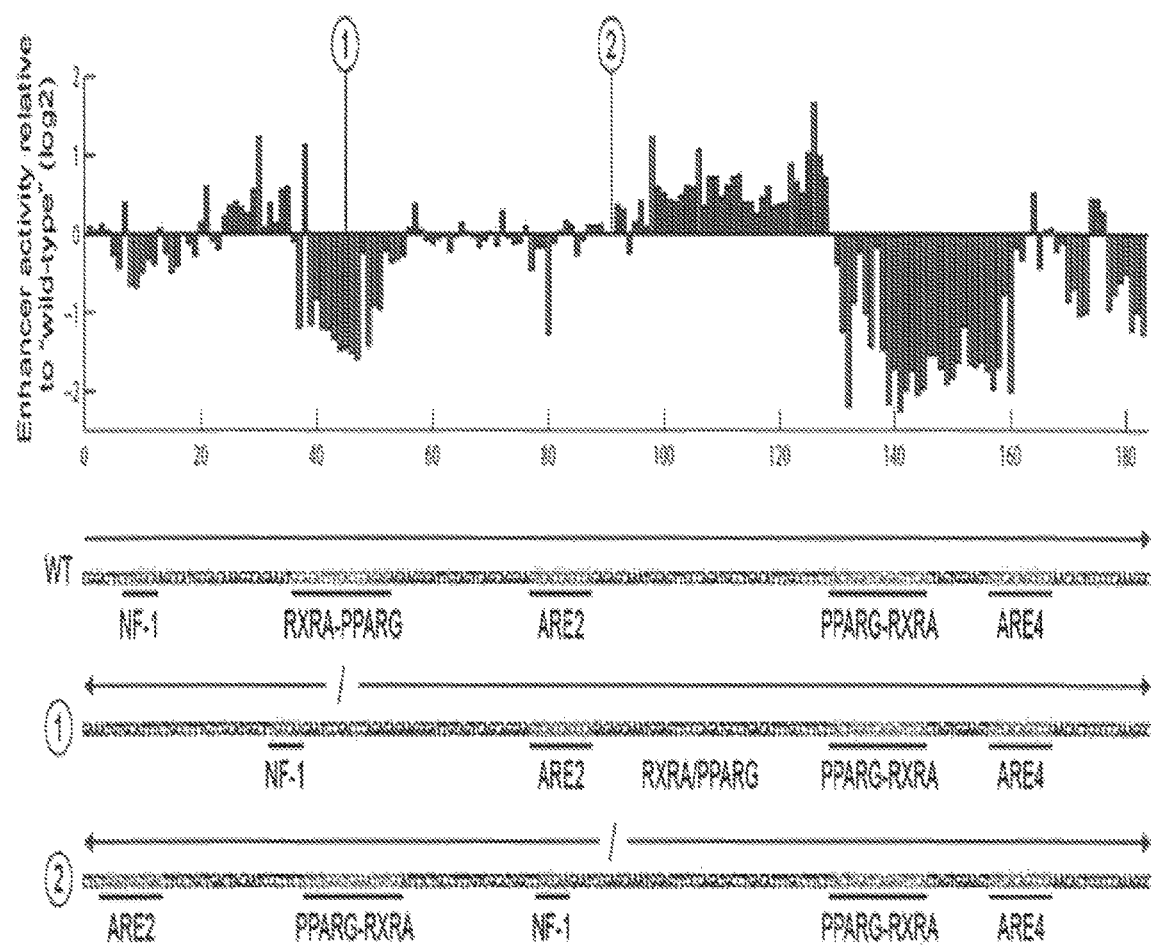
FIG. 4 is a graph showing enhancer activity relative to "wild-type" of mFabp4 enhancers in view of reverse complementing the 5' position of the enhancer.

FIG. 4 summarizes data from 183 other variants that together examine the effects of inverting (reverse complementing) the 5' side of the enhancer, with a breakpoint between any two adjoining nucleotides. The format is similar to FIG. 3, except that, in this case, each bar shows the change in transcriptional activity caused by inverting the sequence on the 5' side of the corresponding nucleotide position. This type of mutation has two effects: (1) it changes the relative ordering and orientation of protein binding sites on opposite sides of the breakpoint, and (2) it disrupts any binding site or other functional sequence that spans the breakpoint.

Example 1 highlights the result of inverting nucleotides 1-45. Because its breakpoint disrupts one of the PPARG/RXR binding sites, it leads to a significant decrease in the overall activity of the enhancer. In contrast, Example 2 shows that inverting nucleotides 1-91 does not lead to a significant change in activity. Thus, the relative ordering of ARE2, the first PPARG/RXRA site and the NF-I site is not important. This example also suggests that it does not matter whether the two PPARG/RXRA heterodimers bind the enhancer in the same or opposite directions.

In summary, this experiment clearly demonstrates the feasibility and potential of the above-described methodologies. In a single experiment, the total number of characterized mutants of the Fabp4 enhancer was increased by almost two orders of magnitude. The data confirm that the known NF-I and PPARG/RXRA binding sites are major contributors to the enhancer activity of the isolated 185 bp sequence, but also suggest the presence of additional functional sites. Moreover, the data show that the enhancer activity is relatively insensitive to the exact spacing and orientation of these sites.

In a second test of the multiplexed reporter assay, a synthetic cyclic AMP response element (CRE) has been studies as follows. This 87 bp fragment has been shown to drive dose-dependent expression from a minimal mammalian TATA-box promoter in cultured cells in response to stimuli that increase cyclic AMP levels within the cells. The fragment contains four binding sites for CREB proteins derived from natural DNA sequences assembled in an arbitrary order. This type of cis-regulatory element is frequently used to drive the expression of genetic reporters in studies of cell signaling and in high-throughput drug screening applications.

In the following experiments, a set of 27,000 variants of the CRE were designed by randomly substituting one or more nucleotides in the original element with alternative nucleotides. Each CRE variant was linked to a single 10 base-pair tag, as well as a universal primer and restriction sites as described above, resulting in 27,000 distinct 142mer oligonucleotide sequences. These sequences were synthesized, PCR amplified, and cloned into a basic plasmid backbone. A minimal TATA-box promoter and a firefly luciferase gene were then inserted between the CRE variants and the tags. The resulting plasmid pool was transfected into cells from the human HEK293 cell line. Twenty four hours later, the transfected cells were stimulated with 100 micromolar forskolin dissolved in DMSO, which is known to increase the cyclic AMP levels in cells. A transfected control population was treated with only DMSO. Tagged mRNAs transcribed from the co-transfected plasmids were isolated and analyzed as described herein.

Figure 5:
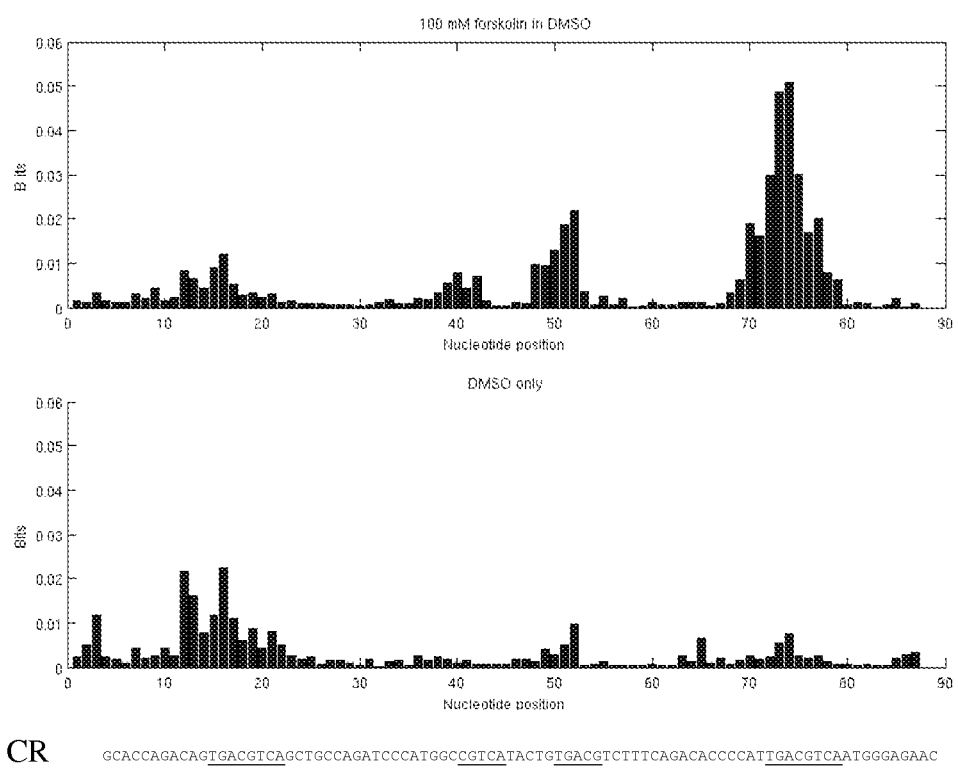
FIG. 5 is a graph showing the mutual information between the nucleotide present at each position along a synthetic 87 bp cyclic AMP response element (SEQ ID NO: 20) and the overall regulatory activity of the element.

FIG. 5 summarizes data from the combined activity measurements from all 27,000 CRE variants. The original synthetic CRE sequence is shown at the bottom with four known CREB protein binding sites underlined. The two bar plots show the mutual information (in bits) between the nucleotide at the corresponding position and the overall activity of the CRE in forskolin-stimulated (top) and control (bottom) cells, as calculated by standard methods. The higher the mutual information is at a position, the more important the corresponding nucleotide is for the activity of the element. Strikingly, the mutual information plots from the forskolin-treated cells show four clear peaks that closely correspond to the known CREB binding sites. The peaks are lower in the plots from the control cells, which is consistent with a lesser role for CREB in driving transcription from this element in the absence of increased cyclic AMP.

Figure 6:
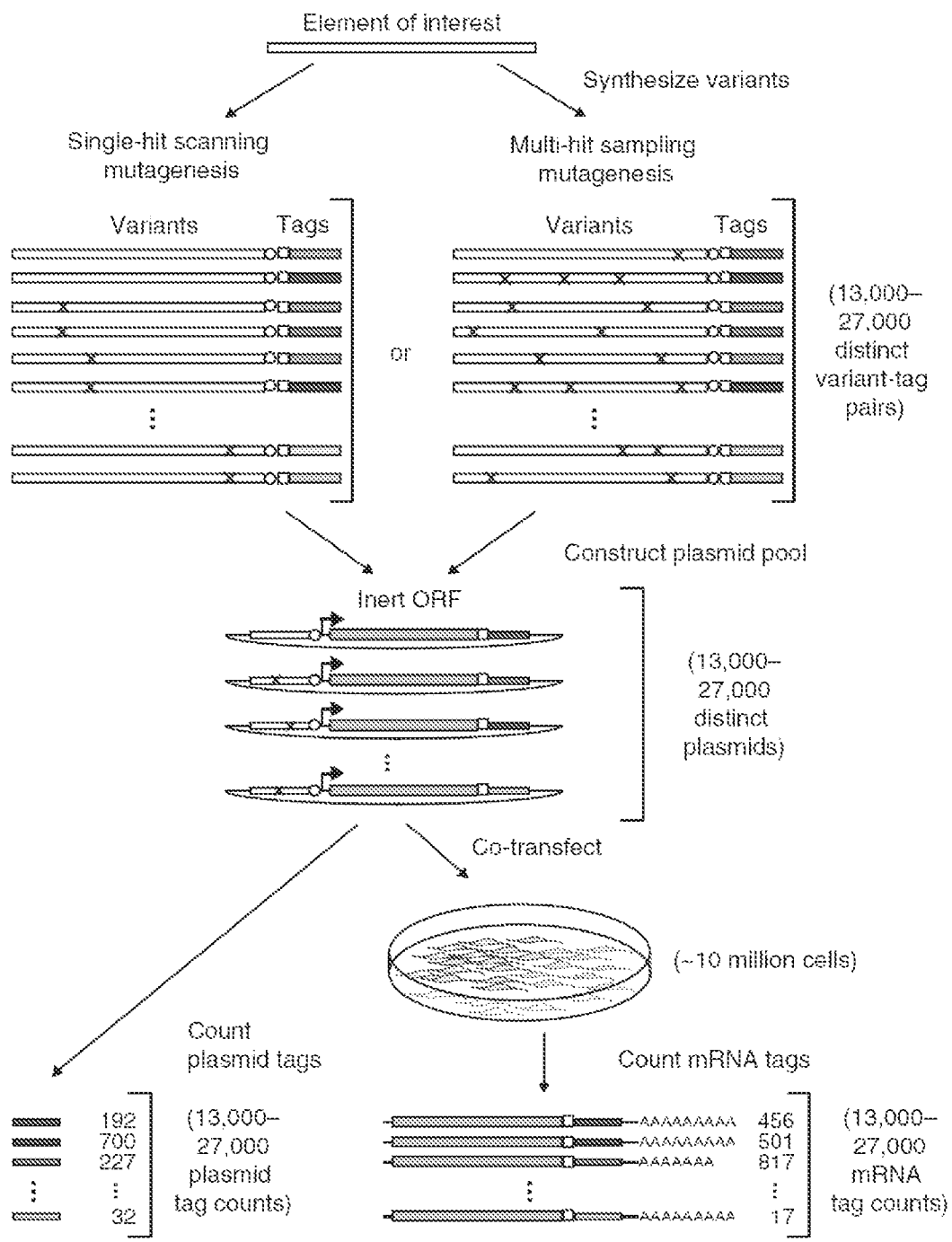
FIG. 6 is a schematic showing a comparison of various strategies of multiplex reporter assays (also referred to as massively parallel reporter assay or MPRA).

In another experiment, 142-mer oligonucleotide pools containing 87-nt CRE and INFB enhancer variants, as well as 10-nt tags and various invariant sequences required for cloning (FIG. 7), were synthesized. Two different mutagenesis strategies were tested (FIG. 6). The first was 'single-hit scanning' (Patwardhan, R. P. et al., *Nat. Biotechnol.* 27, 1173-1175, 2009) where we assayed ~1,000 specific enhancer variants, including all possible single substitutions, multiple series of consecutive substitutions and small insertions at all positions were assayed. Each scanning variant was linked to 13 tags for a total of 13,000 distinct enhancer-tag combinations. This redundancy provides parallel measurements for each variant, which can be used to both quantify and reduce the impact of experimental noise, including tag-dependent bias (FIG. 8). The second was 'multi-hit sampling' (Kinney et al., *Proc. Natl. Acad. Sci. USA.* 107, 9158-9163, 2010) where ~27,000 distinct enhancer variants, each linked to a single tag, were assayed. These variants were constructed by introducing random nucleotide substitutions into the enhancers at a rate of 10% per position. Because the variants were designed in silico and then synthesized, they provided a uniform mutational spectrum. This strategy is advantageous because each substitution is assayed in a larger fraction of the variants and the use of multiple substitutions enables detection of interactions; one disadvantage is that the measurements for individual variants are less accurate.

Figure 9:
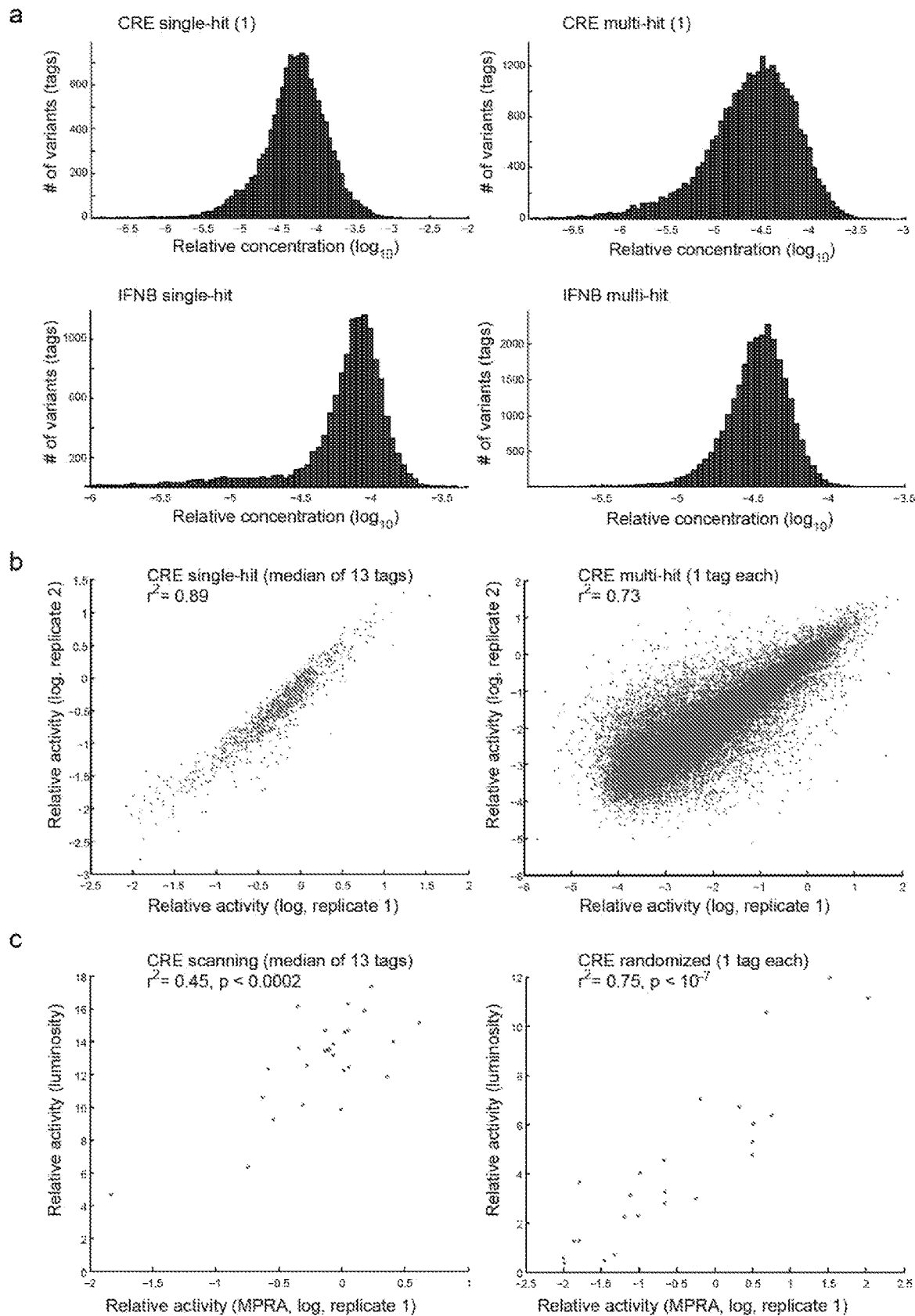
FIG. 9A is a series of histograms of the relative concentrations of the designed enhancer variants in each MPRA plasmid pool, as inferred by plasmid Tag-Seq.
FIG. 9B is a graph showing the concordance between CRE activity estimates from two independent MPRA experiments performed using each of the two mutagenesis designs.
FIG. 9C is a graph showing the concordance between luciferase-based assays and MPRA for 24 single-hit and multi-hit variants.

Oligonucleotide pools were synthesized according to both strategies and were cloned into identical plasmid backbones, a minimal TATA-box promoter was inserted, and a luciferase gene between the variants and tags was also inserted. The resulting plasmid pools were transfected into human embryonic kidney (HEK293T) cells. To induce the CRE or IFNB enhancer, the transfected cells were treated with forskolin or infected with Sendai virus, respectively. To estimate the relative activities of the enhancer variants, 20-120 million PCR-amplified mRNA and plasmid tags were sequenced from each transfection. The resulting data using several different approaches were validated as shown in FIG. 9.

First, the distributions of plasmid tag counts were examined. We found that the vast majority (≥99.6%) of the tags were indeed present in each pool, and that their relative concentrations were similar (coefficient of variation, 0.45-1.0). This confirmed that high-complexity plasmid pools were successfully generated.

The two CRE plasmid pools twice were synthesized and transfected twice. ~13,000 and ~27,000 pairs of mRNA-plasmid tag ratios obtained from the single- and multi-hit pools, respectively, were highly correlated (Pearson $r^2$=0.61 and 0.67, least significant $P<10^{-100}$). The medians of the 13 tag ratios from each distinct variant in the replicate single-hit pools were even more similar ($r^2$=0.89, $P<10^{-100}$). This indicated that the multiplexed reported assay was robust, and that the noise level can be controlled by adjusting the number of distinct tags linked to each distinct variant.

Finally, 24 plasmids were subcloned from each of two CRE pools and individually their luciferase expression levels after forskolin treatment were measured. A linear relationship exists between the multiplexed reporter assay- and luciferase-based activities for both pools ($r^2$=0.45 and 0.75, $P<0.0002$). This indicated that the multiplexed reporter assay was directly comparable to traditional reporter assays.

Next, scanning mutagenesis data were used to in an attempt to dissect the two induced enhancers. The relative activity of each variant was measured by comparing the median of its 13 mRNA/plasmid tag ratios to the median ratio for tags linked to the corresponding wild-type enhancer.

Figure 10:
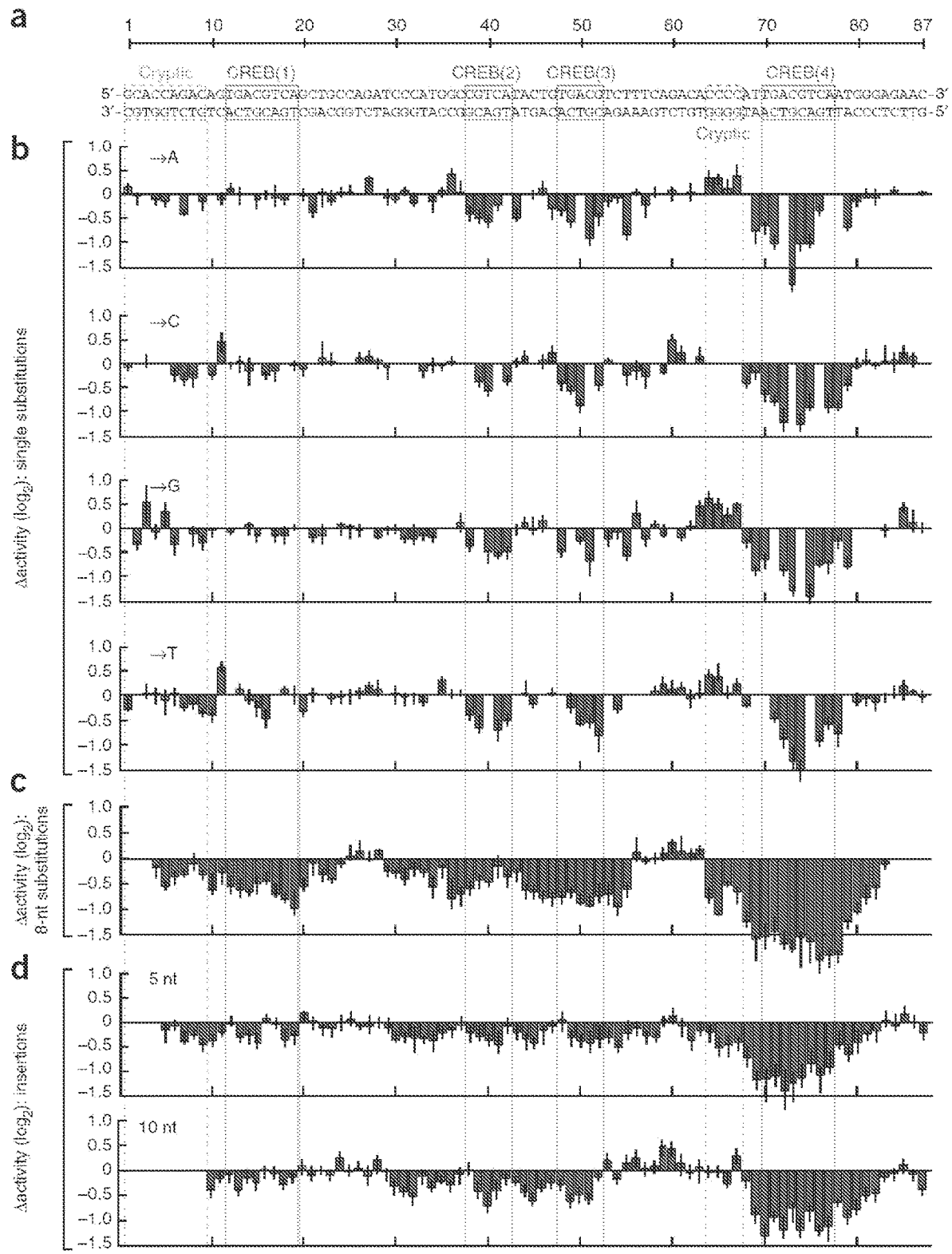
FIG. 10A shows the CRE sequence (SEQ ID NOS: 20 and 42, respectively, in order of appearance) with known and putative transcription factor binding sites indicated.
FIG. 10B is a graph showing the changes in induced activity owing to single-nucleotide substitutions. Each bar shows the log-ratio of the median variant and wild-type activity estimates.
FIG. 10C is a graph showing the changes in induced activity owing to eight consecutive substitutions. The plot shows the medians of three different types of substitutions (see also FIG. 11). Each bar is located at the fourth nucleotide in the corresponding 8-nt substitution.
FIG. 10D is a graph showing the changes in induced activity owing to 5-nt (top) and 10-nt (bottom) insertions. The plots show the means of two different insertions (see also FIG. 12). Each bar is located one nucleotide to the right of the insertion. Error bars show the first and third quartile.

The first focus was on the CRE, which contains two consensus CREB dimer binding sites (denoted as sites 1 and 4 in FIG. 10A) separated by two monomer sites (sites 2 and 3). 154 of the 261 possible single substitutions significantly altered its activity (5% FDR), with the majority (79%) resulting in decreased activity (FIG. 10B). The substitutions that resulted in the largest decreases were in or immediately flanking the CREB sites. Substitutions in the promoter-proximal CREB site 4 had the largest effects, which is consistent with reports of the cAMP responsiveness of CREB sites being inversely correlated with their distance from a TATA-box (Mayr et al., *Nat. Rev. Mol. Cell Biol.* 2, 599-609, 2001). Within the two dimer sites, substitutions in the central CGs were the most deleterious. This is consistent with biochemical data that show that this dinucleotide is critical for high-affinity CREB-DNA interactions (Benbrook et al., *Nucleic Acids Res.* 22, 1463-1469, 1994).

Substitutions at 47 of 61 positions outside of the CREB sites also caused significant (5% FDR), although generally more subtle, changes in activity. This may reflect the effects of cryptic non-CREB binding sites. In particular, two substitutions upstream of CREB site 1, as well as almost every substitution in a C-rich motif flanking CREB site 4, resulted in increased CRE activity. These substitutions may therefore cause either increased recruitment of activating factors or decreased recruitment of repressors.

Figure 11:
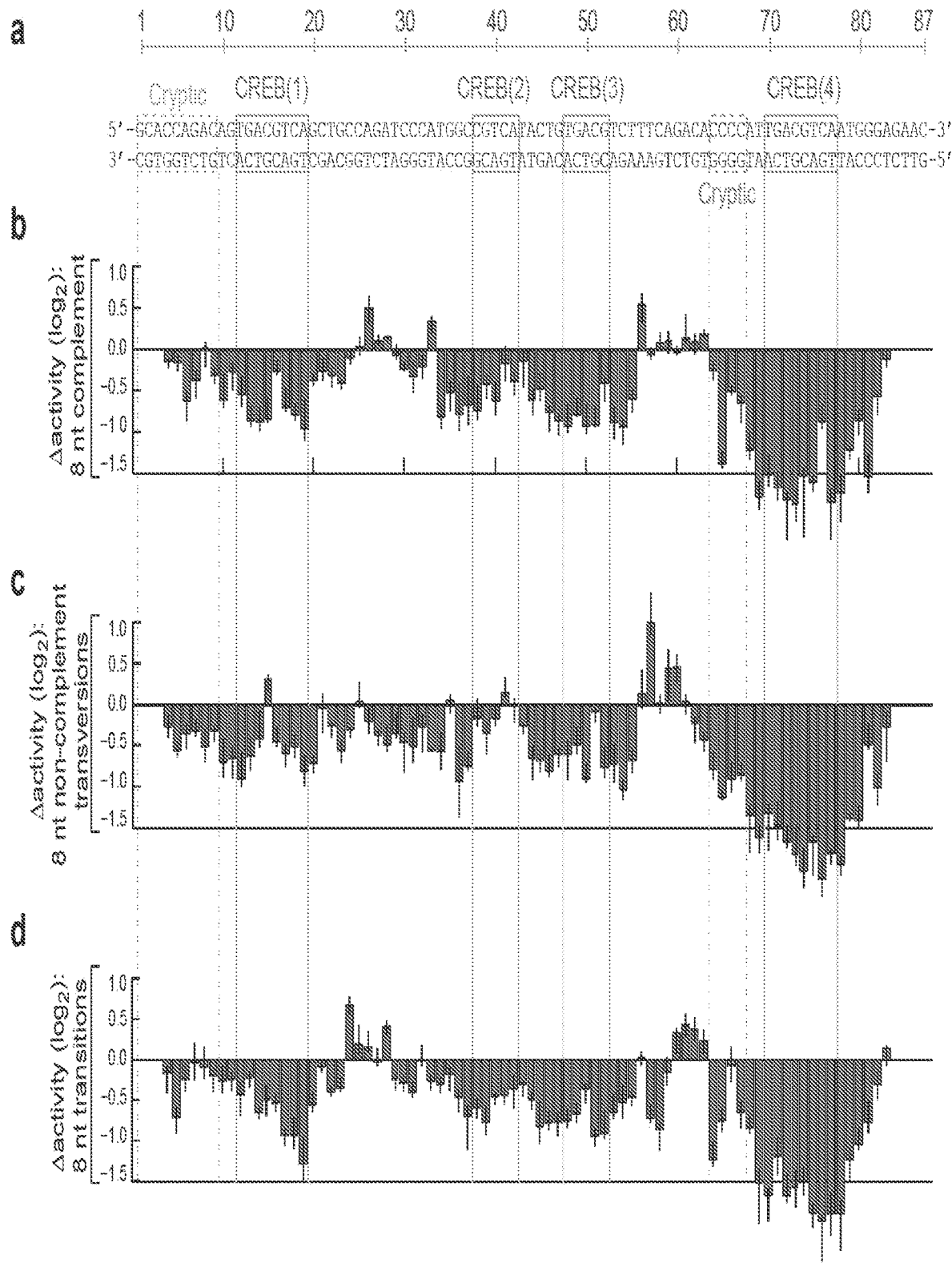
FIG. 11A shows the CRE sequence (SEQ ID NOS: 20 and 42, respectively, in order of appearance) with known and putative transcription factor binding sites indicated.
FIG. 11B is a graph showing the changes in induced activity due to 8 consecutive complement substitutions ($G \leftrightarrows C$, $A \leftrightarrows T$).
FIG. 11C is a graph showing the changes in induced activity due to 8 consecutive non-complement transversion substitutions ($G \leftrightarrows T$, $A \leftrightarrows C$).
FIG. 11D is a graph showing the changes in induced activity due to 8 consecutive transition substitutions ($G \leftrightarrows A$, $T \leftrightarrows C$). Each bar is located at the fourth nucleotide in the corresponding 8 nucleotide substitution. Error bars show the first and third quartiles.

Scanning the CRE with blocks of eight consecutive substitutions caused changes that were consistent with the single substitutions, but often more deleterious (FIG. 10C and FIG. 11). Notably, although most single substitutions in CREB site 1 had no detectable effects, the functional relevance of this site was clearly supported by the combined effect of multiple substitutions.

Figure 12:
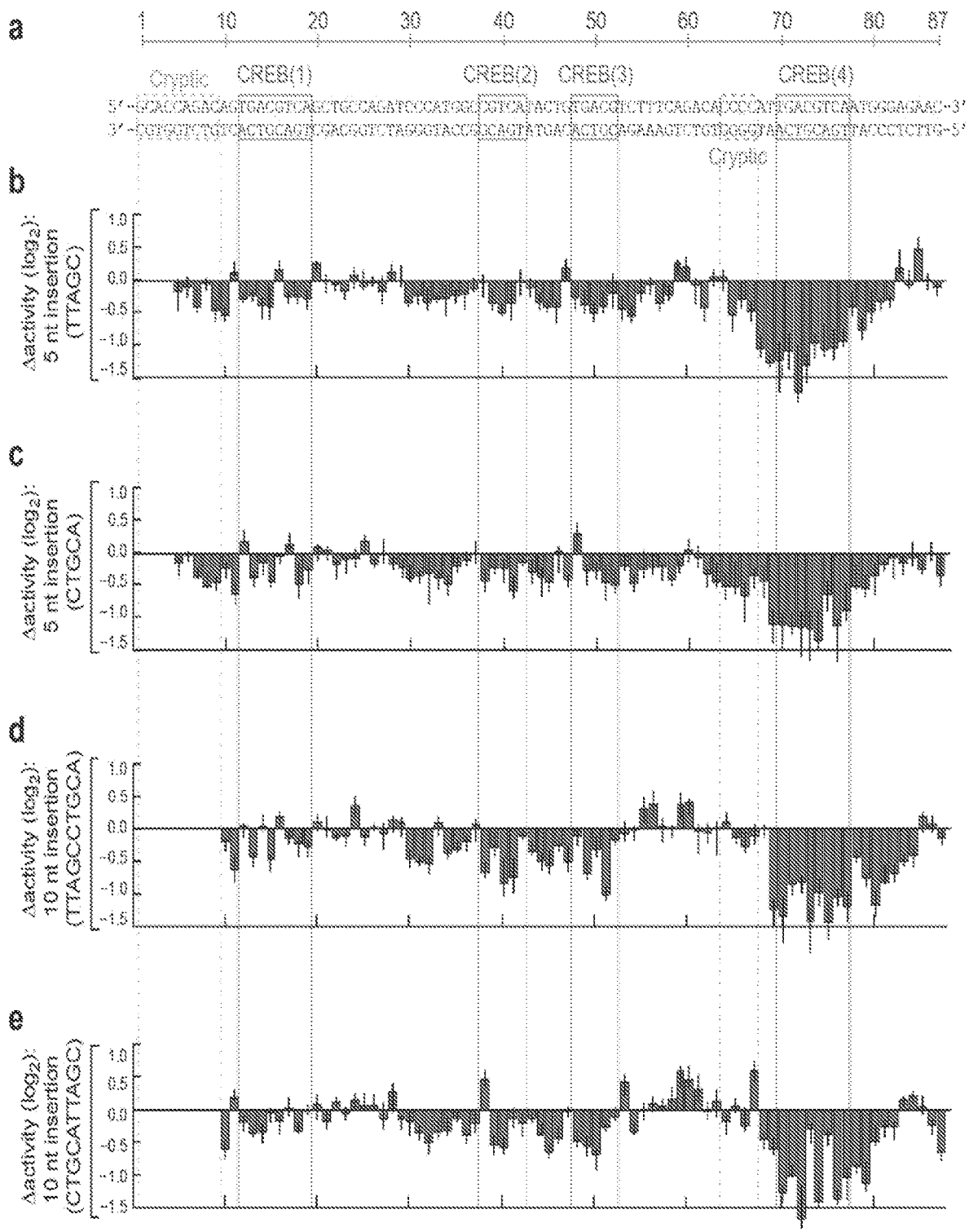
FIG. 12A shows the CRE sequence (SEQ ID NOS: 20 and 42, respectively, in order of appearance) with known and putative transcription factor binding sites indicated.
FIG. 12B is a graph showing the changes in induced activity due to insertion of TTAGC between each pair of consecutive nucleotides.
FIG. 12C is a graph showing the changes in induced activity due to insertion of CTGCA between each pair of consecutive nucleotides.
FIG. 12D is a graph showing the changes in induced activity due to insertion of TTAGCCTGCA (SEQ ID NO: 1) between each pair of consecutive nucleotides.
FIG. 12E is a graph showing the changes in induced activity due to insertion of CTGCATTAGC (SEQ ID NO: 2) between each pair of consecutive nucleotides. Each bar is located one nucleotide to the right of the insertion. Error bars show the first and third quartiles.

Insertions of both 5 and 10 nt were well-tolerated at multiple positions between CREB sites 1 and 2 and between sites 3 and 4 (FIG. 10D and FIG. 12). This implies that the CRE activity is not dependent on specific spacing or phasing between these sites. In contrast, insertions between sites 2 and 3 resulted in decreased activity, despite single substitutions having small effects in the same region. This may reflect a direct interaction between proteins at these two sites, which was also suggested by a study of these sites in their natural context (Fink et al., Proc. Natl. Acad. Sci. USA. 85, 6662-6666, 1988).

Figure 13:
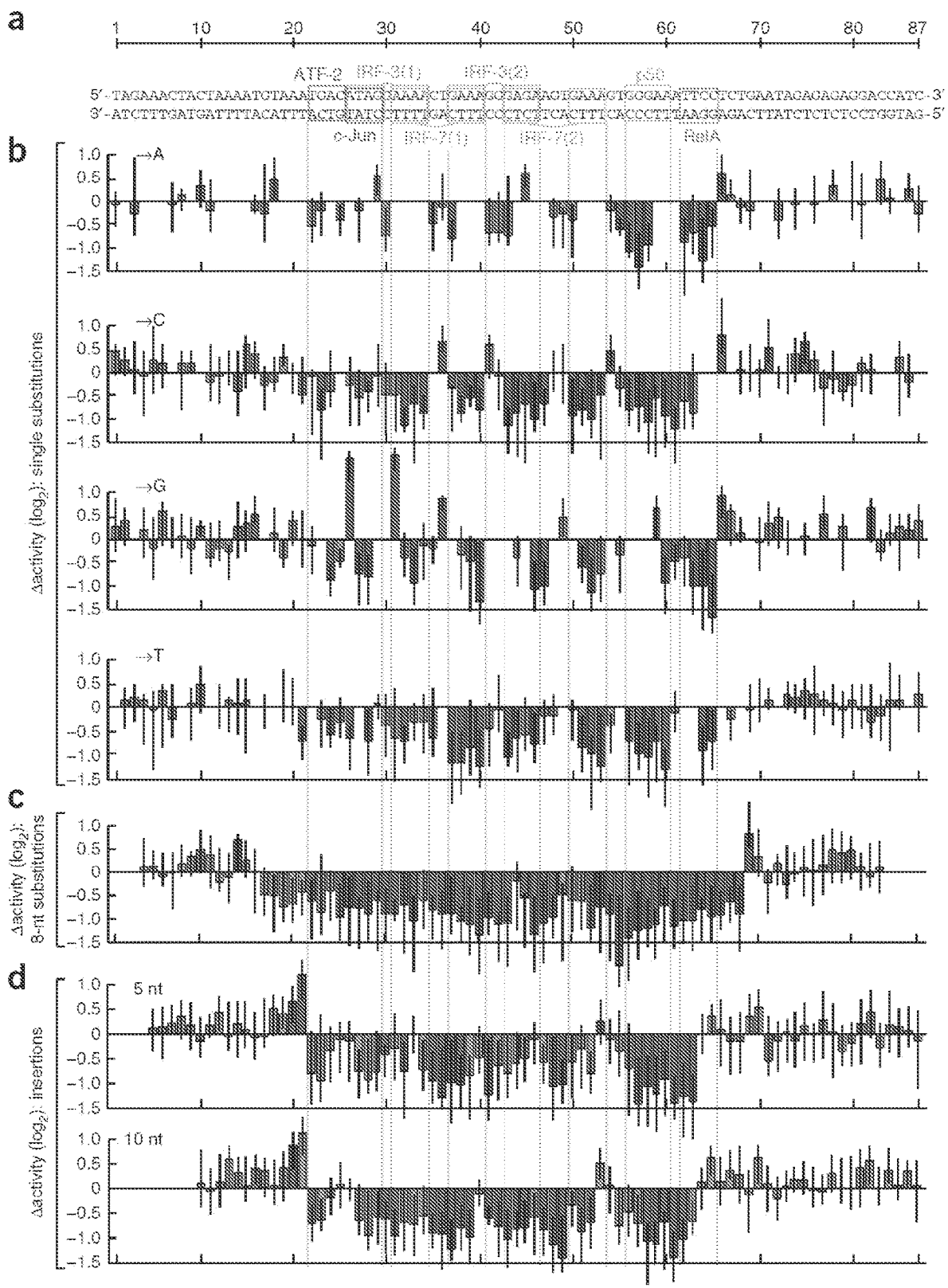
FIG. 13A shows the IFNB enhancer (SEQ ID NOS: 43-44, respectively, in order of appearance) with known transcription factor binding sites indicated.
FIG. 13B is a graph showing the changes in induced activity owing to single-nucleotide substitutions. Each bar shows the log-ratio of the median variant and wild-type activity estimates.
FIG. 13C is a graph showing the changes in induced activity owing to eight consecutive substitutions. The plot shows the medians of three different types of substitutions (see also FIG. 14). Each bar is located at the fourth nucleotide in the corresponding 8-nt substitution.
FIG. 13D is a graph showing the changes in induced activity owing to 5-nt (top) and 10-nt (bottom) insertions. The plots show the means of two different insertions (see also FIG. 15). Each bar is located one nucleotide to the right of the insertion. Error bars show the first and third quartile.
Figure 14:
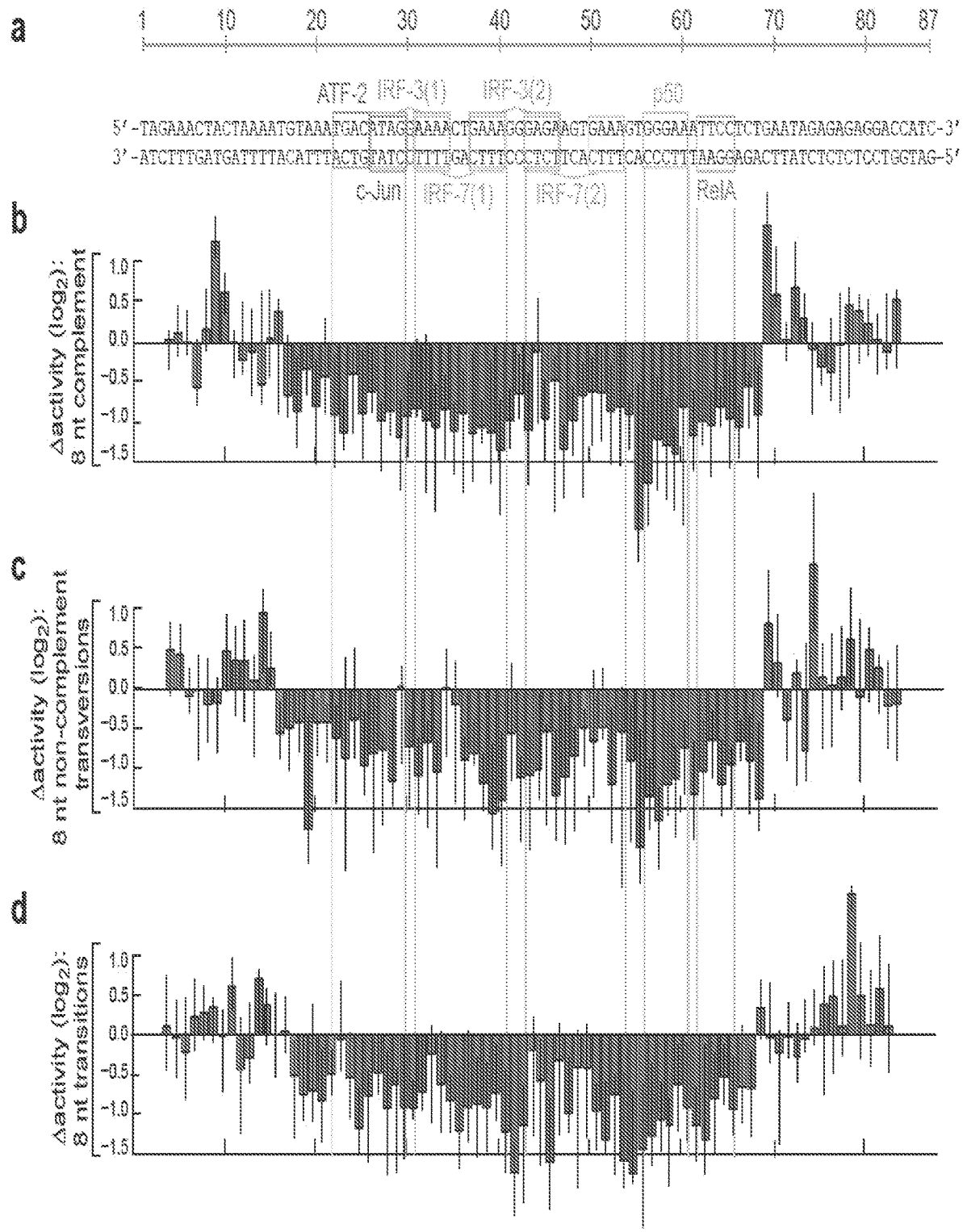
FIG. 14A shows the IFNB enhancer sequence (SEQ ID NOS: 43-44, respectively, in order of appearance) with known and putative transcription factor binding sites indicated.
FIG. 14B is a graph showing the changes in induced activity due to 8 consecutive complement substitutions ($G \leftrightarrows C$, $A \leftrightarrows T$).
FIG. 14C is a graph showing the changes in induced activity due to 8 consecutive non-complement transversion substitutions ($G \leftrightarrows T$, $A \leftrightarrows C$).
FIG. 14D is a graph showing the changes in induced activity due to 8 consecutive transition substitutions ($G \leftrightarrows A$, $T \leftrightarrows C$). Each bar is located at the fourth nucleotide in the corresponding 8 nucleotide substitution. Error bars show the first and third quartile.

The next focus was on the IFNB enhancer, which is a 44-nt sequence containing overlapping, nonconsensus binding sites for an ATF-2/c-Jun heterodimer, two IRF-3 and two IRF-7 proteins, and a p50/RELA (NF-κB) heterodimer (FIG. 13A) (Panne et al., Cell 129, 1111-1123, 2007). A small amount of flanking genomic sequence was included, for a total length of 87 nt. 83 of the 261 possible single substitutions altered the enhancer's activity in virus-infected cells (5% FDR), and almost all (92%) of these were within the 44-nt core (FIG. 13B). Scanning with consecutive substitutions did not reveal any unambiguously functional sequences outside of this core (FIG. 13C and FIG. 14).

Figure 15:
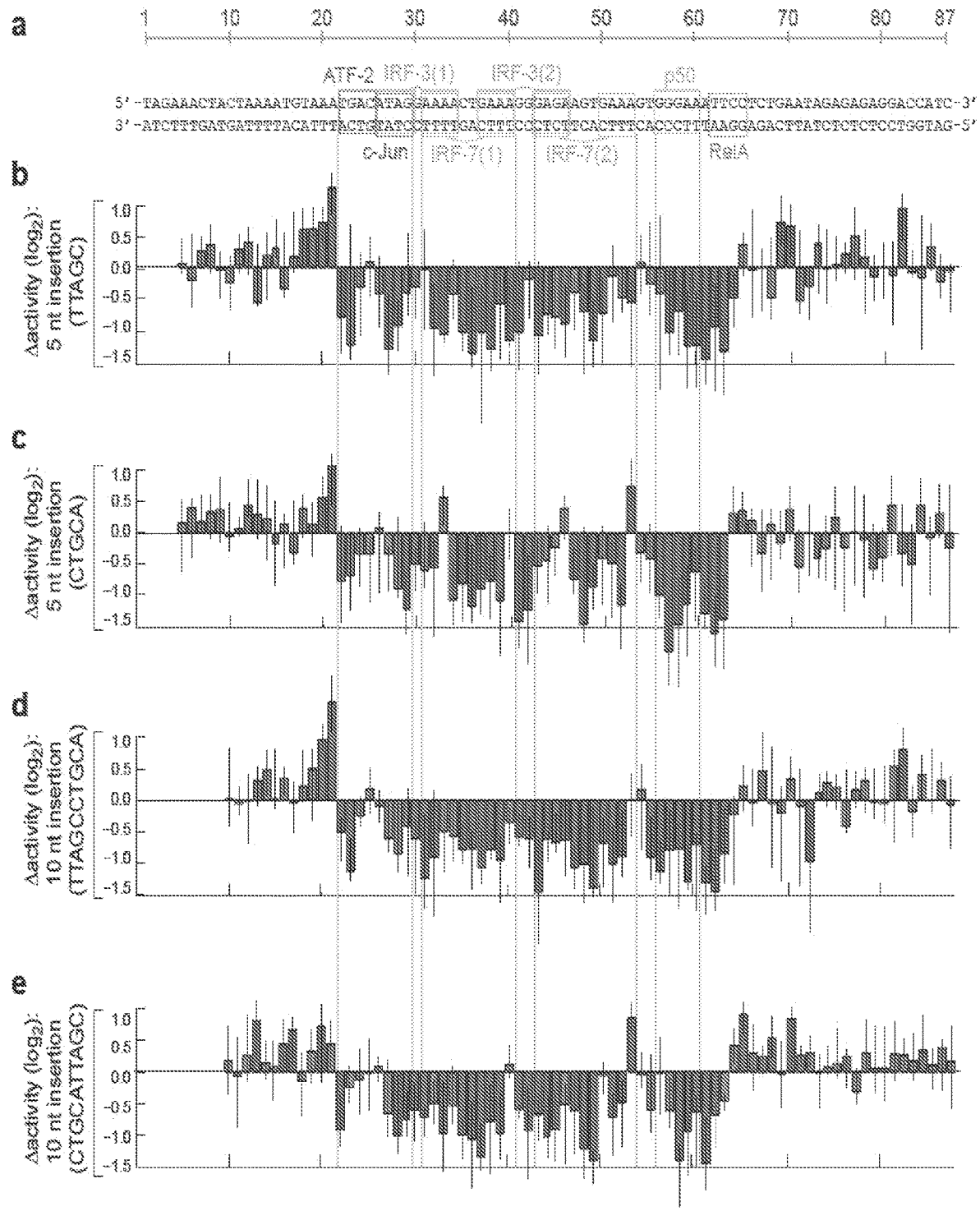
FIG. 15A shows the IFNB enhancer sequence (SEQ ID NOS: 43-44, respectively, in order of appearance) with known and putative transcription factor binding sites indicated.
FIG. 15B is a graph showing the changes in induced activity due to insertion of TTAGC between each pair of consecutive nucleotides.
FIG. 15C is a graph showing the changes in induced activity due to insertion of CTGCA between each pair of consecutive nucleotides.
FIG. 15D is a graph showing the changes in induced activity due to insertion of TTAGCCTGCA (SEQ ID NO: 1) between each pair of consecutive nucleotides.
FIG. 15E is a graph showing the changes in induced activity due to insertion of CTGCATTAGC (SEQ ID NO: 2) between each pair of consecutive nucleotides. Each bar is located one nucleotide to the right of the insertion. Error bars show the first and third quartile.

Within the core, there were only nine positions where all alternate nucleotides could be introduced without affecting the enhancer's activity. Strikingly, seven of these positions were in gaps between the 5'- and 3'-halves of IRF sites, where these proteins primarily interact with the DNA backbone (Panne et al., 2007). Insertions were also largely deleterious within the core (FIG. 13D and FIG. 15). Both 5- and 10-nt insertions were, however, tolerated between IRF-7 site 2 and the p50/RELA site, which is consistent with the absence of a known protein or interaction spanning this gap.

Finally, seven single substitutions within the core caused a significant increase in activity (5% FDR). At least four of these would be predicted to increase the affinity of a protein-DNA interaction, by introducing a central CG into the ATF-2/c-Jun site (TGAC$\underline{A}$TAG to TGAC$\underline{G}$TAG), changing the 3'-halves of IRF-3 site 1 or 2 to its consensus ($\underline{AAAA}$ or GA$\underline{GA}$ to $\underline{GA}$AA) or changing the NF-κB 5' half-site to a sequence specifically preferred by the p50 subunit (GGG$\underline{AA}$ to GGG$\underline{GA}$) (Kunsch et al., Mol. Cell. Biol. 12, 4412-4421, 1992). It should be noted that introduction of such consensus sites are, however, likely to decrease the specificity of the enhancer toward viral infection (see below and Falvo et al., Mol. Cell. Biol. 20, 4814-4825, 2000).

Figure 16:
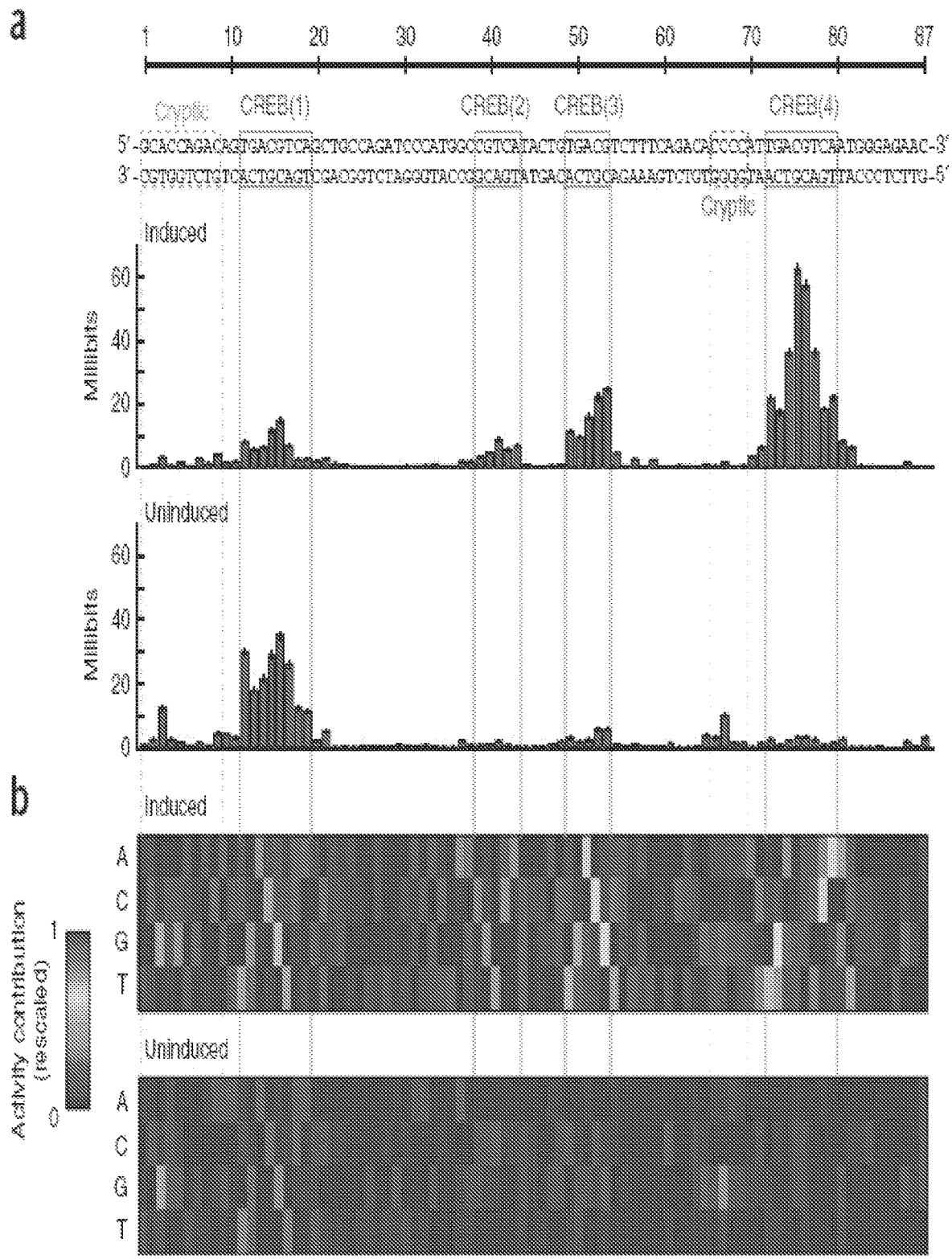
FIG. 16A shows a series of graphs showing information footprints of the CRE in its induced (top) and uninduced (bottom) states. Darker shading indicates significant information content at the corresponding position (permutation test, 5% FDR). Error bars show uncertainties inferred from subsampling.
FIG. 16B shows visual representations of linear QSAMs of the CRE in its induced (top) and uninduced (bottom) states. The shading in each entry represents the estimated additive contribution of the corresponding nucleotide to the log-transformed activity of the enhancer. The matrices are rescaled such that the lowest entry in each column is zero and the highest entry anywhere is one. Both matrices are shown on the same scale.
Figure 17:
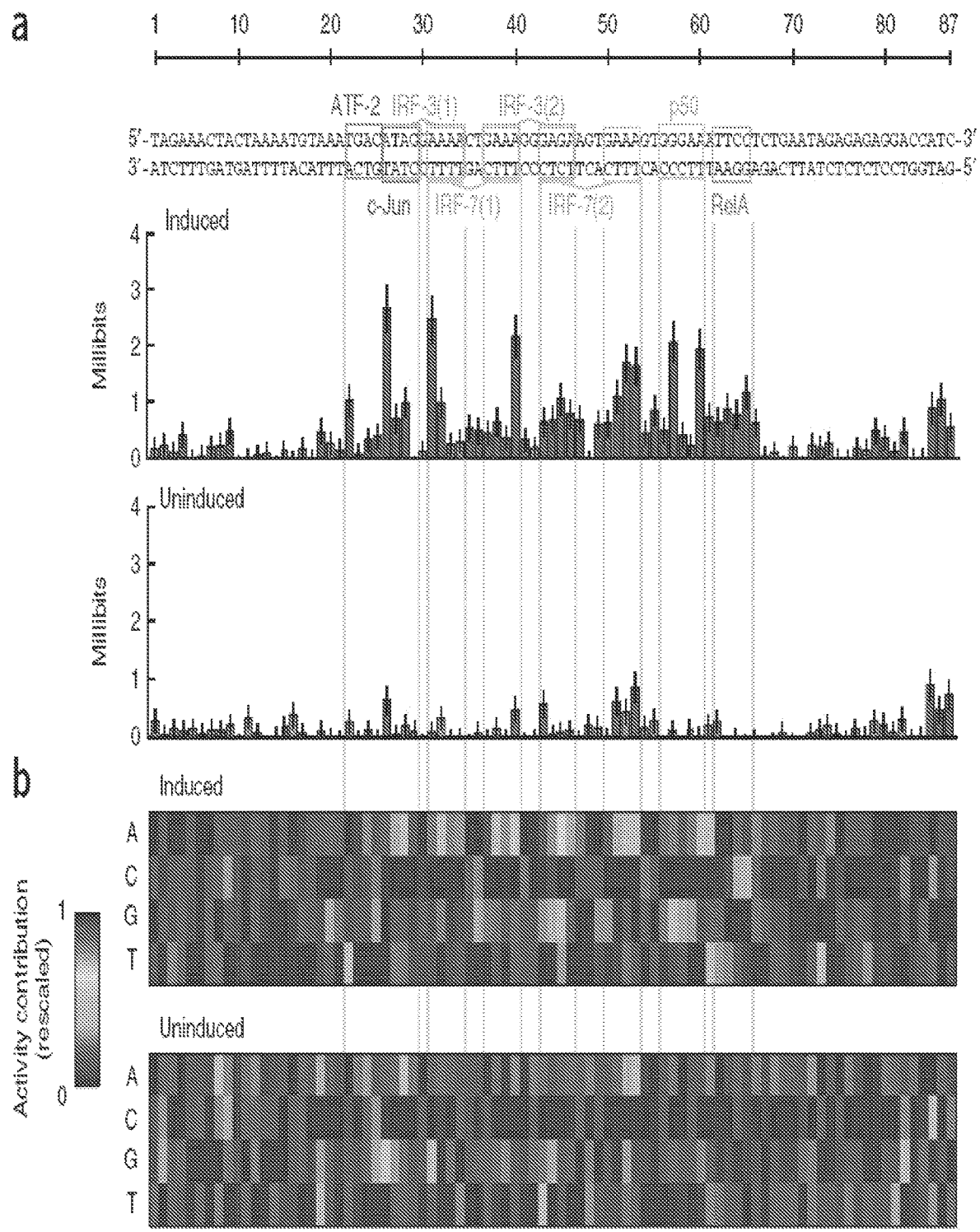
FIG. 17A shows a series of graphs showing information footprints of the IFNB enhancer in its induced (top) and uninduced (bottom) states. Darker shading indicates significant information content at the corresponding position (permutation test, 5% FDR). Error bars show uncertainties inferred from subsampling.
FIG. 17B shows visual representations of linear QSAMs of the IFNB enhancer in its induced (top) and uninduced (bottom) states. The shading in each entry represents the estimated additive contribution of the corresponding nucleotide to the log-transformed activity of the enhancer. The matrices are rescaled such that the lowest entry in each column is zero and the highest entry anywhere is one. Both matrices are shown on the same scale.

Next, the multi-hit sampling data were used in an attempt to dissect the two enhancers. To quantify the dependency between enhancer activity and substitutions at a specific position, the mutual information between the nucleotides at that position and the corresponding tag ratios across the ~27,000 variants were estimated. To infer the effect of substitutions on the basal enhancer activities, variants in untreated cells were also assayed. The resulting 'information footprints' (Kinney et al., Proc. Natl. Acad. Sci. USA 107, 9158-9163, 2010; Schneider et al., Nucleic Acids Res. 17, 659-674, 1989) are shown in FIGS. 16 and 17.

The 27 most informative positions in the induced CRE footprint were all located in or immediately flanking the four CREB sites (FIG. 16A). The more symmetric footprint of dimeric CREB site 4 compared to site 1 likely reflects the palindromic flanks of the former ($\underline{A}$TTGACGTCA$\underline{AT}$ (SEQ ID NO: 3) versus $\underline{AG}$TGACGTCA$\underline{GC}$ (SEQ ID NO: 4). The information contents of CREB sites 2-4 (i.e., the mutual information between their constituent nucleotides and the CRE activity) were substantially lower in the uninduced state, which is consistent with cAMP-dependence. In contrast, the information contents of CREB site 1 and the cryptic binding sites near CREB sites 1 and 4 were higher in the uninduced footprint. This is again consistent with the most promoter-distal CREB site being less cAMP-dependent (Mayr and Montminy, Nat. Rev. Mol. Cell Biol. 22, 1463-1469, 1994) and suggests that these sites may be important for controlling the basal CRE activity.

The IFNB enhancer footprint from virus-infected cells shows, as expected, that its functionally relevant nucleotides are concentrated in the 44-nt core (FIG. 17A). Indeed, 35 of 46 positions that had significant mutual information with the enhancer's activity (5% FDR) are located in the core. Strikingly, the uninduced IFNB footprint revealed only 8 informative positions, compared to 73 in the uninduced CRE footprint. This likely reflects the very low basal activity of the IFNB enhancer (at least fivefold lower than the uninduced CRE in luciferase assays).

Next, the development of quantitative sequence-activity models (QSAMs) (Kinney et al., Natl. Acad. Sci. USA 107, 9158-9163, 2010; Jonsson et al., Nucleic Acids Res. 21, 733-739, 1993; Stormo et al., Nucleic Acid Res. 14, 6661-6679, 1986) was attempted for the two enhancers, with the goal of predicting the activity of novel variants.

A description of the QSAMs used to fit to the data is provided below. QSAMs attempt to identify features of enhancer sequences that are predictive of the transcriptional activity of the regulated promoter. Several classes of models that instantiate, at varying levels of complexity, familiar ideas about how regulatory proteins can affect gene expression by binding to enhancer DNA were considered. Some of these QSAMs are motivated by heuristic considerations while others, as in Kinney et al. (2010), instantiate specific thermodynamic models.

QSAMs were fit to both CRE and IFNB data gathered in both inducing and non-inducing conditions. Specific formulae defining these QSAMs are displayed in Table 1, and information about model performance is displayed in Table 2. The models were in all cases fit to the copious multi-hit data. The quality of fit to this training data, as well as model performance on the sparser but independent single-hit data, was used to evaluate each QSAM's predictive power.

TABLE 1

| Formula for log expression from enhancer sequence σ | Parameters |
|---|---|
| $F_{lin}(\sigma) = \Sigma_{b,i} A_{bi} x_{bi}$ | $A_{bi}$ |
| $F_{lnl}(\sigma) = \log\{B + C[1 + \exp(\Sigma_{b,i} A_{bi} x_{bi})]^{-1}\}$ | $A_{bi}$, B, C |
| $F_{hlin}(\sigma) = B + \Sigma_s A_s x_s^{(1)}$ | $A_s$, B |
| $F_{nn}(\sigma) = \Sigma_{b,c,i} A_{bci} x_{b,i} x_{c,i+1}$ | $A_{bci}$ |
| $F_{arb}(\sigma) = \Sigma_{b,i} A_{bi} x_{bi} + \Sigma_{b,c,i,j} B_{bcij} x_{b,i} x_{c,j}$ | $A_{bi}$, $B_{bcij}$ |
| $F_{hint}(\sigma) = \Sigma_{b,i} A_{bi} x_{bi} + \Sigma_s B_s x_s^{(2)} + \Sigma_{s<t} C_{st} x_s^{(1)} x_t^{(1)}$ | $A_{bi}$, $B_s$, $C_{st}$ |
| $F_{therm}(\sigma) = \log\left(\tau \dfrac{Z_{on}}{Z_{on} + Z_{off}}\right)$ where $Z_{on} = e^{-\epsilon_P} [1 + \Sigma_s e^{-\epsilon_s - \gamma_s} + \Sigma_{s<t} e^{-\epsilon_s - \epsilon_t - \gamma_{st} - \omega_{st}} + \Sigma_{s<t<u} e^{-\epsilon_s - \epsilon_t - \epsilon_u - \gamma_{stu} - \omega_{stu}} + e^{-\epsilon_1 - \epsilon_2 - \epsilon_3 - \epsilon_4 - \omega_{1234} - \gamma_{1234}}]$ $Z_{off} = [1 + \Sigma_s e^{-\epsilon_s} + \Sigma_{s<t} e^{-\epsilon_s - \epsilon_t - \omega_{st}} + \Sigma_{s<t<u} e^{-\epsilon_s - \epsilon_t - \epsilon_u - \omega_{stu}} + e^{-\epsilon_1 - \epsilon_2 - \epsilon_3 - \epsilon_4 - \omega_{1234}}]$ $\epsilon_s = \Sigma_{b,i} A_{bi}^s x_{bi}$ | $A_{bi}^s$, $\omega_{st}$, $\omega_{stu}$, $\omega_{1234}$, $\gamma_s$, $\gamma_{st}$, $\gamma_{stu}$, $\gamma_{1234}$, $\tau$, $\epsilon_P$ |

Parameter indices are defined as follows: b, c ∈ {A, C, G, T} index different nucleotides; i, j ∈ {1, 2, ..., 87} index positions within the mutagenized enhancers; s, t, u index protein binding sites. $x_{bi} = 1$ (0 otherwise) if base b occurs at position i in the sequence σ. In the heuristic models, $x_s^{(n)} = 1$ (0 otherwise) if site s exhibits n or more mutations from wild type. $\epsilon_P$ is the RNAP binding free energy to its site, and $\epsilon_S$ is the binding free energy of a transcription factor (in this case CREB) to one of its specific binding sites indexed by s.

One of two objective functions, least squares or maximal mutual information, was used to optimize the parameters of each QSAM. For least squares, we sought parameters that minimized the sum of square deviations between model predictions and measured log activities. Least-squares-optimal parameters can easily be found using linear regression when a model's predictions depend linearly on these parameters. However, least squares have a maximum likelihood interpretation only when experimental noise is uniformly Gaussian.

each enhancer position i to log transcriptional activity. This is a generalization of a widely used method of assessing the effect of a single transcription factor acting at a single DNA binding site to the case where multiple transcription factors assemble on an extended enhancer. The model has 4×87=348 $A_{bi}$ parameters, but because one of the four bases must be present at every position there are only 1+3×87=262 independent degrees of freedom. The primary virtue of linear QSAMs is their simplicity, but it is not a priori obvious that such models can capture the complex response

TABLE 2

Summary of the QSAMs fit to multi-hit MPRA data. For each QSAM we report the following: the data set modeled; a description of the model that was fit (linear, heuristic linear, linear covering specific sites only, linear-nonlinear, nearest neighbor dinucleotide, arbitrary dinucleotide, heuristic interaction, and thermodynamic); the specific QSAM formula as described in Table 1, the number of independent parameters fit; the objective function used for model optimization, i.e., least squares (LS) or maximal mutual information (MMI); the computational method used to optimize parameters, i.e., linear regression (LR) or parallel tempering Monte Carl (PTMC); the squared Pearson correlation $r^2$ achieved by the model on the multi-hit training set and the single-hit test set (all values shown are highly significant, i.e., $p < 10^{-100}$); the mutual information between model predictions and multi-hit measurements, computed using the method of Strong et al., 1998. The induced CRE models were all fit to replicate 2 of the CRE multi-hit dataset.

| Multi-hit training dataset | Model description | Formula | No. of parameters | Objective function | Fitting method | $r^2$ on multi-hit data | $r^2$ on single-hit data | MI (bits) on multi-hit data |
|---|---|---|---|---|---|---|---|---|
| CRE, uninduced | linear | $F_{lin}$ | 262 | LS | LR | 0.359 | — | 0.355 ± .007 |
| CRE, induced | linear | $F_{lin}$ | 262 | LS | LR | 0.630 | 0.792 | 0.826 ± .008 |
| CRE, induced | linear | $F_{lin}$ | 262 | MMI | PTMC | 0.621 | 0.811 | 0.861 ± .008 |
| CRE, induced | linear (sites only) | $F_{lin}$ | 90 | LS | LR | 0.559 | 0.652 | 0.677 ± .006 |
| CRE, induced | linear/nonlinear | $F_{lnl}$ | 264 | LS | LR | 0.723 | 0.825 | 0.849 ± .008 |
| CRE, induced | heuristic linear | $F_{hlin}$ | 7 | LS | LR | 0.526 | 0.528 | 0.513 ± .007 |
| CRE, induced | n.n. dinucleotide | $F_{nn}$ | 1036 | LS | LR | 0.681 | 0.797 | 0.901 ± .007 |
| CRE, induced | arb. dinucleotide | $F_{arb}$ | 622 | LS | PTMC | 0.696 | 0.812 | 0.886 ± .006 |
| CRE, induced | heuristic int'n | $F_{hint}$ | 283 | LS | LR | 0.676 | 0.816 | 0.875 ± .008 |
| CRE, induced | thermodynamic | $F_{therm}$ | 122 | LS | PTMC | 0.655 | 0.688 | 0.717 ± .007 |
| IFNB, uninduced | linear | $F_{lin}$ | 262 | LS | LR | 0.021 | — | 0.017 ± .001 |
| IFNB, induced | linear | $F_{lin}$ | 262 | LS | LR | 0.071 | 0.616 | 0.058 ± .002 |
| IFNB, induced | linear | $F_{lin}$ | 262 | MMI | PTMC | 0.062 | 0.596 | 0.074 ± .003 |
| IFNB, induced | heuristic linear | $F_{hlin}$ | 9 | LS | LR | 0.034 | 0.425 | 0.064 ± .004 |
| IFNB, induced | n.n. dinucleotide | $F_{nn}$ | 1036 | LS | LR | 0.102 | 0.639 | 0.074 ± .002 |
| IFNB, induced | arb. dinucleotide | $F_{arb}$ | 622 | LS | PTMC | 0.104 | 0.607 | 0.073 ± .003 |
| IFNB, induced | heuristic int'n | $F_{hint}$ | 298 | LS | LR | 0.084 | 0.634 | 0.064 ± .003 |

In some cases, parameters that maximized the mutual information between model predictions and measured activities (Kinney et al., 2010) were also sought. Mutual information is equivalent, in the large data limit, to maximum likelihood whenever the quantitative form of experimental noise is uncertain (Kinney et al., Proc. Natl. Acad. Sci. USA 104, 501-506, 2007). Because of this, maximal mutual information is a more meaningful objective function than least squares when fitting QSAMs to MPRA data. However, mutual information cannot be maximized analytically. Therefore, the computationally intensive parallel tempering Monte Carlo (PTMC) algorithm from Kinney et al., 2010 was used to infer parameter values when using this objective function. PTMC was also used to perform least squares optimization on models for which simple linear regression could not be applied.

In general the CRE models performed much better than the IFNB models on their respective multi-hit training data, while both performed similarly on their respective single-hit test data. This difference is largely due to the IFNB enhancer, with its more compact enhanceosome structure, being more sensitive to multiple mutations than is the billboard-like CRE enhancer. Still, it is surprising that IFNB models that perform poorly on their multi-hit training data fit the single-hit test data so well.

Objective Functions and Optimization Strategies

Linear: A linear QSAM, $F_{lin}$, is defined by parameters $A_{bi}$ representing additive contributions of the different bases b at of multi-site enhancers. Nonetheless, for induced CRE and IFNB, linear QSAMs performed nearly as well or better than the more complex models we fit.

A "sites-only" linear QSAM was also defined in which the $A_{bi}$ parameters were fixed at zero for positions i outside identified transcription factor binding sites. This simplification was motivated by the assumption that discrete binding sites dominate model predictions. Such a model was fit to the induced CRE data, with nonzero positions restricted to the four CREB binding sites shown in FIG. 16 (but including two extra nucleotides included on each side of CREB site 4). Doing this reduced the number of model parameters from 262 to 90.

Heuristic Linear:

The heuristic linear QSAM, $F_{hlin}$, assumes that the effect of a binding site on log transcription is entirely determined by whether or not that site has at least one mutation with respect to wild type. When at least one mutation is present, a contribution $A_s$ is added to log activity. An advantage of this model is the very small number of parameters needed to describe it. Even with only 7 parameters (4 CREB sites, 2 "cryptic" sites and 1 overall constant), this model was able to achieve an $r^2$ value equal to 85% (65%) of that achieved by the linear QSAM on the induced CRE training (test) data.

Linear-Nonlinear:

In the linear-nonlinear QSAM, $F_{lnl}$, a sigmoidal transformation specified by parameters B and C is applied to the prediction of a linear QSAM having parameters $A_{bi}$ as defined above. This type of model is widely used to describe systems where multiple inputs are combined to generate a response that interpolates monotonically, but not linearly, between minimum and maximum values. For the induced CRE data, this two-parameter nonlinearity increased $r^2$ by 16% as compared to the linear QSAM. Because monotonic transformations have no effect on mutual information, this quantity was not meaningfully affected. Nevertheless, this linear-nonlinear model has the virtue of being able to predict an upper limit to the expression level that can be achieved by reengineering the enhancer sequence.

Nearest Neighbor Dinucleotide:

In modeling the binding specificity of individual transcription factors, the simple linear model can sometimes be improved upon—at the price of substantially increasing the number of parameters—by allowing for dependence on nucleotide pairs. To limit model complexity, it is convenient (and physically reasonable) to limit attention to nearest neighbor dinucleotides. We therefore defined a nearest neighbor dinucleotide QSAM, $F_{nn}$, in which parameters $A_{bci}$ give the additive contribution to log activity of the dinucleotide consisting of base b at position i and base c at position i+1. The simple mononucleotide model is included in this formulation as a special case. When applied to the induced CRE and IFNB data, the nearest neighbor dinucleotide model performed as well as, or better than, the simple linear model on both the training and test sets.

Arbitrary Dinucleotide:

To explore whether improvements in fit over the nearest neighbor model could be achieved with non-nearest neighbor interactions, we defined a hybrid dinucleotide QSAM, $F_{arb}$, consisting of a linear QSAM, defined by parameters $A_{bi}$ for all positions i, together with dinucleotide contributions $B_{bcij}$ describing interactions between bases b and c respectively occurring at selected pairs of positions i and j. To avoid overfitting due to an explosion of parameters, we limited nonzero $B_{bcij}$ values to at most 40 pairs of positions (i,j). Finding the 40 best pairs of positions, and the associated optimal parameter values, presented a combinatorial optimization problem, which we approached using PTMC. As the data in Table 2 indicate, these models performed similarly to the nearest neighbor dinucleotide models.

Heuristic Interaction:

The heuristic interaction QSAM, $F_{hint}$, consists of a linear QSAM with parameters $A_{bi}$, a heuristic linear model having parameters $B_s$ with a mutation threshold of 2, and additional interaction terms $C_{st}$ which contribute when both sites s and t have at least 1 mutation. For the CRE model, the 6 sites annotated in FIG. 16 were used. For the IFNB model, the 8 boxed regions (representing both sites and half-sites) were treated as separate sites. These models have the advantage of implementing interactions between proteins in a way that allows model parameters to be analytically inferred using linear regression. Modest improvements in fit as compared to the linear model were obtained.

Thermodynamic:

The thermodynamic QSAM for the induced CRE enhancer, $F_{therm}$, is based on previously published models (Bintu et al., Curr. Opin. Genet. Dev. 15(2), 125-135, 2005) in which transcriptional activity is assumed to be proportional to the equilibrium occupancy of the RNA polymerase site. Given a specific picture of how the regulatory proteins assemble on the enhancer, the polymerase site occupancy is determined by a partition function involving the binding free energies of transcription factors to their respective sites in the enhancer and the interaction free energies between both bound proteins and between these bound proteins and the polymerase. This sort of model has a complicated formula and cannot be fit with linear regression, but is important because it relates transcriptional response to a well-defined physical picture of molecular interactions. If a physically accurate model can be identified, it might facilitate the prediction of phenomena that could otherwise only be fit empirically. We attempted to fit one such model to the CRE data. This was not done for the IFNB data because the overlapping binding sites made it less clear what the structure of a reasonable thermodynamic model of that enhancer might be. In the formula for $F_{therm}$, $\varepsilon_s$ represents the binding free energy to site s, in natural thermal energy units ($k_B T$), of the cognate CREB protein. This free energy depends on sequence through a linear QSAM with parameters $A_{bi}^S$, and these parameters are nonzero only within the extent of site s (defined as for the linear sites-only CRE model). The $\omega$ parameters describe the energetic interactions between DNA-bound CREB proteins: $\omega_{st}$ is the interaction between proteins bound to sites s and t, $\omega_{stu}$ is the total interaction free energy between three proteins bound to sites s, t, and u and $\omega_{1234}$ is the total interaction free energy when all four CREB proteins are bound. Note that this model allows for irreducible 3-protein and 4-protein interactions, in addition to pairwise interactions between proteins. A constant of proportionality $\tau$ relates transcription to an effective RNA polymerase occupancy, which is determined by a protein-DNA interaction free energy $\varepsilon_p$, as well as interaction free energies $\gamma_s$, $\gamma_{st}$, $\gamma_{stu}$ and $\gamma_{1234}$ between RNA polymerase and the various possible CREB-enhancer complexes. Model parameters were fit using PTMC. This model fit the training set reasonably well but performed significantly worse than the simple linear model when predicting the single-hit test data.

Figure 18:
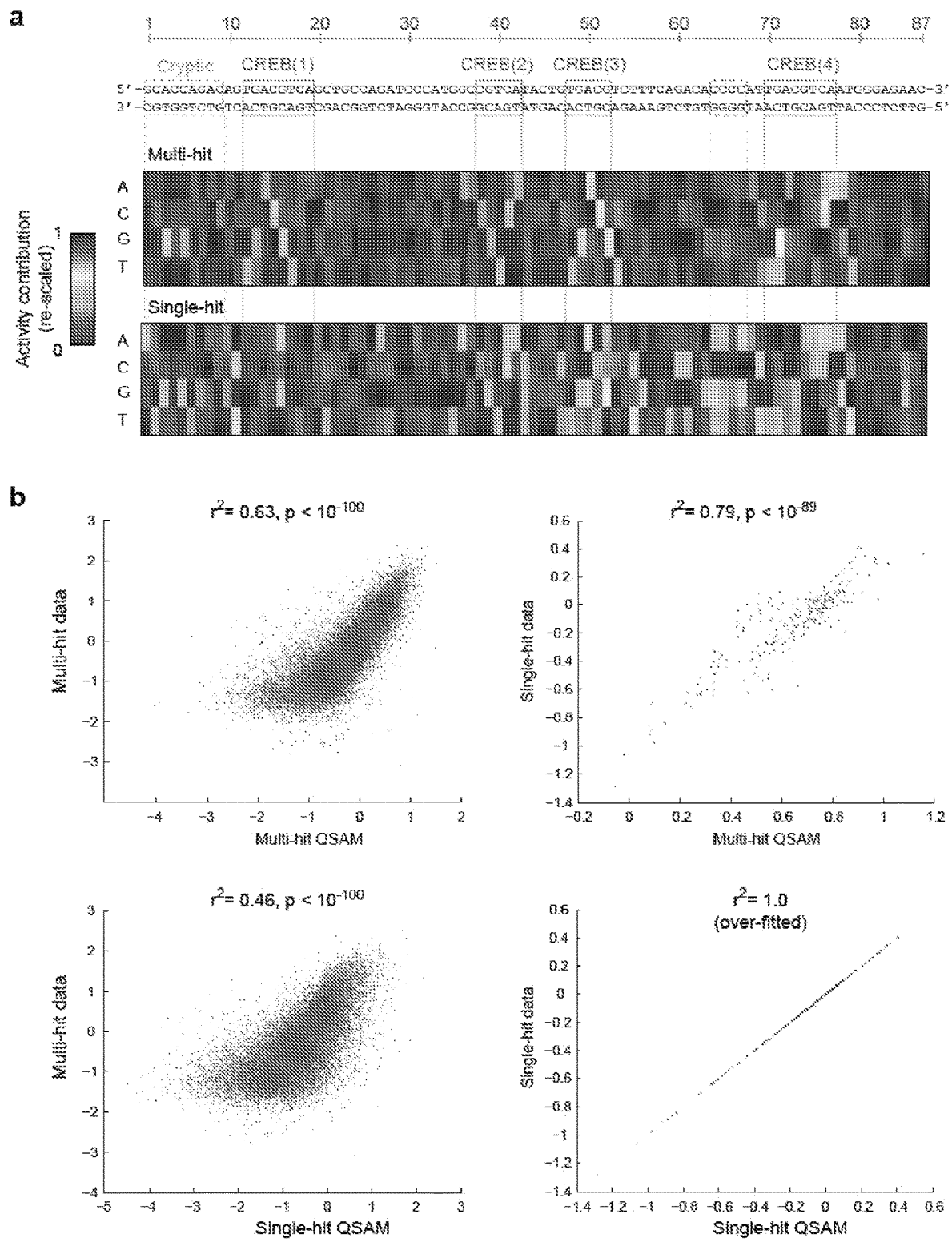
FIG. 18A shows visual representations of QSAMs trained on multi- (top) and single-hit (bottom) substitution data. The shading in each entry represents the estimated additive contribution of the corresponding nucleotide to the log-transformed activity of the enhancer. The matrices are re-scaled such that the lowest entry in each column is zero and the highest entry anywhere is one. Both matrices are shown on the same scale.
FIG. 18B is a series of graphs showing comparison of log-transformed QSAM-predicted and observed enhancer activities for models trained on multi-hit (top row) and single-hit (bottom row) data and evaluated on multi-hit (right column) or single-hit (left column) sequence variants. Note that the magnitudes of the activity estimates are depended on the specific set of assayed variants and therefore not directly comparable between single-hit and multi-hit data or QSAMs.
Figure 19:
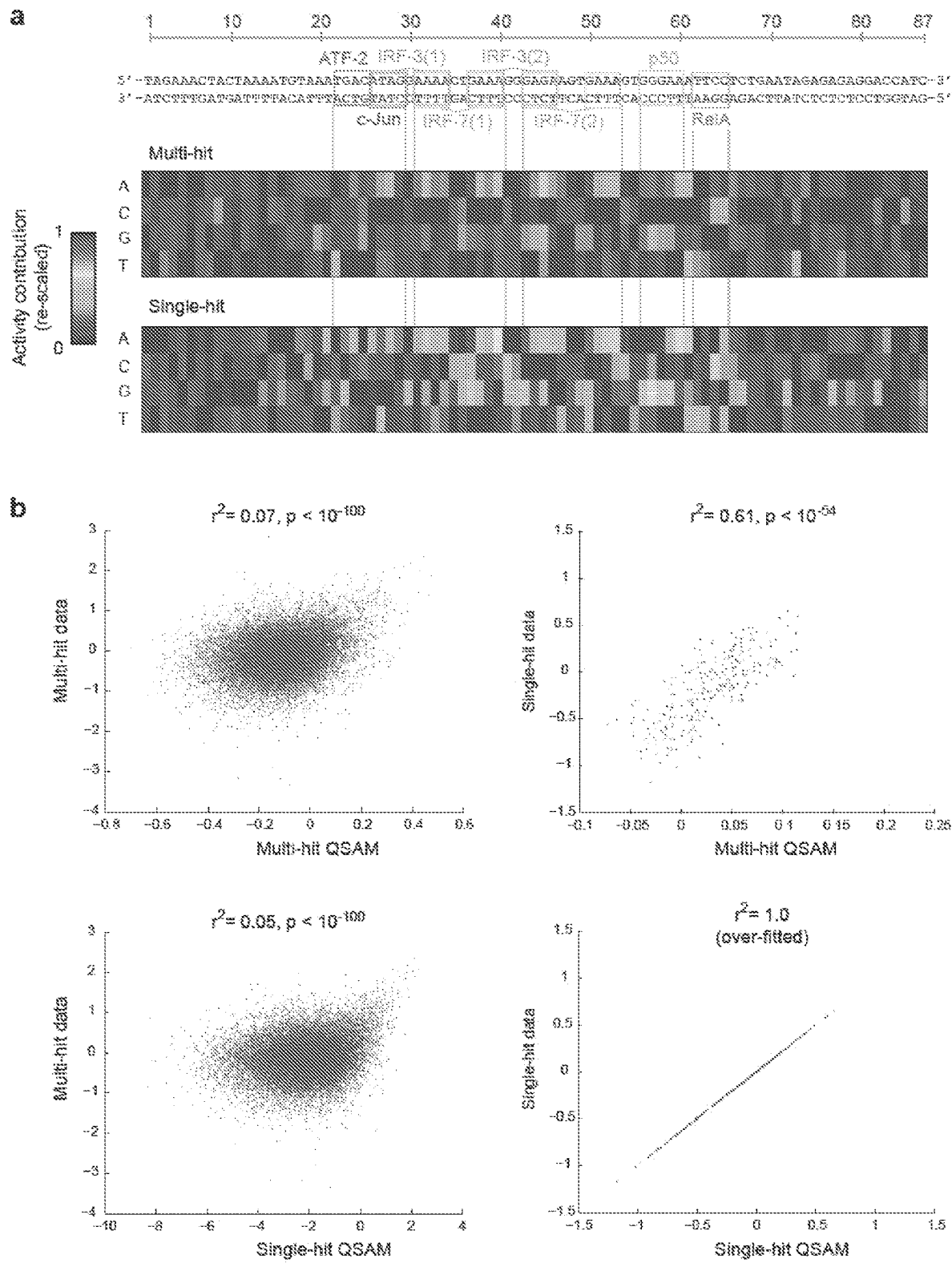
FIG. 19A shows visual representations of QSAMs trained on multi- (top) and single-hit (bottom) substitution data. The shading in each entry represents the estimated additive contribution of the corresponding nucleotide to the log-transformed activity of the enhancer. The matrices are re-scaled such that the lowest entry in each column is zero and the highest entry in each matrix is one. The two matrices are not shown on the same scale.
FIG. 19B is a series of graphs showing comparison of log-transformed QSAM-predicted and observed enhancer activities for models trained on multi-hit (top row) and single-hit (bottom row) data and evaluated on multi-hit (right column) or single-hit (left column) sequence variants. Note that the magnitudes of the activity estimates are depended on the specific set of assayed variants and therefore not directly comparable between single-hit and multi-hit data or QSAMs.

As a first step, linear regression was used to train QSAMs where each nucleotide position was simply assumed to contribute additively to the log-transformed activity of the enhancers in the induced or uninduced states (Jonsson et al., 1993; Stormo et al., 1986). Linear QSAMs trained on the multi-hit data are shown in FIGS. 16B and 17B (see FIGS. 18 and 19 for models trained on single-hit data). Inspection revealed good qualitative correspondence with the sequence features described above. For example, the two CRE models show that CREB site 1 is critical for maximizing the induced activity, whereas site 4 has the largest influence on the basal activity.

To quantify how well the linear models describe the data, their predictions to the observed activities for both the ~27,000 variants in the multi-hit training sets and the 261 single substitutions in the independent single-hit data were compared. For the CRE, the linear model for the induced state generated predictions that were highly correlated with the observed activities of both multi- and single-hit variants ($r^2=0.63$, $P<10^{-100}$ and $r^2=0.79$, $P<10^{-89}$, respectively). Remarkably, this model therefore explained ~90% of the nontechnical variance in both data sets (compare to $r^2=0.67$ and 0.89 between replicates, see above). The large number of multi-hit measurements ensured that this was not the result of overfitting ($r^2 \geq 0.62$ on fivefold cross-validation). In contrast, the induced IFNB model performed significantly better on single-hit variants ($r^2=0.61$, $P<10^{-54}$) than on multi-hit variants ($r^2=0.071$, $P<10^{-100}$), despite being trained on the latter set.

The difference in the fit of linear models appeared to reflect the different architectures of the enhancers. Most CRE multi-hit variants disrupted one or more of the non-overlapping consensus CREB sites, which caused large (median=4.7-fold) and roughly additive reductions in its induced activity, until an apparent minimum was reached (FIG. 18B). Multiple substitutions in the induced IFNB enhancer generally caused weaker (median=1.8-fold) and nonadditive reductions in activity, which may reflect its initially weaker nonconsensus binding sites or more complex interactions between its transcription factors.

Because both enhancers showed evidence of nonlinear responses, functional nonlinearities were incorporated in an attempt to refine the QSAMs. A variety of QSAMs were fitted to the data, including ones describing either dinucleotide interactions or biophysical interactions between DNA-bound proteins, as shown in Tables 1 and 2. Model parameters were optimized using linear regression or mutual information maximization (Kinney et al., 2010). For the CRE, the best performing QSAM was a 'linear-nonlinear' model (Bishop, *Pattern Recognition and Machine Learning*, Springer 2006) in which each nucleotide position is assumed to contribute additively to a linear activation measure, and a sigmoidal function of that measure then gives the transcriptional response. The optimal parameters for the linear part of this model are virtually identical ($r^2$=0.98) to the strictly linear QSAM, but the two additional parameters that describe the sigmoidal nonlinearity allow the model to describe both minimum and maximum activation levels. Notably, this nonlinearity appears to capture much of the remaining nontechnical variance in the induced CRE data ($r^2$=0.72, $P<10^{-100}$, compared to $r^2$=0.67 between the two replicates). For the IFNB enhancer, the best performing models were those that incorporated dinucleotide interactions, which is consistent with its more complex architecture, although no model provided more than a modest improvement over the linear QSAM (up to $r^2$=0.10, $P<10^{-100}$). Thus, although linear QSAMs are imperfect representations of the underlying biological systems, in these cases they appear to provide a reasonable trade-off between complexity and predictive power.

Figure 20:
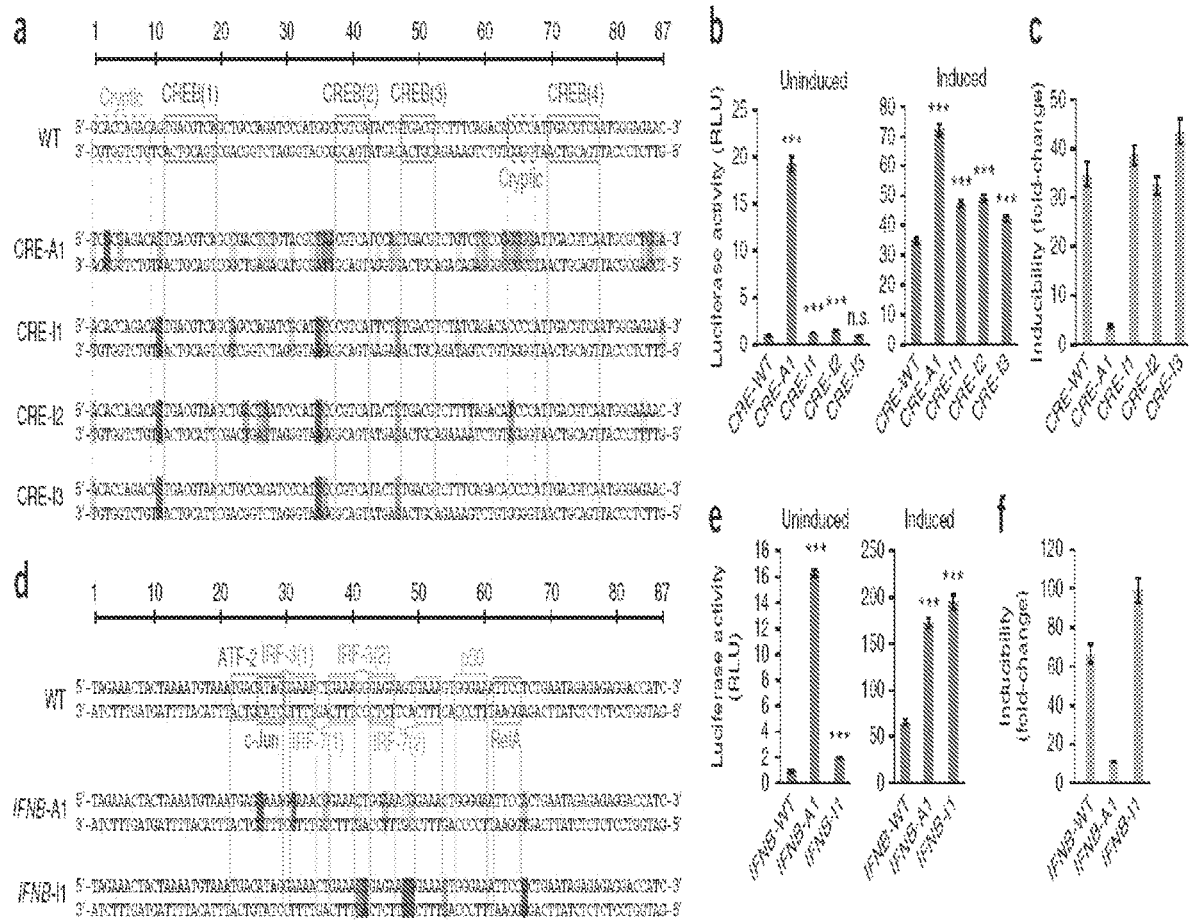
FIG. 20A shows CRE variant sequences predicted to maximize induced activity (A1) or inducibility (I1-I3) based on linear QSAMs trained on multi-hit data. Differences from wild type are indicated by shading. Darker shading indicates a higher predicted contribution to the change in activity.
FIG. 20B is a graph showing luciferase activity of the wild-type (WT) and optimized CRE variants in untreated and forskolin-treated cells. RLU, relative light unit. Bars show mean activity across 12 replicates in the induced or uninduced states.
FIG. 20C is a graph showing inducibility of the CRE variants in response to cAMP elevation caused by forskolin treatment. Bars show the ratio of the corresponding induced and uninduced mean activities.
FIG. 20D is a graph showing IFNB enhancer variants predicted to maximize induced activity (A1) or inducibility (I1) based on linear QSAMs trained on multi-hit data.
FIG. 20E is a graph showing luciferase activity of the WT and optimized IFNB enhancer variants in uninfected and virus-treated cells. Bars show mean activity across 12 replicates in the induced or uninduced states.
FIG. 20F is a graph showing inducibility of the IFNB enhancer variants in response to virus infection. Bars show the ratio of the corresponding induced and uninduced mean activities. Error bars show s.e.m. (SE). All statistical comparisons are relative to WT in the same state; n.s., not significant; ***, P≤0.0001; two-tailed t-test. Error bars show the range from (induced mean−induced SE)/(uninduced mean+uninduced SE) to (induced mean+induced SE)/(uninduced mean−uninduced SE).

Linear QSAMs have previously proven useful for engineering regulatory elements in bacteria. (Jonsson et al., 1993; De Mey et al., *BMC Biotechnol*. 7, 34, 2007). To explore the potential for model-based optimization of synthetic regulatory elements in mammals, an attempt was made to design enhancers with modified activities (FIG. 20).

A 'greedy' approach was used in the first attempt to maximize the induced enhancer activities. For each position, the nucleotide predicted to make the largest activity contribution according to the corresponding linear model, was selected. This resulted in changing the CRE at 36 of 87 positions (CRE-A1 in FIG. 20A). These changes left the consensus CREB sites intact, but introduced predicted activating mutations into the flanks of CREB sites 1-3 and into the two cryptic binding sites. For the IFNB enhancer, modifications were limited to the 44-nt core. This resulted in changes at 15 positions (IFNB-A1 in FIG. 20C), including conversion of every nonconsensus IRF half-site to the GAAA consensus and strengthening of the p50 half-site. These two variants were synthesized and then compared to their wild types using a luciferase assay. Both new variants had significantly higher induced activities (2.1-fold for CRE-A1, P<0.0001, and 2.6-fold for IFNB-A1, P<0.0001; FIGS. 20B,D). Notably, the increase for CRE-A1 (2.1-fold) was substantially lower than predicted by the simple linear model (32-fold), but close to the value predicted by the linear-nonlinear model (1.7-fold). In contrast, the increase for IFNB-A1 (2.6-fold) was close to the value predicted by its linear model (2.1-fold). This difference likely reflects that the wild-type CRE is composed of consensus activator sites and therefore operates much closer to saturation than the IFNB enhancer. However, both new variants had disproportionately higher uninduced activities (19-fold for CRE-A1 and 17-fold for IFNB-A1). This suggests that mutations that increase the induced activity of an enhancer may often decrease its inducibility, which would likely be detrimental in most biological and engineering contexts.

Figure 21:
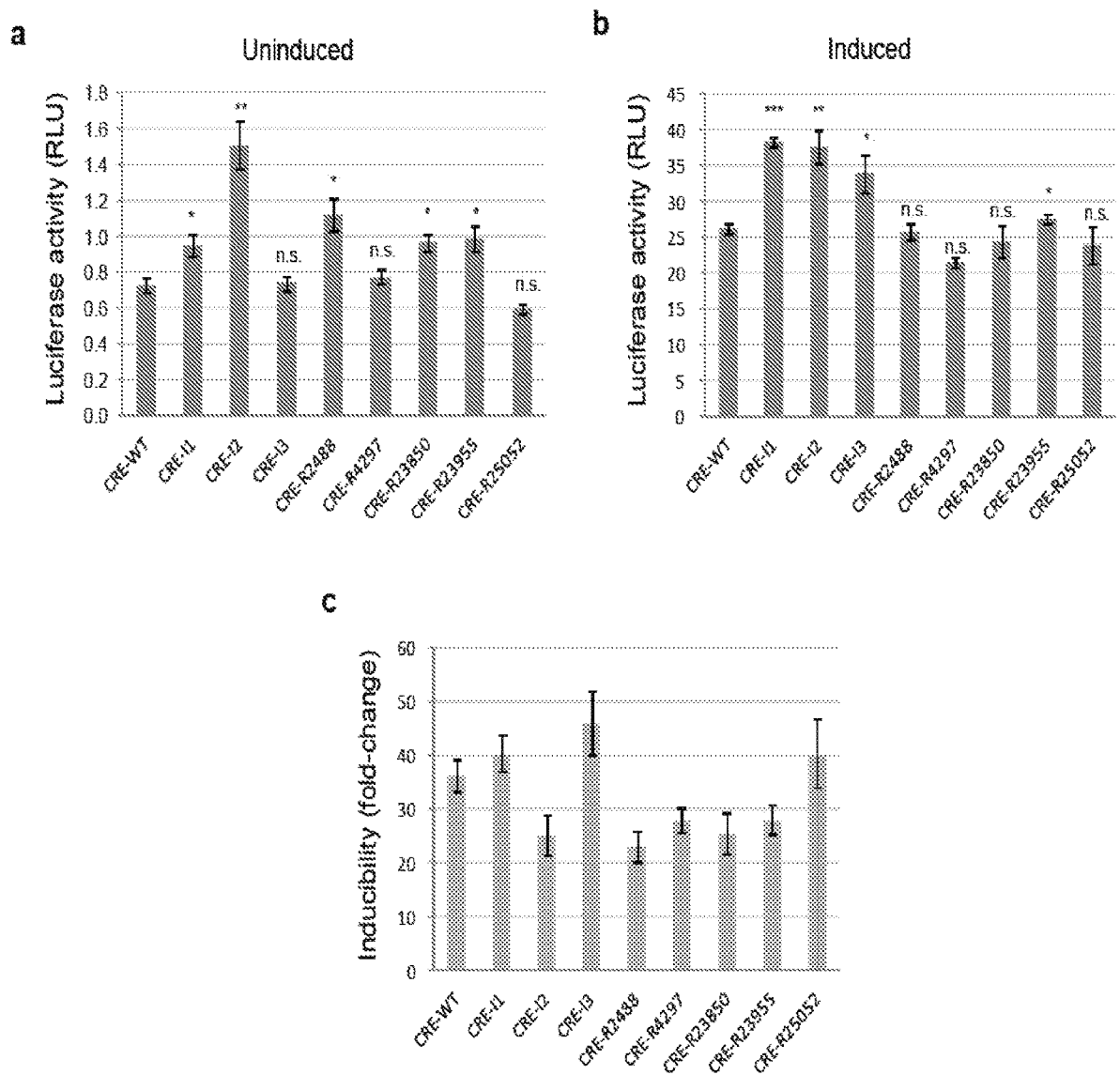
FIG. 21A is a graph showing luciferase activity of the wild-type (WT), optimized, and random CRE variants in untreated cells.
FIG. 21B is a graph showing luciferase activity of the same CRE variants in forskolin-treated cells. None of the top five random variants showed induced activities comparable to the engineered variants. Bars show mean activity across 3 replicates in the induced or uninduced states.
FIG. 21C is a graph showing inducibility of the CRE variants. Only one of the random variants (CRE-R25052) approached the level of inducibility seen for CRE-I1 and -I3, primarily because of its slightly reduced basal activity. Bars show the ratio of the corresponding induced and uninduced mean activities. Error bars show standard errors of the means (SE). All statistical comparisons are relative to WT in the same state; n.s., not significant; *, p≤0.05; , p≤0.01; *, p≤0.001; two-tailed t-test. Error bars show the range from (induced mean−induced SE)/(uninduced mean+uninduced SE) to (induced mean+induced SE)/(uninduced mean−uninduced SE).

Accordingly, maximization of the inducibility of the two enhancers was attempted. The induced and uninduced linear QSAMs were considered simultaneously, and for each position, the nucleotide predicted to maximize inducibility, without (i) increasing the uninduced activity or (ii) decreasing the induced activity relative to that of the wild type, was selected. For the CRE, three variants (CRE-I1 to CRE-I3 in FIG. 20A) were synthesized. CRE-I1 and -I2 were predicted by QSAMs trained on each of the two replicate CRE data sets and contained 10 and 12 substitutions, respectively. CRE-I3 contained only the five substitutions that were shared between the first two. Only one variant (CRE-I2) contained any activating substitutions in the cryptic motifs near CREB sites 1 and 4. All three variants showed a significant (P<0.0001) increase in induced activity without the large decrease in inducibility seen for CRE-A1 (FIG. 20B). Moreover, CRE-I3 showed no increase in uninduced activity, which resulted in a ~25% increase in inducibility relative to that of the wild type (~44-fold versus ~35-fold). Variants with similar or higher inducibilities from the original random variants (FIG. 21) could not be isolated. For the IFNB enhancer, we synthesized one variant containing five substitutions in the core, none of which modified the nonconsensus sites (IFNB-I1 in FIG. 20C). This variant also showed increased inducibility relative to that of the wild-type (~100-fold versus ~67-fold).

Figure 22:
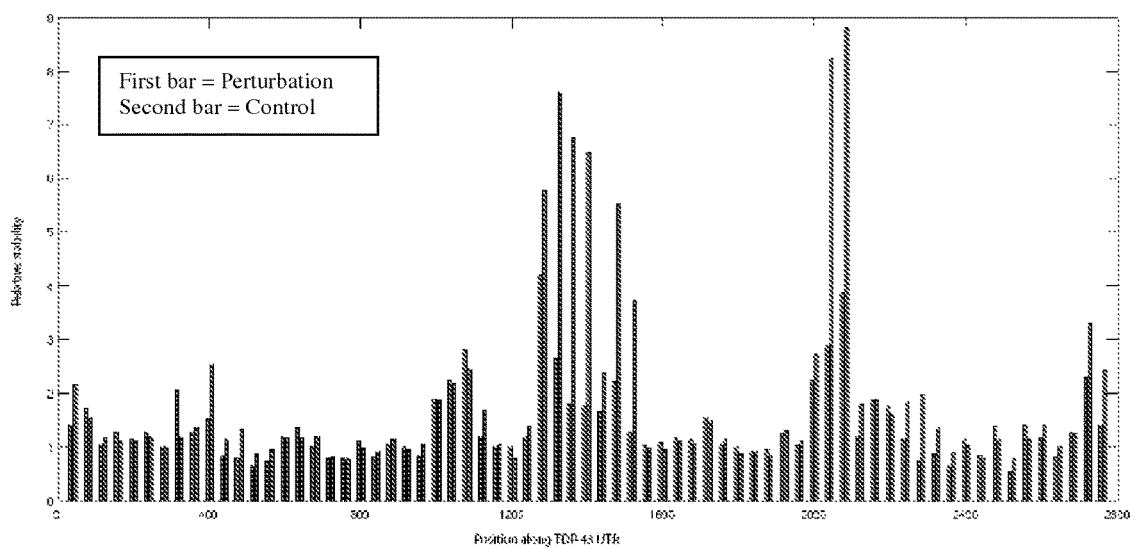
FIG. 22 is a graph showing the normalized mRNA tag counts ("relative stability") obtained from expression vectors that carried 142 nucleotide fragments of the human TDP-43 3' untranslated region 3' to the their open reading frames and identifying tags after siRNA depletion of TDP-43 ("perturbation," first bar) or in a control condition ("control," second bar). Fragments from two regions near positions ~1400 and ~2000 showed a relative increase in stability in the perturbed cells.

An additional experiment was performed using the method outlined in FIG. 1C. In this experiment, tens of thousands of oligonucleotides encoding a tag followed by 142 nucleotide fragments tiled at 40 nucleotide intervals of the 3' untranslated regions of 114 human genes, including TDP-43 (FIG. 22). Each variant was linked to one or more distinct tags. These variants were then cloned in parallel into an expression vector downstream of a synthetic promoter and an open reading frame encoding a luciferase. The expression vectors were co-transfected into HEK293 cells that had two days previously been transfected with siRNA targeting TDP-43 or a non-targeting control siRNA The relative transcriptional activities of the different variants were determined as described above. Several fragments were found to show differences in their relative stabilities between the perturbed (TDP-43 siRNA) and control (non-targeting siRNA) cells.

In summary, these experiments clearly demonstrate the generality of the methodologies described above and their application to study the composition of a synthetic cis-regulatory element used in high throughput drug screening. In addition, the two experiments together demonstrate how variant regulatory elements and nucleotide tags may be combined in different configurations to facilitate multiple types of experimental design and statistical analyses.

Methods

Figure 7:
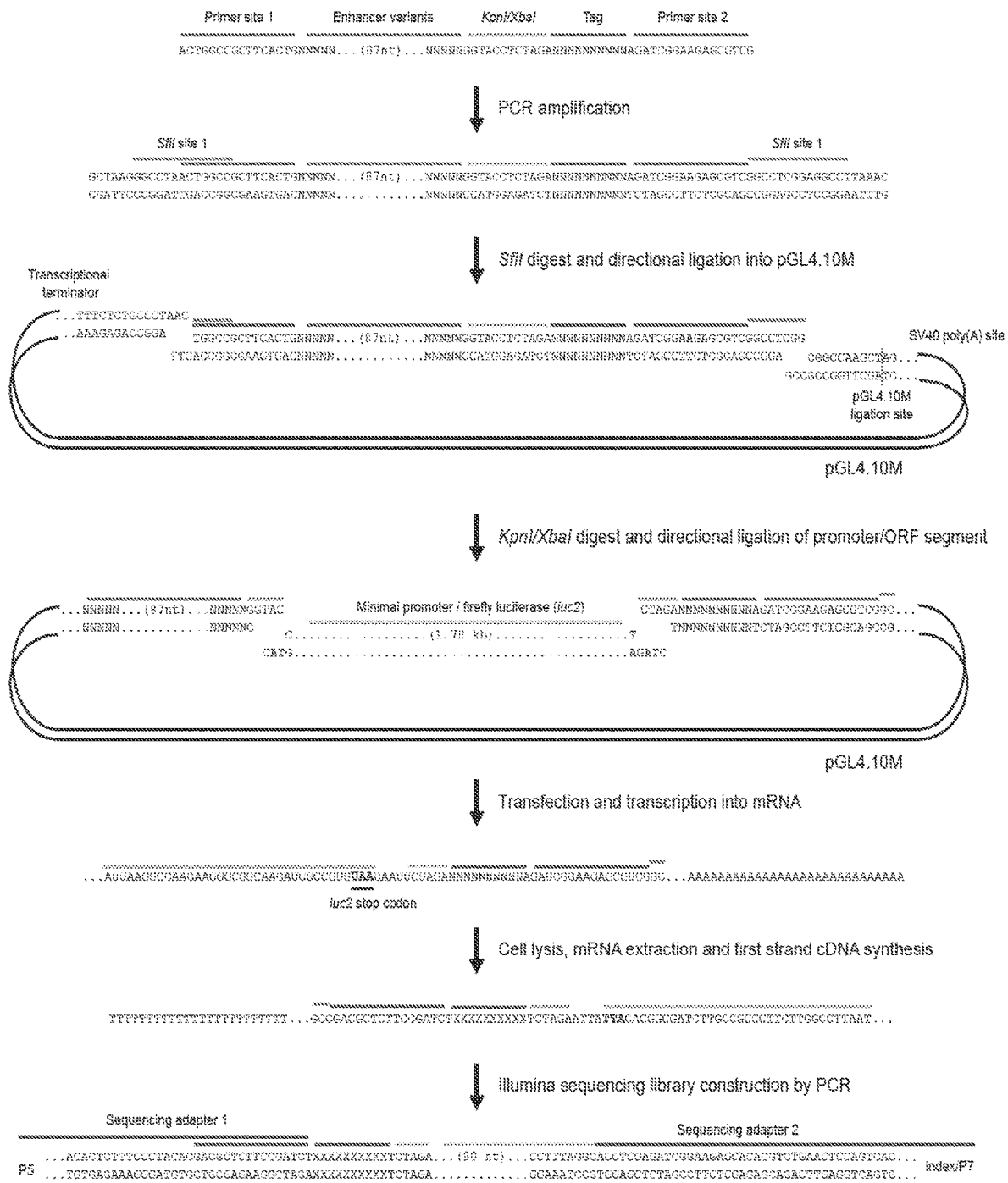
FIG. 7 is a schematic showing exemplary steps in the MPRA implementation described herein. Critical sequence features are highlighted.
Figure 8:
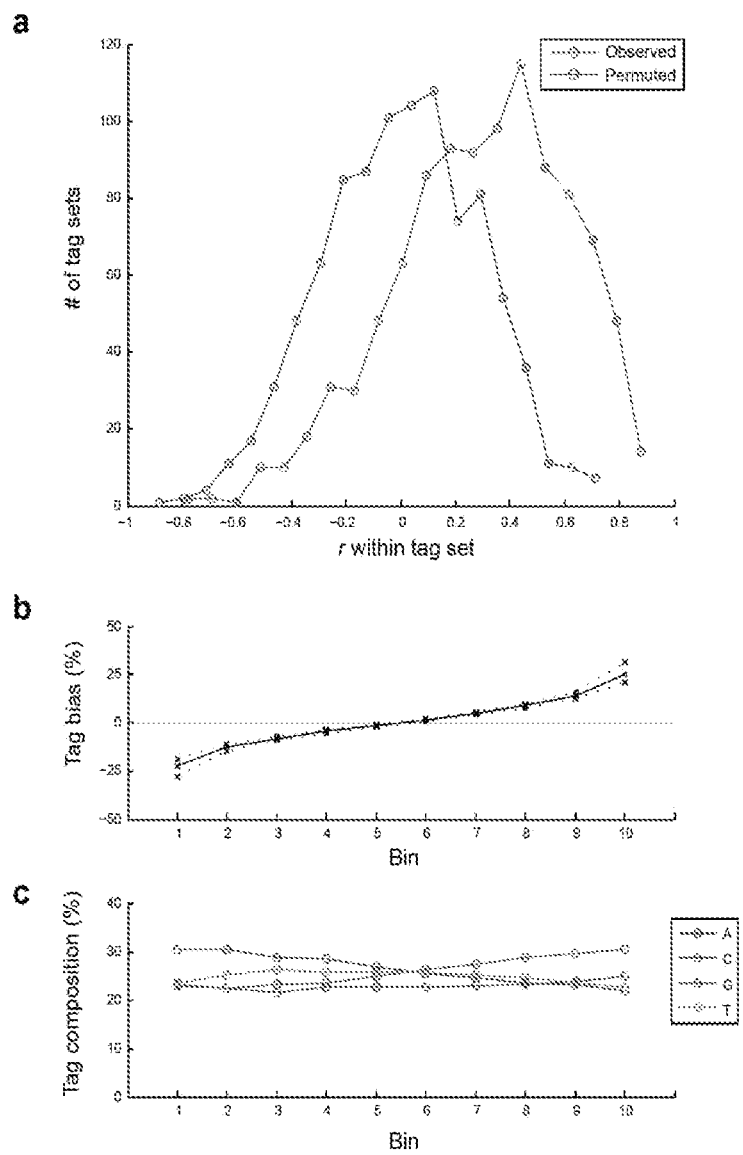
FIG. 8A is a graph showing the distribution of correlation coefficients (Pearson) between each set of 13 matching mRNA/plasmid tag ratios from the same single-hit CRE variant assayed in two independent MPRA experiments. We observed an excess of r values >0 relative to the expected distribution (estimated by permuting the association between tags and ratios within each set; median=0.0), which indicates a slight tag-related bias.
FIG. 8B is a graph showing the 'bias' of each of the ~13,000 tags utilized in the single-hit CRE design was estimated as the average of its two observed mRNA/plasmid ratios across the two experiments, divided by the average of the two median ratios from all 13 tags associated with the same variant. The tags were then sorted by their bias and partitioned into ten equally-sized bins. The plot shows the median bias for each bin (solid line; first and third quartiles shown as dotted lines). The majority (~80%) of tags had an estimated bias of less than ±15%.
FIG. 8C is a graph showing the mean nucleotide composition of tags in each of the ten bins. The tags with the most negative bias (i.e., those that appear to systematically underestimate the activity of their linked variant) tend to be more A-rich than unbiased tags, while the tags with the most positive bias (i.e., those that appear to systematically overestimate the activity of their linked variant) tend to be G-rich.

Oligonucleotide Library Design and Synthesis:

We designed 142-mer oligonucleotides to contain, in order, the universal primer site ACTGGCCGCTTCACTG, an 87-nt variable sequence, KpnI/XbaI restriction sites (GGTACCTCTAGA), a 10-nt variable tag sequence and the universal primer site AGATCGGAAGAGCGTCG (FIG. 7). The wild-type CRE sequence was derived from pGL4.29 (Promega). The wild-type interferon-β enhancer sequence was derived from the NCBI36/hg18 human genome reference assembly. The enhancer variants were designed as described in 'Experimental design and mutagenesis strategies', and 100 distinct wild-type enhancer-tag pairs were included in each multi-hit pool. The distinct tags were selected from randomly generated 10-nt sequences, with the following constraints: (i) must contain all four nucleotides, (ii) must not contain a run of more than four identical nucleotides, (iii) must not contain a KpnI or XbaI restriction site, and (iv) must not contain a known mammalian microRNA seed sequence (obtained from targetscan.org, April 2009).

The resulting oligonucleotide libraries were synthesized by Agilent as previously described (LeProust et al., *Nucleic Acids Res.* 38, 2522-2540, 2010). Sanger sequencing of subcloned MPRA plasmids suggested that the synthesis error rate was 1 in 200-300, with small deletions being the most common failure mode.

Plasmid Construction:

Oligonucleotide libraries were resuspended in TE 0.1 buffer (10 mM Tris-HCl, 0.1 mM EDTA, pH 8.0) and amplified using 8-12 cycles of PCR using Phusion High-Fidelity PCR Master Mix with HF buffer (New England Biolabs (NEB)) and primers ACTGGCCGCTTCACTG (SEQ ID NO: 5) and CGACGCTCTTCCGATCT (SEQ ID NO: 8). The resulting PCR products were selected on the basis of size on 4% NuSieve 3:1 agarose gels (Lonza), purified using QIAquick Gel Extraction kits (Qiagen) and reamplified with primers GCTAAGGGCCTAACTGGCCGCTTCACTG (SEQ ID NO: 9) and GTTTAAGGCCTCCGAGGCCGACGCTCTTC (SEQ ID NO: 10) to add SfiI sites.

To generate the plasmid backbone for the MPRA constructs, the luc2 reporter gene was removed from pGL4.10 [luc2] (Promega) by HindIII-XbaI digestion. The 5' extension of the HindIII site was filled in with Klenow fragment of DNA polymerase I (NEB) and the XbaI site was eliminated by treatment with Mung Bean nuclease (NEB). The resulting linear plasmid was self-ligated to generate cloning vector pGL4.10M.

To insert the variable regions into the MRPA vector, purified oligonucleotide PCR products were digested with SfiI (NEB) and directionally cloned into SfiI-digested pGL4.10M using One Shot TOP10 Electrocomp *E. coli* cells (Invitrogen). To preserve library complexity, the efficiency of transformation was maintained at >3×10$^8$ cfu/µg. Isolated plasmid pools were digested with KpnI/XbaI to cut between the enhancer variants and tags, ligated with the 1.78 kb KpnI-XbaI fragment of pGL4.23[luc2/minP] (Promega), which contains a minimal TATA-box promoter and the luc2 ORF, and then transformed into *E. coli* as described above. Finally, to remove vector background, the resultant plasmid pools were digested with KpnI, size selected on a 1% agarose gel, self-ligated and re-transformed into *E. coli*.

For validation of QSAM optimized enhancers, each variant was individually synthesized with the constant flanking sequences CTGGCCTAACTGGCCGCTTCACTG (SEQ ID NO: 11) and GGTACCTGAGCTCGC (SEQ ID NO: 12) (IDT). The oligonucleotides were PCR amplified as described above with primers CTGGCCTAACTGGCC (SEQ ID NO: 13) and GCGAGCTCAGGTACC (SEQ ID NO: 14), cloned into pGL4.24[luc2P/minP] (Promega) using the In-Fusion PCR Cloning System (Clontech) and verified by Sanger sequencing before transfection.

Cell Culture and Transfection:

HEK293T/17 cells (ATCC CRL-11268) were cultured in DMEM (Mediatech) supplemented with 10% FBS and L-glutamine/penicillin/streptomycin.

For transfection of a plasmid pool, 4×10$^6$ cells were grown to 40-50% confluence in a 10 cm culture dish. Cells were transfected with 10 µg DNA from each plasmid pool in 1 ml Opti-MEM I Reduced Serum Medium (Invitrogen) using 30 µl Lipofectamine LTX and 10 µl Plus Reagent (Invitrogen). The transfection mixtures were removed by media exchange after 5 h. After 24 h, cells transfected with CRE plasmid pools were treated for 5 h with 100 µM forskolin (Sigma) in DMSO (induced state) or an equivalent volume of DMSO only (uninduced state). Cells transfected with IFNB plasmid pools were infected with Sendai virus (ATCC VR-907) at an MOI of 10 (induced state) or mock infected (uninduced state) for 16 h. Immediately following these treatments, cells were lysed in RLT buffer (Qiagen) and frozen at −80° C. Total RNA was isolated from cell lysates using RNeasy kits (Qiagen).

For transfection of individual validation plasmids, 2.3× 10$^4$ cells were seeded into each well of 96-well plates. Each well was transfected with 15 µl of Opti-MEMO I Reduced Serum Medium (Invitrogen) containing 100 ng of luc2 reporter plasmid with CRE- or IFNB-derived variants and 10 ng of pGL4.73[hRluc/SV40] (Promega) for normalization, 0.25 µL Lipofectamine LTX and 0.1 µL Plus Reagent (Invitrogen). Cells were treated with forskolin or infected with Sendai virus as described above. Luciferase activities were measured using Dual-Glo Luciferase Assay (Promega) and an EnVision 2103 Multilabel Plate Reader (PerkinElmer).

Tag-Seq:

mRNA was extracted from total RNA using MicroPoly (A)Purist kits (Ambion) and treated with DNase I using the Turbo DNA-free kit (Ambion). First-strand cDNA was synthesized from 400-700 ng mRNA using High Capacity RNA-to-cDNA kits (Applied Biosystems).

Tag-Seq sequencing libraries were generated directly from 12% of a cDNA reaction or 50 ng plasmid DNA by 26 cycle PCR using Pfu Ultra HS DNA polymerase 2× master mix (Agilent) and primers AATGATACGGCGAC-CACCGAGATCTACACTCTTTCCCTA-CACGACGCTCTTCCGATCT (SEQ ID NO: 15) and CAAGCAGAAGACGGCAT-ACGAGATXXXXXXXXGTGACTGGAGTTCA-GACGTGTGCTCTTCCGATCTCGAGGTGCCTAAAGG (SEQ ID NO: 16) (where XXXXXXXX is a library-specific index sequence). The resultant PCR products were size-selected using 2% agarose E-Gel EX (Invitrogen). The libraries were sequenced in indexed pools of eight, or individually, using 36-nt single-end reads on Illumina HiSeq 2000 instruments.

To infer the tag copy numbers in each Tag-Seq library, all sequence reads were examined, regardless of their quality scores. If the first 10 nt of a read perfectly matched one of the 13,000 or 27,000 designed tags and the remaining nucleotides matched the expected upstream MPRA construct sequence, this was counted as one occurrence of that tag. All reads that did not meet this criterion were discarded. All tags that did not have a count of at least 20 in every sequenced CRE or IFNB enhancer plasmid pool were also discarded. The mRNA/plasmid tag ratios were normalized by multiplying by the ratio of the total number of plasmid and mRNA tag counts from the corresponding Tag-Seq libraries.

Analysis of Single-Hit Scanning Variants:

To estimate the relative activity of each distinct enhancer variant, the median of its 13 mRNA/plasmid tag ratios were compared to the median of the mRNA/plasmid ratios for tags linked to the corresponding WT enhancer. To increase the accuracy of this comparison, 65 distinct WT enhancer-tag pairs were included in each pool design. Significant differences in the median ratios were inferred by applying the Mann-Whitney U-test to all variant-WT pairs and then applying the Benjamini-Hochberg procedure to identify the 5% false discovery rate (FDR) threshold (Benjamini and Hochberg, *J.R. Stat. Soc. B* 57, 289-300, 1995).

Analysis of Multi-Hit Sampling Variants:

Information footprints were generated as described in Kinney et al. 2010. Briefly, the mRNA/plasmid tag ratios from each transfection experiment were first quantized by partitioning into five equally sized bins. The mutual information values between the bases at each position and the quantized activities were then estimated using the Treves-Panzeri limited sample correction (Treves and Panzeri, *Neural Comput.* 7, 399-407, 1995):

$$I(b_i; \mu) \approx \sum_{b_i, \mu} f(b_i, \mu) \log_2 \frac{f(b_i, \mu)}{f(b_i) f(\mu)} - \frac{6}{N} \log_2 e$$

where $b_i$ is the base at the ith position, $\mu$ is the quantized activity, $f()$ gives the corresponding joint and marginal frequency distributions and $N$ is the number of assayed variants.

Error bars on these values were determined by computing uncorrected mutual information estimates $I_{naive}^{50\%}(b_i;\mu)$ for 10,000 random sub-samples that each contained 50% of the enhancer variants. The uncertainties in $I(b_i;\mu)$ were computed from the variance of these estimates:

$$\delta I(b_i; \mu) = \frac{1}{\sqrt{2}} \sqrt{\text{var}(I_{naive}^{50\%}(b_i; \mu))}$$

To identify positions with significant information content, empirical null distributions for $I(b_i;\mu)$ were generated from 10,000 random permutations of the mapping between the quantized activities and the enhancer variants. The probability of the absence of information at the ith position was estimated as $(n_i+1)/10,000$, where $n_i$ is the number of random permutations for which $I(b_i;\mu)$ exceeded the original value. The Benjamini-Hochberg procedure was then applied to identify the 5% FDR threshold (Benjamini and Hochberg, 1995).

Quantitative sequence-activity modeling. The method of ordinary least-squares was used to train linear QSAMs of the form $$\log(\text{activity}(\sigma)) = \sum_{b,i} A_{bi} x_{bi}$$

where $A_{bi}$ is the activity contribution of base b at the ith position, and $x_b$, is an indicator variable that is 1 if the enhancer variant $\sigma$ contains base b at the ith position and 0 otherwise. Other models, including nonlinear QSAMs, are described in Supplementary Note 1.

Model-based optimization of the induced activity of each enhancer was performed by identifying and synthesizing $$\underset{\sigma}{\text{argmax}}\, \text{activity}^{induced}(\sigma)$$

based on the corresponding linear QSAMs (without interaction terms).

Model-based optimization of the inducibility of each enhancer was performed by identifying and synthesizing $$\underset{\sigma}{\text{argmax}} \frac{\text{activity}^{induced}(\sigma)}{\text{activity}^{uninduced}(\sigma)}$$

based on the corresponding linear QSAMs, with the constraints $$A_{\sigma i}^{induced} \geq A_{WTi}^{induced}$$

$$A_{\sigma i}^{uninduced} \leq A_{WTi}^{uninduced}$$

where WTi is the base at the ith position of the wild-type enhancer.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Use of singular forms herein, such as "a" and "the," does not exclude indication of the corresponding plural form, unless the context indicates to the contrary. Similarly, use of plural terms does not exclude indication of a corresponding singular form. Other embodiments are within the scope of the claims.

What is claimed is:

1. A plurality of expression vectors,
wherein each of said expression vectors comprises a nucleic acid regulatory element, an open reading frame, a pair of universal primer sites, and one or more identifying nucleic acid tags;
wherein the nucleic acid regulatory element, the open reading frame, and the one or more identifying nucleic acid tags are between the pair of universal primer sites;
wherein the open reading frame is located 3' to the nucleic acid regulatory element and the one or more identifying nucleic acid tags are located 3' to the open reading frame;
wherein the open reading frame of each of said plurality of expression vectors is identical, and optionally encodes a fluorescent protein or a luciferase;
wherein the plurality of expression vectors comprises a plurality of distinct nucleic acid regulatory elements, wherein the plurality of distinct regulatory elements comprises synthetic variants of a single regulatory element;
wherein each nucleic acid regulatory element is paired with the one or more identifying nucleic acid tags; and
wherein the pair of universal primer sites comprise a first primer site comprising the sequence of SEQ ID NO: 5 and a second primer site comprising the sequence of SEQ ID NO: 7.

2. A population of cells comprising the plurality of expression vectors of claim 1.

3. The plurality of expression vectors of claim 1, wherein each identifying tag comprises a sequence that is unique over a stretch of the nucleic acid tags, wherein the sequence that is unique may be continuous along the length of the nucleic acid tag sequence or the nucleic acid tag may include stretches of nucleic acid sequence that are not unique to any one tag.

4. The plurality of expression vectors of claim 1, wherein each expression vector further comprises an identical stretch of nucleotides located 3' to the identifying nucleic acid tags, and wherein optionally said identical stretch of nucleotides comprises a transcriptional terminator or poly-adenylation signal.

5. The plurality of expression vectors of claim 1, wherein (i) the variants of a single regulatory element differ from one another by a single nucleotide substitution, deletion, or insertion, optionally wherein among said variants of a single regulatory element are variant regulatory elements comprising single nucleotide substitutions of every nucleotide of said single regulatory element, or (ii) wherein each variant of a single regulatory element differs from the remaining variants of the single regulatory element by two or more single nucleotide substitutions, deletions, insertions, or combinations thereof.

6. The plurality of expression vectors of claim 1, wherein said plurality of expression vectors comprises at least 100 or more distinct expression vectors, and wherein the identifying nucleic acid tags are oriented in each of the plurality of expression vectors such that the identifying nucleic acid tags are transcribed in the same mRNA transcript as the associated open reading frame.

7. The plurality of expression vectors of claim 6, wherein said plurality of expression vectors comprises at least 500 distinct expression vectors, wherein the at least 500 distinct expression vectors each comprises a distinct nucleic acid regulatory element comprising a synthetic variant of a single regulatory element.

8. The plurality of expression vectors of claim 1, wherein each expression vector further comprises regions that facilitate stable integration into a cellular genome.

9. A method of determining individual activities of a plurality of nucleic acid regulatory elements, the method comprising:
introducing the plurality of expression vectors of claim 1 into cells in which said open reading frames and said tags are expressed, or providing cells with said plurality of expression vectors so introduced; and
determining expression of said tags expressed in the cells; wherein the amount of each tag detected is an indication of the activity of a corresponding nucleic acid regulatory element.

10. The method of claim 9, further comprising isolating mRNA from said cells prior to said determining the amount of said tags expressed in said cells.

11. The method of claim 10, wherein said mRNA isolated by poly-A isolation.

12. The method of claim 11, further comprising first strand cDNA synthesis using said isolated mRNA as a template.

13. The method of claim 12, wherein said determining the amount of said tags expressed in the cells comprises quantitatively sequencing the nucleic acid molecules resulting from said cDNA synthesis.

14. The method of claim 13, further comprising determining the amount of each tag in said plurality of expression vectors by quantitatively sequencing said plurality of expression vectors.

15. The method of claim 14, further comprising normalizing the amount of said tags expressed in the cells against the amount of each of said tags in said plurality of expression vectors.

16. The method of claim 10, wherein said determining the amount of said tags expressed in the cells comprises determining the quantity of mRNA hybridized to nucleic acid molecules complementary to said tags.

17. The method of claim 9, wherein each distinct regulatory element differs from the remaining distinct regulatory elements by a single nucleotide substitution, deletion, or insertion;
and wherein among said distinct regulatory elements are regulatory elements comprising single nucleotide substitutions of every nucleotide of said single regulatory element; or wherein said distinct regulatory elements comprisE regulatory elements that differ from said single regulatory element by one or more transversions or transpositions of stretches of nucleic acid sequences of greater than 4 nucleotides.

18. A plurality of nucleic acid constructs comprised within expression vectors,
wherein the plurality of nucleic acid constructs comprises a plurality of distinct nucleic acid regulatory elements, wherein the distinct regulatory elements comprise synthetic variants of a single regulatory element;
wherein each of said constructs comprises one or more identifying nucleic acid tags, two or more restriction enzyme sites, a pair of universal primer sites, and a particular nucleic acid regulatory element paired to said one or more nucleic acid tags,
wherein the nucleic acid regulatory element, two or more restriction enzyme sites, and one or more identifying nucleic acid tags are between the pair of universal primer sites;
wherein the two or more restriction enzyme sites are located 3' to the nucleic acid regulatory element and the one or more identifying nucleic acid tags are located 3' to the two or more restriction enzyme sites; and wherein the pair of universal primer sites comprise a first primer site comprising the sequence of SEQ ID NO: 5 and a second primer site comprising the sequence of SEQ ID NO: 7.

19. A method of determining individual activities of a plurality of nucleic acid regulatory elements, the method comprising:

providing the plurality of expression vectors of claim 18;

introducing said expression vectors into cells in which said open reading frames and said tags are expressed; and determining the amount of said tags expressed in the cells; wherein the amount of each tag detected is an indication of the activity of a corresponding nucleic acid regulatory element.

20. The method of claim 19, further comprising identifying variants of a nucleic acid regulatory element that have higher individual activities or higher relative differences in individual activities than said nucleic acid regulatory element, the method comprising:

determining the amount of said tags expressed in the cells in one or more cell population or experimental condition; wherein the amount of each tag detected is an indication of the activity of a corresponding nucleic acid regulatory element in each cell population or experimental condition; and determining the combined individual activities of each variant of said nucleic acid regulatory element from said cell populations or experimental conditions to identify variants that have higher individual activities or higher relative differences in individual activities than said nucleic acid regulatory element.

* * * * *

UNITED STATES PATENT AND TRADEMARK OFFICE
CERTIFICATE OF CORRECTION

PATENT NO. : 11,767,534 B2
APPLICATION NO. : 14/115608
DATED : September 26, 2023
INVENTOR(S) : Tarjei Mikkelsen et al.

It is certified that error appears in the above-identified patent and that said Letters Patent is hereby corrected as shown below:

On the Title Page

Item (56), in Column 2, under "Other Publications", Line 9, delete "19-19/19" and insert -- 1/19-19/19 --.

Item (57), in Column 2, in "Abstract", Line 8, delete "of" and insert -- of, --.

Item (57), in Column 2, in "Abstract", Line 9, delete "as says" and insert -- assays --.

In the Specification

In Column 7, Line 2, delete "17-19" and insert -- 17-19, --.

In Column 8, Line 6, delete "(G⇌C, A⇌T)." and insert -- (G↔C, A↔T). --.

In Column 8, Line 9, delete "(G⇌T, A⇌C)." and insert -- (G↔T, A↔C). --.

In Column 8, Lines 11-12, delete "(G⇌A, T⇌C)." and insert -- (G↔A, T↔C). --.

In Column 8, Line 55, delete "(G⇌C, A⇌T)." and insert -- (G↔C, A↔T). --.

In Column 8, Line 58, delete "(G⇌T, A⇌C)." and insert -- (G↔T, A↔C). --.

In Column 8, Lines 60-61, delete "(G⇌A, T⇌C)." and insert -- (G↔A, T↔C). --.

In Column 10, Line 32, delete "data.FIG." and insert -- data. FIG. --.

In Column 18, Lines 8-9, after "transfection." delete "The resulting data using several different approaches were validated as shown in FIG. 9.".

Signed and Sealed this
Twenty-eighth Day of May, 2024

Katherine Kelly Vidal
*Director of the United States Patent and Trademark Office*

CERTIFICATE OF CORRECTION (continued)
U.S. Pat. No. 11,767,534 B2

In Column 18, Line 10, before "First," insert -- The resulting data using several different approaches were validated as shown in FIG. 9. --.

In Column 19, Line 67, delete "4)." and insert -- 4)). --.

In Column 20, Line 58, delete "$e^{-\epsilon 1-\epsilon 2-\epsilon 3-\epsilon 4-\omega 1234-\gamma 1234}]$" and insert -- $e^{-\epsilon_1-\epsilon_2-\epsilon_3-\epsilon_4-\omega_{1234}-\gamma_{1234}}]$ --.

In Column 20, Line 60, delete "$e^{-\epsilon 1-\epsilon 2-\epsilon 3-\epsilon 4-\omega 1234}]$" and insert -- $e^{-\epsilon_1-\epsilon_2-\epsilon_3-\epsilon_4-\omega_{1234}}]$ --.

In Columns 21-22, Line 8 (Table 2), delete "$10^{-100}$);" and insert -- $10^{-100}$); --.

In Column 26, Line 62, delete "ACTGGCCGCTTCACTG," and insert -- ACTGGCCGCTTCACTG (SEQ ID NO: 5), --.

In Column 26, Line 64, delete "(GGTACCTCTAGA)," and insert -- (GGTACCTCTAGA) (SEQ ID NO: 6), --.

In Column 26, Line 65, delete "AGATCGGAAGAGCGTCG" and insert -- AGATCGGAAGAGCGTCG (SEQ ID NO: 7) --.

In Column 30, Line 2, delete "$x_b$," and insert -- $x_{bi}$ --.

In Column 30, Line 11, delete "$\operatorname*{argmax}_{\sigma} activity^{induced}(\sigma)$" and insert -- $\arg\max_{\sigma} activity^{induced}(\sigma)$ --.

In Column 30, Line 20, delete "$\operatorname*{argmax}_{\sigma}$" and insert -- $\arg\max_{\sigma}$ --.

In the Claims

In Column 58, Line 43, in Claim 17, before "wherein" delete "and".

In Column 58, Line 47, in Claim 17, delete "comprisE" and insert -- comprise --.